(12) United States Patent
Froseth et al.

(10) Patent No.: US 8,249,946 B2
(45) Date of Patent: Aug. 21, 2012

(54) CUSTOMIZED FOOD SELECTION, ORDERING AND DISTRIBUTION SYSTEM AND METHOD

(75) Inventors: Barrie R. Froseth, Plymouth, MN (US); Raymond Bowers, Plymouth, MN (US); Katy P. Dickson, Eden Prairle, MN (US); Mike E. Geddis, Plymouth, MN (US); Myer Joy, Morges (CH); Paul Muller, Shorewood, MN (US); Kimberly A. Nelson, Plymouth, MN (US); Lisa R. Schroeder, Plymouth, MN (US); Sheri M. Schellhaass, Plymouth, MN (US); Jeffrey D. Thoresen Severts, Minneapolis, MN (US); Bernhard Van Lengerich, Plymouth, MN (US); David E. Williams, Chanhassen, MN (US); Philip K. Zietlow, Wayzata, MN (US)

(73) Assignee: General Mills, Inc., Minneapolis, MN (US)

( * ) Notice: Subject to any disclaimer, the term of this patent is extended or adjusted under 35 U.S.C. 154(b) by 1349 days.

(21) Appl. No.: 11/889,883

(22) Filed: Aug. 17, 2007

(65) Prior Publication Data
US 2007/0294129 A1    Dec. 20, 2007

Related U.S. Application Data

(63) Continuation of application No. 09/780,273, filed on Feb. 9, 2001, now abandoned, which is a continuation of application No. 09/699,622, filed on Oct. 29, 2000, now abandoned.

(60) Provisional application No. 60/181,282, filed on Feb. 9, 2000.

(51) Int. Cl.
*G06Q 30/00*    (2012.01)

(52) U.S. Cl. ............... 705/26.5; 705/26.1; 705/27.1; 416/72; 426/72; 426/103; 426/615; 426/619

(58) Field of Classification Search .............. 705/26, 705/27, 26.5, 26.1, 27.1; 426/72, 103, 615, 426/619; 416/72
See application file for complete search history.

(56) References Cited

U.S. PATENT DOCUMENTS
2,802,599 A    8/1957    Callahan et al.
(Continued)

FOREIGN PATENT DOCUMENTS
DE            4323788            7/1993
(Continued)

OTHER PUBLICATIONS

"Munchables. Fast, Fresh, Fun , Fit Foods", *Munchables, Inc.*, http://www.munchables.com, 3 pages, 2000.
(Continued)

*Primary Examiner* — Yogesh C Garg
(74) *Attorney, Agent, or Firm* — Everett Diederiks

(57) ABSTRACT

A system and method for selecting, ordering and distributing customized food products is disclosed. In one embodiment, the method is a computer-implemented method comprising viewing a list of additives for creating a customized food product, selecting one or more additives from the list of additives to create the customized food product, and transmitting a request to purchase the customized food product, which is then distributed to the consumer. By communicating with the manufacturer as to personal needs and desires pertaining to health, activity level, organoleptic preferences and so forth, the consumer can now develop and order a customized food product to suit his or her particular tastes, using a real-time interactive communication link.

34 Claims, 40 Drawing Sheets

U.S. PATENT DOCUMENTS

| | | | |
|---|---|---|---|
| 3,843,814 A | 10/1974 | Grunewald-Kirstein | |
| 3,851,574 A | 12/1974 | Katz et al. | |
| 4,398,721 A | 8/1983 | McKay | |
| 4,751,090 A | 6/1988 | Belleson et al. | |
| 4,767,635 A | 8/1988 | Merritt et al. | |
| 4,904,488 A | 2/1990 | LaBaw et al. | |
| 4,918,182 A | 4/1990 | Jackson et al. | |
| 5,041,541 A | 8/1991 | Mazur | |
| 5,120,563 A | 6/1992 | Mohlenkamp, Jr. et al. | |
| 5,196,218 A | 3/1993 | Schwab et al. | |
| 5,200,222 A | 4/1993 | Schwab et al. | |
| 5,284,666 A | 2/1994 | Graf | |
| 5,338,556 A | 8/1994 | Schwab et al. | |
| 5,412,560 A | 5/1995 | Dennison | |
| 5,441,751 A * | 8/1995 | Vagani | 426/27 |
| 5,443,858 A | 8/1995 | Jensen et al. | |
| 5,650,084 A | 7/1997 | Bley | |
| 5,688,543 A | 11/1997 | Freeport et al. | |
| 5,715,399 A | 2/1998 | Bezos | |
| 5,715,402 A | 2/1998 | Popolo | |
| 5,747,080 A | 5/1998 | Lemke et al. | |
| 5,747,091 A | 5/1998 | Denhartog et al. | |
| 5,750,166 A | 5/1998 | Schellhaass | |
| 5,753,287 A | 5/1998 | Chedid et al. | |
| 5,774,873 A | 6/1998 | Berent et al. | |
| 5,878,910 A | 3/1999 | Gibernau et al. | |
| 5,897,620 A | 4/1999 | Walker et al. | |
| 5,897,894 A | 4/1999 | Glass | |
| 5,902,797 A | 5/1999 | Bell et al. | |
| 5,907,275 A * | 5/1999 | Battistini et al. | 340/286.09 |
| 5,919,505 A | 7/1999 | Monsalve et al. | |
| 5,952,026 A | 9/1999 | Greenway et al. | |
| 5,954,640 A * | 9/1999 | Szabo | 600/300 |
| 5,960,411 A | 9/1999 | Hartman et al. | |
| 5,977,059 A | 11/1999 | Khoo et al. | |
| 5,993,869 A | 11/1999 | Freeport | |
| 5,994,295 A | 11/1999 | Khoo et al. | |
| 5,997,924 A * | 12/1999 | Olander et al. | 426/296 |
| 6,013,291 A | 1/2000 | Glass et al. | |
| 6,064,980 A | 5/2000 | Jacobi et al. | |
| 6,070,149 A | 5/2000 | Tavor et al. | |
| 6,099,877 A | 8/2000 | Schuppan | |
| 6,182,097 B1 | 1/2001 | Hansen et al. | |
| 6,210,720 B1 | 4/2001 | Leusner et al. | |
| 6,210,721 B1 | 4/2001 | Dickerson et al. | |
| 6,248,379 B1 | 6/2001 | Capodieci et al. | |
| 6,358,546 B1 | 3/2002 | Bebiak et al. | |
| 6,413,558 B1 | 7/2002 | Weber et al. | |
| 6,618,062 B1 | 9/2003 | Brown et al. | |
| 2002/0081356 A1* | 6/2002 | Bebiak et al. | 426/232 |
| 2002/0127306 A1 | 9/2002 | Schmidt et al. | |
| 2003/0028885 A1* | 2/2003 | Wilcox et al. | 725/60 |

FOREIGN PATENT DOCUMENTS

| | | |
|---|---|---|
| EP | 0260979 | 3/1988 |
| EP | 0335852 | 10/1989 |
| EP | 0375122 | 6/1990 |
| EP | 1177728 | 2/2002 |
| GB | 2197575 | 5/1988 |
| GB | 2250266 | 6/1992 |
| WO | WO 00/24273 | 5/2000 |
| WO | WO 00/41575 | 7/2000 |

OTHER PUBLICATIONS reflect.com, http://www.reflect.com, 1 page, (1999).

"Acumins Custom Formulated Nutritional Supplement", *Acumins, Inc.*, http://acumins.com/, 1 page, (1996).

"What's Your Blend", *Millstone*, http://www.persoanlblends.com, pp. 1-15, (1981).

Karpinski, R., "Sites Give Virtual Reps a Tray", *Internet Week*, ISSN 1096-9969, pp. 1-2, (Jan. 2000).

Google Groups, Make Your Own LC Gift Baskets, Dec. 8, 1999, Newsgroups: alt.support.diet.low-carb. http://groups.google.com.

Decareau, R.V., Microwave Foods: New Product Development, Copyright 1992, by Food & Nutrition Press, Inc., pp. 48-50.

"Jolly Time Pop-alarity Contest", from Internet website www.newstime.rway.com, Apr. 3, 2002.

Francis, Encyclopedia of Food Science and Technology, 2000, John Wiley & Sons, Inc., Second Edition, vol. 2, pp. 859-860.

Francis, Encyclopedia of Fond Science and Technology, 2000, John Wiley & Sons, Inc., Second Edition, vol. 4, pp. 2253-2254.

"Sugar Free Caramel Popcorn", Healthy Exchanges Message Boards and Online Support, from Internet website www.healthyexchanges.com, Nov. 26, 2000.

"Tidbits: How Slightly Sweet It Is!", from Internet website www.startribune.com, Feb. 2, 2002.

"Two Top Food You Miss the Most", Google Groups, Newsgroups: alt.support.die.low-carb, http://groups.google.com, Dec. 9, 1999.

"Artificial Sweetener You Can Bake With?" Google Groups, Newsgroups: misc.health.diabetes, http://groups.google.com. Jun. 6, 1999.

"Can Sucralose be Carmelized?", Google Groups, Newsgroups: alt.support.diet.low-carb, http://groups.google.com, Jan. 21, 2000.

"Sugar Alcohol??", Google Groups, Newsgroups: misc.health.diabetes, http://groups.google.com, Jan. 19, 2001.

International Food Information Counsel, "Everything You Nee to Know About Sucralose", May 1998, http://www.ific.org/publications/brochures/sucralosebroch.cfm, pp. 1-4.

* cited by examiner

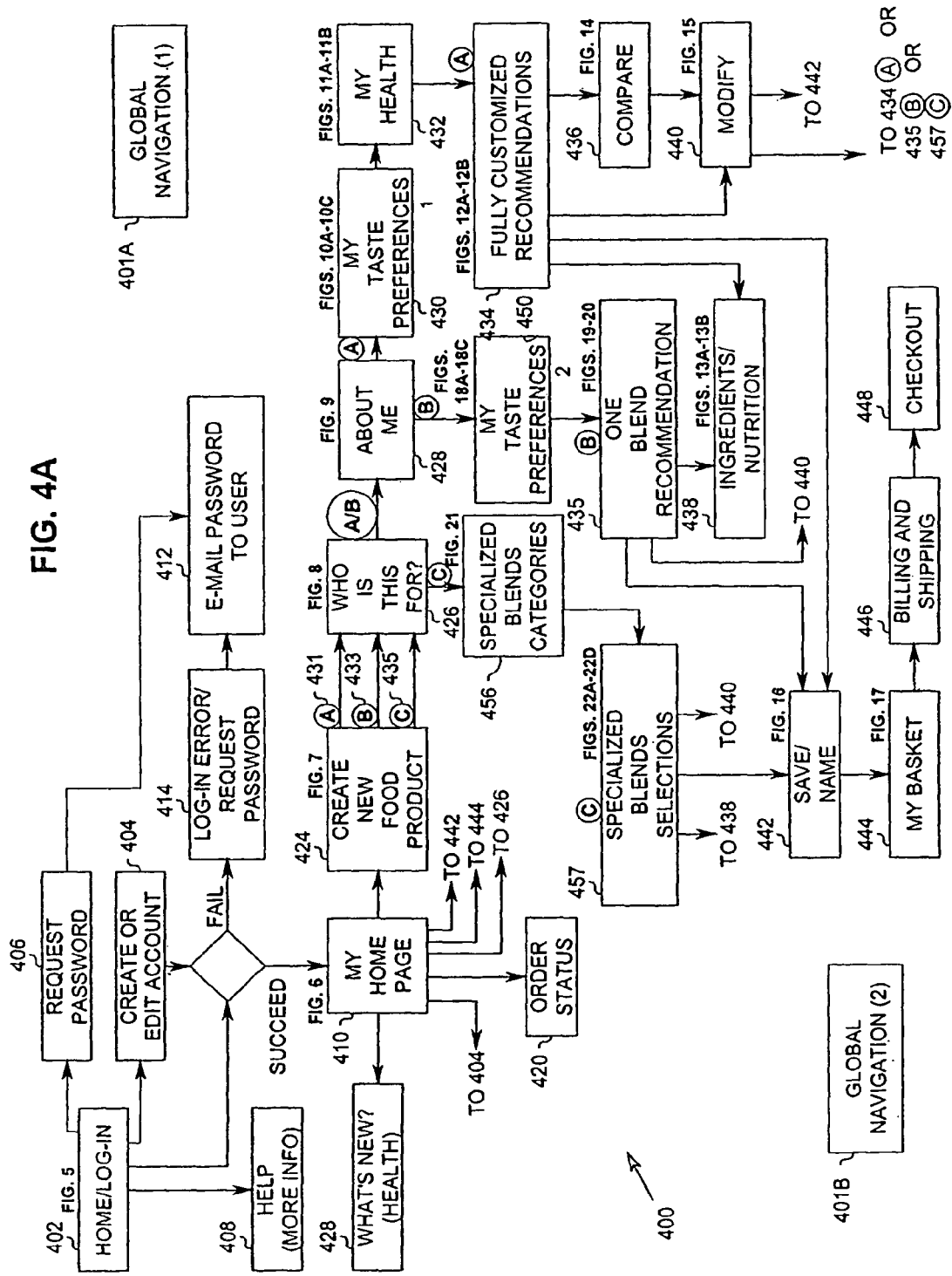

| File | Edit | View | Insert | Format | Tools | Shape | Window | Help |

*about me*      RECOMMENDATION PATH (A)
or ONE BLEND ONLY PATH (B)

903 ~ GENDER   >*Female*     905 ~ AGE    > *2-10*     > *40-55*
                 >*Male*                         > *11-17*    > *56-70*
                                              > *18-39*    > *over 70*

907 ~ DO YOU HAVE FOODS YOU ARE ALLERGIC TO OR WOULD LIKE TO AVOID? SELECT ALL THAT APPLY:

☐    No food allergies or adverse reactions    ☐    Eggs

NUTS:                              ☐    Soy

☐    Peanuts                ☐    Wheat

☐    Other Nuts*         ☐    Dairy products

*One or more of the following: Almonds, Pecans, Walnuts, Hazelnuts, Macadamia nuts

909 ~ SELECT YOUR PREFERENCE FOR SERVING SIZE:

○   Small (for small appetites)      ○   Medium (for moderate appetites)
       About 1 cup                         1 - 1 1/2 cups
       About 1 3/4 ounces              About 2 ounces
       120-180 calories                  180-250 calories ○   Large (for hearty appetites)       ○   Extra Large (for cereal lovers!)
       1 1/2 - 1 7/8 cups                 1 7/8 - 2 1/4 cups
       About 3 ounces                   Over 3 ounces
       250-320 calories                  330-400 calories

911 ~ ARE YOU ON A SPECIAL DIET? SELECT ALL THAT APPLY:

○   No special diet               ○   Diabetic

○   Vegetarian                   ○   Low cholesterol, low fat

○   Low sodium                 ○   Athlete-in-training (high carbohydrate)

○   Weight Watchers®/Jenny Craig®    ○   Atkins®

913 ~ SELECT YOUR PREFERRED PACKAGING FORM:

○   Bowl

○   Pouch

↑
428          *FIG. 9*

RECOMMENDATION PATH "A"
CEREAL FORMS (CHOOSE AS MANY AS YOU LIKE) ~ 1006

- ☐ Toasted Cinnamon Multi-Grain Squares
- ☐ Cinnamon Graham Squares
- ☐ Corn Squares
- ☐ High Fiber Bran Shreds
- ☐ Honey Nut Multi-Grain Squares
- ☐ Honey Graham Squares
- ☐ Multi-Bran Squares
- ☐ Multi-Grain Granola
- ☐ Multi-Grain Muesli
- ☐ Rice Squares
- ☐ Wheat Biscuits
- ☐ Wheat Nuggets
- ☐ Wheat Squares FRUITS - PLEASE NOTE THAT ALL FRUIT SELECTIONS ARE DRIED OR FREEZE-DRIED. (CHOOSE AS MANY AS YOU LIKE) ~ 1008

- ☐ Apple Slices
- ☐ Raisin Apple Prune Bits
- ☐ Banana Bits
- ☐ Cherry Bits
- ☐ Cinnamon Apple Slices
- ☐ Coconut Bits
- ☐ Cranberry Bits
- ☐ Golden Raisins
- ☐ Mango Bits
- ☐ Peach Bits
- ☐ Whole Cranberries
- ☐ Pineapple Bits
- ☐ Raisin Date Bits
- ☐ Raisins
- ☐ Raspberry Bits
- ☐ Strawberry Bits
- ☐ Sweetened Date Bits
- ☐ Toasted Coconut Bits
- ☐ Whole Blueberries
- ☐ Whole Cherries

*1430B*       *FIG. 10B*

| File | Edit | View | Insert | Format | Tools | Shape | Window | Help |
|------|------|------|--------|--------|-------|-------|--------|------|

*my health*    RECOMMENDATION PATH "A"
*general health concerns*         ~ 1102

PLEASE CHECK ALL THAT APPLY:

- ☐ Colon cancer
- ☐ Constipation/Desire Extra Fiber
- ☐ Diabetes
- ☐ High blood pressure
- ☐ High blood cholesterol
- ☐ Heart disease or coronary artery disease
- ☐ Arthritis
- ☐ Weight loss/weight management
- ☐ High blood cholesterol or heart disease
- ☐ Electrolyte Loss (diarrhea, athletic training, etc.)

- ☐ Energy
- ☐ Osteoporosis or bone health
- ☐ Pregnant or nursing
- ☐ Menopause
- ☐ Digestive problems
- ☐ Frequent colds or influenza
- ☐ Migraine Headaches
- ☐ Memory Loss
- ☐ Insomnia
- ☐ None of the above

*food supplements*           ~ 1104

PLEASE CHECK ALL THAT APPLY:

- ☐ Prenatal Vitamins
- ☐ Other ___ (specify) [    ]
- ☐ Herbal Supplements (specify) [    ]

- ☐ Multivitamin

| File | Edit | View | Insert | Format | Tools | Shape | Window | Help |

*my health*  RECOMMENDATION PATH "A"
*just for women* ~ 1106

| | | |
|---|---|---|
| ARE YOU CURRENTLY PREGNANT OR TRYING TO BECOME PREGNANT? | ☐ YES | ☐ NO |
| ARE YOU LACTATING? | ☐ YES | ☐ NO |
| ARE YOU EXPERIENCING ANY SYMPTOMS OF MENOPAUSE? | ☐ YES | ☐ NO |

*lifestyle* ~ 1108

| | | |
|---|---|---|
| DO YOU EXERCISE AT LEAST THREE TIMES A WEEK? | ☐ YES | ☐ NO |
| ARE YOU A SERIOUS ATHLETE | ☐ YES | ☐ NO |
| DO YOU SMOKE? | ☐ YES | ☐ NO |

*eating habits* ~ 1110

FOR EACH OF THE FOLLOWING FOODS, HOW MANY SERVINGS PER DAY DO YOU EAT? *Click here for more information to help with this section:*

| | | | |
|---|---|---|---|
| CALCIUM-RICH FOODS | ☐ 0 or 1 | ☐ 2 or 3 | ☐ 4+ |
| FRUITS | ☐ 0 or 1 | ☐ 2 or 3 | ☐ 4+ |
| VEGETABLES | ☐ 0 or 1 | ☐ 2 or 3 | ☐ 4+ |
| MEAT AND EGGS | ☐ 0 or 1 | ☐ 2 or 3 | ☐ 4+ |
| CEREALS, BREADS AND GRAINS | ☐ 0 or 1 | ☐ 2 or 3 | ☐ 4+ |
| SWEETS | ☐ 0 or 1 | ☐ 2 or 3 | ☐ 4+ |

*RECOMMENDATION PATH "A"*

*recommendations (continued)*

CUSTOM BLEND THREE ~1206

Cinnamon Graham Squares, Banana Nut Clusters, Chopped Hazelnuts, Sliced Almonds

Consumers with food allergies:
Contains WHEAT, DAIRY, ALMONDS, HAZELNUTS ingredients Nutrition Highlights

| Vitamin E | Vitamin C | Calcium | Fiber | Folic Acid | Soy Protein |
|---|---|---|---|---|---|
| 6 % | 10 % | 15 % | 3 g | 30 % | 0 g |
| Daily Value | Daily Value | Daily Value | | Daily Value | |

<u>Save This Cereal (and add to My Basket)</u>   <u>Detailed Ingredients/Nutrition Panel</u>   <u>Modify Cereal</u>   <u>Pricing</u>

Some of our fruits may contain sulfites. If concerned, please click on "Complete Nutrition" for the blend you select.

1236 ~ > *<u>Compare Cereals' Nutrition</u>*
1234 ~ > *<u>See More Choices</u>*
1210 ~ > *<u>Start Over</u>*

(Selecting "Start Over" will take you back to "Create New Food Product" page (410)

*FIG. 14* compare RECOMMENDATION PATH "A" or SPECIALIZED BLENDS PATH "C"

*PATHS "A", "B" or "C"* my basket

YOUR ORDER ~1702

| CEREAL DESCRIPTION | PACKAGING TYPE | QUANTITY | EACH | TOTAL |
|---|---|---|---|---|
| Rocky Road (1.5 cup servings) | Bowl | 7 servings | $1.09 | $7.63 |

>> *Click Here For Larger* ~1704
*Portions (2 Cups) For $0.25 Extra*

Subtotal
Shipping
Total

YOUR ADDRESS INFORMATION ~1706
Billing Address:
Shipping Address:

PAYMENT INFORMATION ~1708
Saved Credit Card
Use a Different Credit Card >> *(ENTER INFORMATION HERE)*

*Review Privacy Policy* ~1710

> *Submit Order* ~1712
> *Start Over* ~1714

| File | Edit | View | Insert | Format | Tools | Shape | Window | Help |

*My taste preferences$_2$*  ONE BLEND ONLY PATH "B"

OTHER CEREAL FORMS: ~ *1808*

- ☐ Toasted Cinnamon Multi-Grain Squares
- ☐ Cinnamon Graham Squares
- ☐ Corn Squares
- ☐ *Wheat* Squares
- ☐ Honey Nut Multi-Grain Squares
- ☐ Honey Graham Squares
- ☐ Multi-Bran Squares
- ☐ Rice Squares
- ☐ Multi-Grain Muesli
- ☐ Multi-Grain Granola
- ☐ Wheat Biscuits
- ☐ Wheat Nuggets
- ☐ High Fiber Bran Shreds

CLUSTERS/ADD-INS: ~*1810*

- ☐ Banana Nut Clusters
- ☐ Maple Nut Clusters
- ☐ Chocolate Flavored Marshmallow Bits
- ☐ Dinosaur Shaped Rice Puffs
- ☐ Oat Clusters
- ☐ Sweetened Nut Clusters
- ☐ Marshmallow Bits

*my taste preferences*₂  ONE BLEND ONLY PATH "B"

NUTS: ~ 1812

- ☐ ALMOND COATED RAISINS
- ☐ ALMOND SLICES
- ☐ Chopped Hazelnuts
- ☐ Chopped Pecans
- ☐ Chopped Roasted Macadamia Nuts
- ☐ Chopped Walnuts
- ☐ Dried Fruit and Nut Blend
- ☐ Sugar Coated Sliced Almonds
- ☐ Honey Roasted Soy Nuts
- ☐ Roasted Soy Nuts FRUITS - PLEASE NOTE THAT ALL FRUIT SELECTIONS ARE DRIED OR FREEZE-DRIED:  ~ 1814

- ☐ BANANA BITS
- ☐ CHERRY BITS
- ☐ RAISIN APPLE PRUNE BITS
- ☐ COCONUT BITS
- ☐ CRANBERRY BITS
- ☐ GOLDEN RAISINS
- ☐ WHOLE BLUEBERRIES
- ☐ WHOLE CHERRIES
- ☐ SWEETENED DATE BITS
- ☐ WHOLE CRANBERRIES
- ☐ RAISIN DATE BITS
- ☐ RAISINS
- ☐ Apple Slices
- ☐ Cinnamon Apple Slices
- ☐ Raspberry Bits
- ☐ Toasted Coconut Bits
- ☐ Mango Bits
- ☐ Peach Bits
- ☐ Pineapple Bits
- ☐ Strawberry Bits >CLICK HERE TO MODIFY YOUR FAVORITE CEREAL!!  ~ 1811
(How about Honey Nut Cheerios® with cranberries!)

ONE BLEND ONLY PATH "B" – MODIFY YOUR FAVORITE CEREAL CATEGORY

| Cereals (Choose 1, 2, or 3) | | Vitamins & Minerals (Choose 1) |
|---|---|---|
| • Cheerios®<br>• Corn Chex®<br>• Rice Chex®<br>• Wheat Chex®<br>• Cinnamon Toast®<br>• Cocoa Puffs®<br>• Corn Flakes® | • Fiber 1®<br>• Sugar Frosted Corn Flakes®<br>• Granola®<br>• Honey Nut Cheerios®<br>• Honey Nut Chex®<br>• Golden Grahams®<br>• Kix® | • Lucky Charms®<br>• Raisin Bran®<br>• Crispy Rice®<br>• Shredded Wheat®<br>• Total®<br>• Trix®<br>• Wheaties® | • Standard vitamins & minerals<br>• Personalized blend*<br><br>Other Nutrients (0, 1, or 2)<br><br>• Fiber (bran) clusters<br>• Soy protein clusters |
| Nuts (Choose 0, 1, or 2) | Fruits (Choose 0, 1, or 2) | Sweet Stuff (Choose 0, 1, or 2) | |
| • Almonds<br>• Hazelnuts<br>• Honey nut clusters<br>• Macadamia nuts<br>• Pecans<br>• Peanuts<br>• Raisin nuts<br>• Walnuts | • Apple chunks<br>• Apricots<br>• Bananas<br>• Blueberries<br>• Sweet cranberries<br>• Dates<br>• Peaches<br>• Raspberries<br>• Raisins<br>• Golden Raisins<br>• Strawberries<br>• Tropical (pineapple, papaya, and mango) | • Chocolate chunks (dark)<br>• Chocolate chunks (milk)<br>• Chocolate chunks (white)<br>• Chocolate & peanut butter<br>• Chocolate coated peanuts<br>• Chocolate coated raisins<br>• Coconut (shredded)<br>• Malted milk balls<br>• Marshmallow bits<br>• Yogurt chips - vanilla<br>• Yogurt chips - blueberry<br>• Yogurt chips - strawberry | Current Price<br><br>$1.00<br><br>Per Single-Serve Bowl<br><br>■ *Clear*<br>■ *Click here to save this combination*<br>■ *Click here to create another combination* |

1816

\* first you must complete our health and nutrition survey

*alternate modify option*     FIG. 20

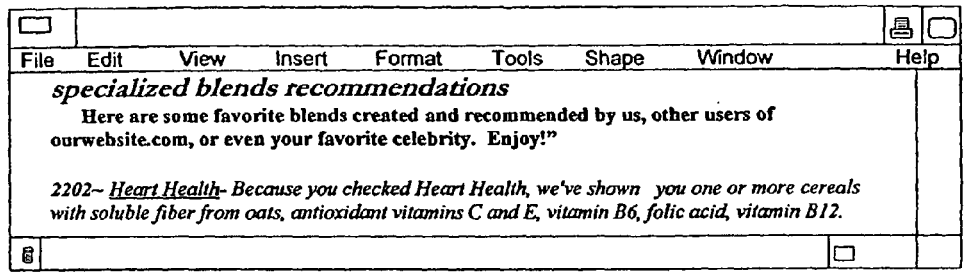
457A  FIG. 22A
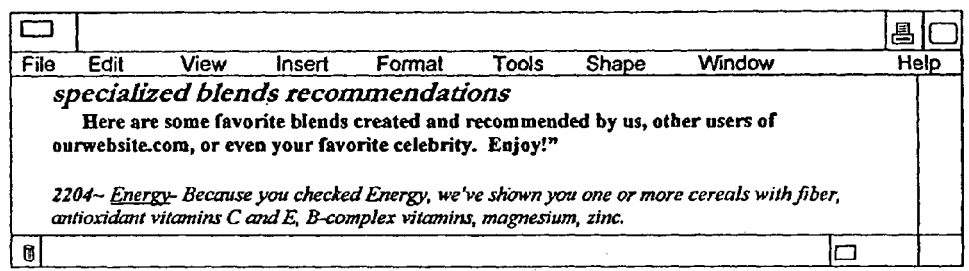
457B  FIG. 22B
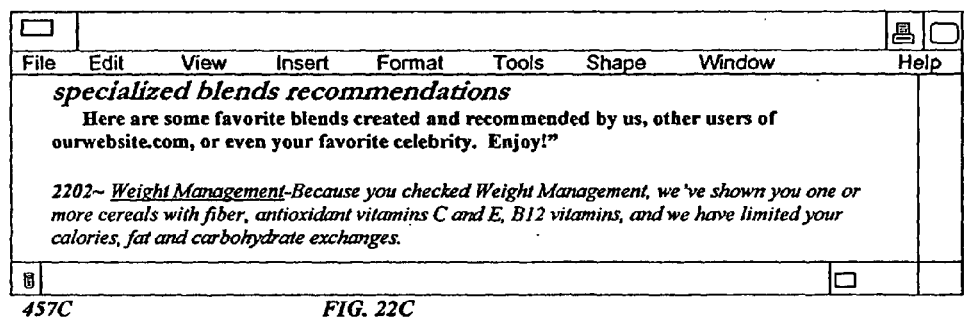
457C  FIG. 22C
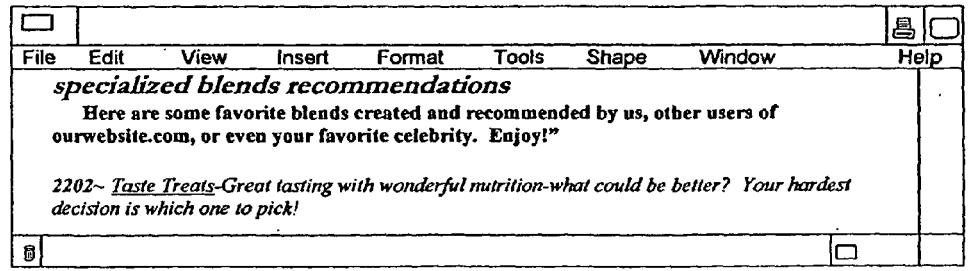
457D  FIG. 22D

~2302

~2304

~2306

CUSTOMIZED FOOD SELECTION, ORDERING AND DISTRIBUTION SYSTEM AND METHOD

CROSS-REFERENCE TO RELATED APPLICATIONS

This application represents a continuation of U.S. application Ser. No. 09/780,273, filed Feb. 9, 2001, now abandoned, which claims the benefit of U.S. Provisional Application Ser. No. 60/181,282, filed on Feb. 9, 2000, as well as a continuation of U.S. application Ser. No. 09/699,622, filed on Oct. 29, 2000, abandoned.

CROSS REFERENCES

This Application is also related to a U.S. patent application entitled, "Nutrient Clusters for Food Products and Methods of Preparation," Ser. No. 09/596,543, filed on Jun. 19, 2000, which is herein incorporated by reference in its entirety.

This Application is also related to a U.S. patent application entitled, "Food Distribution, Preparation and Consumption System," Ser. No. 09/596,275 filed on Jun. 16, 2000, which is herein incorporated by reference in its entirety.

This Application is also related to a U.S. patent application entitled, "Production of Oil Encapsulating Minerals and Vitamins in a Glassy Matrix," Ser. No. 09/595,121 filed on Jun. 16, 2000, which is herein incorporated by reference in its entirety.

This Application is also related to a U.S. patent application entitled, "Oligosaccharide Encapsulated Mineral and Vitamin Ingredients," Ser. No. 09/595,244 filed on Jun. 16, 2000, which is herein incorporated by reference in its entirety.

FIELD

The present invention relates to systems and methods of ordering and distributing food, and in particular to a customized food selection, ordering and distribution system and method.

BACKGROUND

Consumers are experiencing an ever-increasing choice in the manner in which to purchase consumer products. In addition to the traditional telephone mail order shopping, Internet-based commerce, i.e., e-commerce, now offers the convenience of shopping from home. On-line websites selling consumer goods typically offer a range of sizes, colors, models, and so forth, from which the consumer can select. However, in most instances, the provider is targeting the broadest possible group of consumers. Such mass marketing typically limits the ability of the consumer to purchase products that are particularly suited for his or her needs.

Within the food industry, conventional mass marketing results in products having generic ingredients tied to a particular product or form, such as ready-to-eat (RTE) cereal and snack products. However, as consumers grow increasingly aware of their own health concerns, and the role food can play in impacting these conditions, many are limiting or avoiding foods that contain excess fats, sugars, allergens and so forth, which can negatively impact their health. This often results in limited loyalty to any particular brand of cereal or snack product, likely because no one brand is seen as doing a superior job of meeting a consumer's needs over another. For example, even though there are over 300 RTE cereal stock keeping units (SKU) in the American grocery trade, no one SKU has greater than approximately five (5)% consumer share.

In addition to health concerns, consumers are also developing increasingly sophisticated tastes. The coffee industry, for example, has experienced tremendous growth recently as consumers have developed a taste for specialty coffees.

Meeting the diverse health and taste needs of individual consumers is simply not possible with conventional mass marketing. Traditional retailing further prevents the food industry from meeting these needs by limiting the number of SKU's carried by retailers, due, in many cases, to limited shelf space. Moreover, the current and well-established paradigm of ready-to-eat cereal and snack manufacturing and distribution has had the effect of directing attention away from considering alternative or different approaches in this area. What is needed, therefore, is a system and method of providing food products that can meet the varied needs of each individual consumer.

SUMMARY

A computer-implemented method for selecting and ordering a customized food product is described. The method comprises viewing a list of choices designed to allow a consumer to create a customized food product; making a selection from the list, the list having choices selected from the group consisting of customized food ingredient choices, customized food product choices and customized food category choices, wherein the selection is determinative of the customized food product ordered; and transmitting the selection wherein the customized food product is designed.

In one embodiment, a computer-implemented method for selecting, ordering and distributing customized food products is disclosed comprising viewing a list of additives for creating a customized food product, selecting one or more additives from the list of additives to create the customized food product, and transmitting a request to purchase the customized food product, which is then distributed to the consumer. In one embodiment, the customized food product contains a cereal base or a half-product pellet. In one embodiment, any suitable type of display device, such as a computer, is used to view, select and transmit information. In another embodiment the list provided also identifies features of various customized combinations.

In one embodiment, the consumer designs or creates his or her own customized food product, such as a cereal or snack product. In another embodiment, the consumer customizes known products as to quantity and type of various additives. In yet another embodiment, the consumer is given any number of choices, such as a choice between designing a food product by selecting from an ingredient list, selecting a food product custom-designed for the consumer based on responses in a health and nutrition survey, selecting from among previously-created custom food products, customizing known food products, and so forth. Such choices may or may not include options to further modify and customize.

In one embodiment, individual consumers log onto a website to participate in an on-line survey to evaluate their current health and lifestyle, as well as to determine their preferences in nutrition and taste. Questions concerning taste can be used to determine cereal preferences as to grains, flavors, sweetness, nutrition, serving size, packaging, forms, particulates, types (e.g., hot or RTE cold). In response to the information provided by the consumer, the manufacturer can ask additional questions and/or provide particular choices. In this way, the selection process is interactive and can also be iterative.

In one embodiment, the consumer designs his or her own food product by selecting the exact amount and type of each ingredient desired. In essence, a nearly infinite amount of customized food products are now available to the consumer. In another embodiment, the consumer may choose not to complete the survey, but can customize known products with desired additives or ingredients, including vitamins, minerals, herbs, flavors, nutraceuticals, particulates such as fruits and nuts, and so forth. In one embodiment, consumers are invited to select from two to three food products that most closely match their particular needs. In another embodiment, four to one thousand or more choices are presented.

The resulting product can be shipped through various channels of trade in consumer-sized packages to an intermediary or directly to the end user. Packages can include a conventional consumer-sized box, individual pouches, covered bowls or even beverage-type containers. The resulting product is precisely suited to meet the needs of a specific consumer, particularly in the areas of health, taste and texture.

In one embodiment, a customized food product is designed by selecting from among ingredients, categories or previously-designed food products wherein a consumer communicates taste preferences to a merchant, wherein the merchant produces a unique product for the consumer.

In an alternate embodiment, puffable half-product pellets, together with any other selected additives, are shipped to the consumer as the customized food product. Puffable half-products can be expanded or puffed to produce a variety of foods, including, but not limited to, cereals, cereal-based snacks and beverages, through exposure to a suitable energy source. The package can also include savory toppings, and instructions on how to prepare the half-products, apply the toppings, and so forth.

By communicating with a manufacturer as to personal needs and desires pertaining to health, activity level, organoleptic preferences and so forth, consumers can now, for the first time, develop and order a customized food product to suit their particular tastes using real-time interactive communication These and other features, aspects and advantages of the present invention will become better understood with regard to the following description, appended claims and accompanying drawings.

BRIEF DESCRIPTION OF THE DRAWINGS

FIG. 4A is an overview map of a sample Web site for one embodiment of a customized food selection and ordering system.

FIG. 9 is a sample Web page showing one embodiment of an "about me" page that is viewed on Paths A or B.

FIGS. 10A-10C are sample Web pages showing one embodiment of a "my taste preferences," page viewed on Path A.

FIGS. 11A-11B are sample Web pages showing one embodiment of a "my health" page viewed on Path A.

FIGS. 12A-12B are sample Web pages showing one embodiment of a "fully customized recommendations" page viewed on Path A.

FIG. 14 is a sample Web page showing one embodiment of a "compare" page viewed on Paths A or C.

FIG. 17 is a sample Web page showing one embodiment of a "my basket" page viewed on Paths A, B or C.

FIG. 18A-18C are sample Web pages showing one embodiment of a "my taste preferences$_2$" page viewed on Path B.

FIG. 20 is a sample Web page showing one embodiment of an "alternate modify" page viewed on Path B.

FIGS. 22A-22D are sample Web pages showing embodiments of "specialized blends recommendations" pages viewed on Path C.

DETAILED DESCRIPTION OF INVENTION

Figure 1:
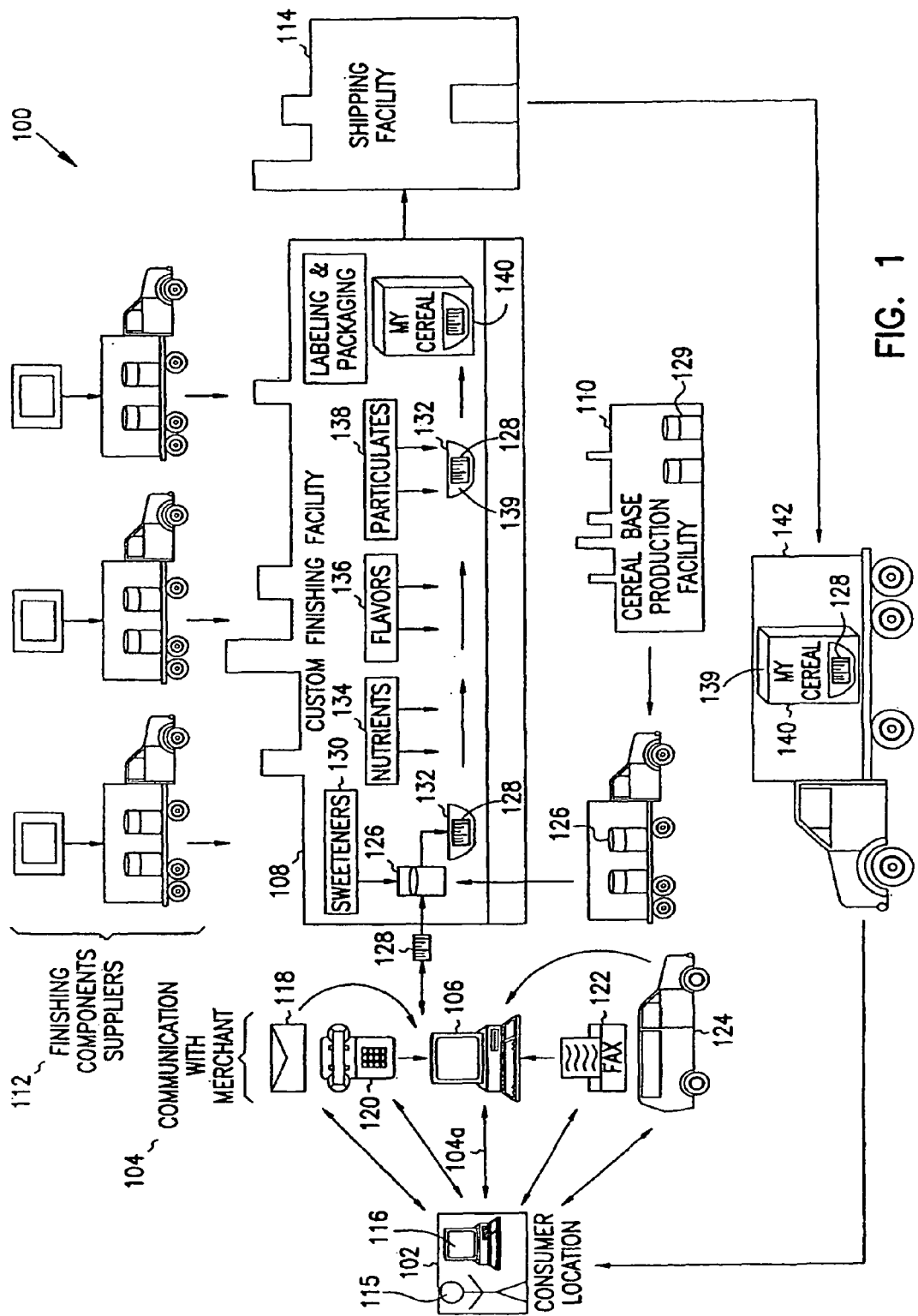
FIG. 1 is a simplified schematic diagram of one embodiment of a customized food selection, ordering and distribution system.

In the following detailed description, reference is made to the accompanying drawings that form a part hereof, and in which is shown by way of illustration, specific embodiments in which the invention may be practiced. These embodiments are described in sufficient detail to enable those skilled in the art to practice the invention, and it is to be understood that other embodiments may be utilized. It is also to be understood that structural, procedural and system changes may be made without departing from the spirit and scope of the present invention. The following detailed description is, therefore, not to be taken in a limiting sense, and the scope of the present invention is defined by the appended claims and their equivalents.

A system and method for selecting, ordering and distributing customized food products is disclosed. Various terms used throughout the specification are defined in a first section. A second section provides an overview of one embodiment of a customized ordering and distribution system. A third section provides a system-level overview of the invention. A fourth section provides methods of using example embodiments of the invention. A fifth section provides a high level overview of a particular implementation of a user interface. A sixth section provides details of the particular implementation through a series of Web pages. Finally, a conclusion to the detailed description is provided.

Definitions

As used herein, the term "additive" is intended to encompass any type of food ingredient added to the food product at any time during manufacturing. A "topping" is one type of additive which typically stays on "top" or exterior surface of the cereal base (or a half-product pellet), although a "topping" can also be applied as a "coating" such that it adheres to some or all of the cereal base (or half-product pellet), with or without the assistance of a carrier substance. Liquids in any form are also considered to be additives. Embodiments that discuss the use of "toppings" can also include the use of any type of "additive." Additives can also be considered to include "color agents" as defined below. Additives also include non-nutritive (non-carbohydrate) high-potency sweeteners (such as aspartame, acesulfame K, and saccharin) as well as carbohydrate-based sweeteners, and any other "carbohydrate" as defined below. Additives further include acids (such as fruit-flavor enhancing edible organic acids, such as citric, malic and/or succinic acid), bases, salts, buffering systems, chelating agents, antioxidants, antimicrobial agents, gases/propellants, and so forth. Additives further include nutrient and health additives such as vitamins, minerals, encapsulated biologically active components, nutraceuticals (defined below), dietary supplements, anti-oxidants, fibers, fructo-oligo saccharides such as inulin, calcium materials such as calcium carbonate and calcium phosphate salts, probiotic bacteria sprinkles (e.g., lactobacillus or acidophilus), energy additives, protein powders, powdered milk fractions, protein or satiety additives, herbs, aromatic substances, and other similar health-enhancing additives. Additives can also include "particulates" as defined herein.

The term "ingredient" as used herein, is the smallest, non-divisible part of a cereal or other food product. For example, a corn flake or a nut cluster is an ingredient. Bases, particulates and clusters are all ingredients.

The term "particulates" is generally used to refer to non-grain items. The term "particulates" as used herein includes, but is not limited to, added particles such as dried whole fruits (e.g., raisins, dates, blueberries, peaches, raspberries, apricots, strawberries, cranberries, tropical [e.g., pineapple, papaya and mango], etc.), fruit parts (e.g., banana chips, apple chunks, etc.), dried fruit products (whether or not infused with sugar, glycerol, etc.), marshmallows, marshmallow bits (dried or moist), malted milk balls, chocolate and peanut butter chunks, chocolate (e.g., milk chocolate, dark chocolate, white chocolate, etc.), chocolate products (e.g., chocolate-coated raisins, chocolate-coated peanuts, etc.), nuts (e.g., walnuts, raisin nuts, pecans, peanuts, almonds, hazel nuts, macadamia nuts, etc.), shredded coconut, yogurt chips (e.g., vanilla, blueberry, strawberry), clusters of particulates (e.g., honey nut clusters), and so forth.

The term "cluster" as used herein generally refers to small grain/cereal pieces aggregated together with a sugar-based matrix typically about fifty to sixty-five percent (50-65%) grains and thirty to fifty percent (30-50%) sugar-based matrix. Occasionally other items like diced nuts, etc. are incorporated into the cluster aggregate. Nutritionally fortified clusters that are particularly suited for use herein are described in more detail in a U.S. patent application entitled "Nutrient Clusters for Food Products and Methods of Preparation" Ser. No. 09/596,543 filed on Jun. 19, 2000, which is herein incorporated by reference. Clusters are generally grouped into two categories: 1) nutritional clusters, as defined by the desired macro and/or micronutrients (such as soy protein, oat bran and calcium); and 2) taste clusters. The taste clusters are not limited to any type of cereal ingredient (aggregate) used to deliver vitamin and nutrient fortification.

Examples of nutritional clusters include, but are not limited to, the following: soy protein clusters, enriched soy protein clusters, enriched soy protein clusters with iron, oat bran clusters, enriched oat bran clusters, enriched oat bran clusters with iron, calcium clusters, enriched calcium clusters, enriched calcium clusters with iron, and enriched almond-coated raisins (particulate—i.e., non-grain, non-aggregate), and so forth. However, nutritional clusters are not limited to the purpose of delivering vitamins, minerals and other nutrients such as fiber, protein, phytonutrients, or nutritionally selected triglycerides or factions thereof, e.g., having particular fatty acids profiles.

Clusters may also be used to provide taste variety in a food product. Examples of such taste clusters include, but are not limited to, banana nut clusters, blueberry-flavored clusters, chocolate-flavored almond clusters, maple nut clusters, honey nut clusters, oat bran clusters, milk chocolate-flavored clusters and the like (these types of ingredients are widely used in the industry as a type of particulate added to other cereal ingredients to provide color, flavor, etc.).

The terms "cereal base" or "base" include a variety of "forms," even if only a few specific forms, such as a RTE cereal or snack, are listed with respect to a particular embodiment. Specifically, the term "cereal base" or "base" is considered to include products that contain a food product in either a whole, partially ground or finely ground form. A cereal base can also be a "sheet"-type product made from a "sheet"-shaped half-product, i.e., having opposed major faces, including any type of three-dimensionally shaped puffed-food product, and can include pastries, waffles, pancakes, and so forth. In an example embodiment in which the food product is a cereal, the base is an ingredient that makes up a significant portion of the overall volume of the cereal.

The cereal base can also be any type of "pressed" product such as a granola bar. In the case of other products such as a beverage, the base may be the sweetened, carbonated water to which various flavors, colors, health additives and particulates may be added. In the case of yogurt, the base may be the basic fermented milk product to which various sweeteners, flavors and particulates may be added.

Examples of cereal bases or bases include, flakes, biscuits, sheds, or puffed pieces, but are not limited to, apple-cinnamon oat rings, multi-grain flakes, lightly-sweetened corn flakes, multi-grain flakes, oat rings, cinnamon corn stars, cinnamon graham squares, cocoa corn puffs, corn squares, corn flakes, wheat biscuits, cocoa corn flakes, multi-grain flakes, sweetened wheat biscuits, multi grain muesli, toasted cinnamon multi-grain squares, high-fiber bran shreds, maple-flavored corn puffs, frosted oat rings, frosted corn flakes, fruit-flavored corn rings, honey graham squares, multi-grain granola, honey nut oat rings, honey nut multi-grain squares, corn puffs, sweetened oat puffs, multi-bran squares, multi-grain rings, oatmeal flakes, peanut butter and cocoa corn puffs, rice squares, bran flakes, oat and soy rings, sweetened soy flakes, soy flakes, sweetened oat & soy rings, whole-grain wheat flakes, corn flakes, bran flakes, natural and artificial fruit-flavored corn puffs, whole-grain wheat flakes, wheat squares, natural and artificial fruit-flavored corn rings, sweetened corn puffs, cocoa rice puffs, rice or wheat or corn puffs, natural and artificial fruit-flavored rice puffs, frosted corn flakes, sweetened wheat puffs, corn flakes, wheat nuggets, frosted wheat flakes, and the like.

As used herein, the term "half-product pellets" means grain-based products that are generally fabricated from farinaceous cooked or partially-cooked cereal doughs. These half-product pellets may take the form, for example, of cereal pellets or snack pellets, such as pasta pellets. Cereal pellets are generally smaller in size as compared with snack pellets. The term "pellet," when used without qualification, refers to a puffable piece of a gelatinized dough product (i.e., a half-product) which is at least partially gelatinized, and which is roughly rounded in shape. The term "pellet" is intended to broadly encompass "flavor-integrated" pellets, which are pellets having flavorings and seasonings added into the dough, "flavor-coated" pellets, which are pellets having flavorings and seasonings added as a coating, or "regular" pellets, which are pellets having no additional flavorings added. Flavor-integrated pellets and flavor-coated pellets are both considered to be "pre-flavored."

The term "customized food product" as used herein means a food product that contains any type of customized food ingredients, such as a cereal base (or even a half-product pellet that still requires puffing) together with selected additives designed to meet the needs of a particular consumer. This includes a customized food product which can be served hot, warm, frozen, chilled or at room temperature. A customized food product can also be used as a topping, as an additional ingredient which is either admixed or blended into any other food, including but not limited to, a liquid or semi-liquid, which can be frozen, chilled, warm, hot or at room temperature, i.e., at any desired temperature. A customized food product includes any type of snack, e.g., snack bar, snack chip, pretzel, snack mix, power bars, granola mixes, popcorn snacks, etc. A customized food product can also be any type of portable food (e.g., snack bar), as well as a dessert or meal, including any type of baked goods, fried foods, grilled food and cooked food. In addition to cereals and snacks, examples of customized food products include any type of cereal-based or non-cereal based hot or cold beverages, including but not limited to energy beverages, nutraceutical beverages, teas or tea beverages (e.g., chai), blended beverages (e.g., coffee drinks, alcoholic drinks, etc.), juices and juice blends (i.e., juice/dairy, juice/soda, chilled fruit smoothies), grain-based beverages (i.e., soy milks, oat milks, nut milks, e.g., almond milk, etc.), further including grain/dairy, grain/juice, grain/dairy juice blends), dairy based (i.e., yogurt beverages, flavored milks, etc.), fermented beverages (i.e., dairy based, grain-based, e.g., beer, etc., with or without various pre- and pro-biotic components), fermented solids (e.g., breads, cheeses, with or without various pre-and pro-biotic components), yogurts, fruit-blended foods, fruit/nut blends, gelatins, ice creams, sherbets, flavored frozen bars, frozen novelty treats, hot cereals containing finely ground puffed pieces and cereal-based snacks of varying sizes, and so forth.

Customized food products also include any type of mixes, e.g., dessert mixes, bread mixes, and so forth, as well as pasta blends, meal mixes, dinner mixes (e.g., pasta with seasonings for meats and further including meats, such as freeze-dried meats), side dish mixes, and so forth. Customized food products also include any type of fruits or vegetables as well as fruit or vegetable blends, fruit or vegetable/sauce blends, salad blends, e.g., custom blends of greens and vegetables with custom selected dressings and condiments. Customized food products can also include meats, poultry, beans, pasta, sauces, i.e., virtually any type of food product to which customized food ingredients can be added or which can be created from customized blends of ingredients. This further includes customized food products in which any type of additive has been applied as a coating, topping, glazing, an additional ingredient, and so forth. A customized food product can also refer to any type of customized animal food, such as for pets, livestock, and so forth.

The term "nutraceutical" as used herein refers to edible materials having, or believed to have, medicinal or even therapeutic effects. Nutraceuticals include the tocopherols, B vitamins, ginseng and other herbs, wheat grass and barley grass and extracts of the grasses, soy-based estrogen analogs or soy isoflavones, chromium pico lineate, red rice yeast, minerals, St. John's wort, chitosann, and so on.

The term "flavor," "flavor agent" or "flavoring" as used herein refers to an organoleptic agent in the form of an emulsion, concentrate, aqueous- or oil-soluble liquid or a dry powder, as well as any type of chunky piece or pieces that may be added to a mixture at any time in the process or mixtures thereof, such as a liquid and powder slurry. Flavorings can also be considered additives and can include nuts, nut pieces, fresh fruits, dried fruits, fruit products, candies, marshmallows, dried marshmallow pieces known as "marbits," chocolates and chocolate products, and so forth. Flavorings further include any fruit flavors such as berry flavors, apple, cherry, plum, raisin, banana, pear, peach, figs, dates and so on. Flavorings may also include fats, salts, honeys, cheeses, frosting, powdered food products, sugar, sugar substitutes, gelatins and spices. Flavorings may also include colorings as well as any nut flavors as well as any sweet flavors such as chocolate, vanilla, caramel, butterscotch, lemon, malt, cinnamon, graham, coconut flavors, mint and so on. Flavorings additionally include any savory flavors such as all meat, game, fowl, fish, dairy, barbecue, smoke, pepper, spicy and vegetable flavors.

The term "sugar" as used herein refers to substantially all sugars and sugar substitutes, including any monosaccharide such as glucose or fructose, disaccharides such as lactose, sucrose or maltose, polysaccharides such as starch, oligosaccharide, sugar alcohols, or other carbohydrate forms such as gums that are starch based, vegetable based or seaweed based (beta glucan, psyllium).

The term "sweetener" as used herein refers to essentially all sweeteners that are "carbohydrate"-based, as defined above under "carbohydrate" and further includes sweeteners that are "non-nutritive" as defined above under "additive."

The term "fat" as used herein is synonymous with the term "lipid" and refers to substantially all fats and fat mimics (e.g., sucrose polyesters), including any animal (e.g., dairy, marine, etc.) or vegetable fat in solid or liquid form.

The term "color" or "coloring agent" as used herein refers to natural or uncertified colors from natural sources or certified colors for the effect of color. In one embodiment, the colors include dyes, certified aluminum lakes or colors derived from a natural source. Coloring agents may also be water-based or oil-based or dry. Coloring agents may be primary colors, blends of colors or discrete mixtures of colors, such as confetti.

The term "carbohydrate" refers to any organic compound (and its derivatives and analogs) containing carbon, hydrogen, and oxygen as well as a saccharose group, as is known in the art. As such, carbohydrates include mono-, di-, oligo-, and polysaccharides and their derivatives (such as sugar alcohols and sugar esters). Carbohydrates may impart sweetness (as in the case of sugar) or non-sweetness (as in the case of starch). Examples of sweet and non-sweet carbohydrates include fructose, sucrose, lactose, maltose, galactose, xylose, dextrose, maltose, trehalose, raffinose, stachyose, corn syrups, honey, molasses, malt syrups, corn syrup solids, maltodextrins, starches, pectins, gums, carageenan, and inulin.

The term "puffed" is used herein to collectively refer to a variety of finished forms, including, but not limited to, puffs, flakes, shreds, finely ground particles and so forth. "Puffed" pieces generally refer to cereal pieces having a specific density typically ranging from about 0.15 to 0.3 g/cc. Quantities of pieces of such puffed pieces will have even lower bulk densities (e.g., ten (10) oz. per 200 cu in.). Such puffed pieces are distinguished from "unpuffed" or "half-product" pieces having little or no degree of expansion and generally characterized by specific densities of about 0.3 to 0.8 g/cc. Pieces can be two dimensional of either regular shape (round, oval, square, rectangular) or irregular shape (flake, having a periphery forming an outline of a figurine). Such pieces can have opposed major sides and a thickness of less than about (4) mm, which may be flat, curved or curvilinear, or three-dimensional (3D) (i.e., having an aspect ratio of any two dimensions ranging from 1:1 to 10:1). 3D shapes can be simple (e.g., a disk or a sphere) or complex such as an airplane or figurine, or spiral.

As used herein, the term "puffed" or "expanding" refers to a drying process in which the half-product is dried rapidly enough to cause the half-product to expand or puff. Puffing occurs when bound moisture in a liquid state is converted to a vapor phase and "suddenly" released during exposure to a suitable energy source, such as thermal or microwave energy. If the half-product is dried too slowly, it remains hard, rather than softening and puffing. This is in contrast to "popping" or "exploding" which occurs when popcorn is popped. This is also in contrast to "cooking," which is defined herein as the first heat or mechanical treatment that a mixture receives which essentially forms it into a dough. It is this dough, i.e., a processed grain-based unexpanded food product, which is then fabricated into the various half-products described above. (Some of these fabrication processes, such as the forming and flaking mill, as well as other processes further downstream, such as gun puffing, and so forth, can cause the starch in the dough to become gelatinized. As a result, many in the industry refer to the pre-formed dough as only "partially" cooked). It should be noted that the process of "puffing" as described herein, does not cause the starch to become gelatinized. "Puffing" is further distinguished from "reheating" of a finished puffed RTE cereal or snack piece that has a lower moisture content and density, such as about one (1) to about five (5)% moisture and about 0.02 to about 0.7 g/cc, respectively. Such reheating of a finished product would likely be unsuccessful in that it may burn, scorch and/or char the pieces, not generate the fresh flavor, toughen the texture rather than soften the piece, and so forth. "Puffing" is also distinguishable from the gradual expansion of a food product due to an uptake of liquid in the absence of applied energy, which is not a "cooking" process, per se. This includes, but is not limited to, the "soaking" up of a liquid, such as milk, by a conventional cereal product, and so forth. It is important to note, however, that the food products of the present invention can be puffed in the presence of a liquid, such as oil, if desired.

As used herein, the term "nutritional profile" refers to the foods/nutrients that an individual has consumer, i.e., an evaluation or analysis of a consumer's nutritional is intake. This can be in the form of a dietary journal, for example, in which a person notes what foods they have eaten, how much of that food they have eaten, when it has been eaten, and so forth.

As used herein, the term "health profile" refers to the overall health state or condition of an individual, including physical activity, disease state, environmental stress, genetic predisposition to disease, and so forth.

As used herein, the term "interactive" refers to communication between two or more entities. Interaction can occur between a human and a machine, between humans, between machines, and so forth. Interactive computer programs require input from humans in the form of data input or commands, as compared to compilers or batch programs, which do not require input. Similarly, interactive food purchasing refers to a purchase in which a purchaser has provided some input to the merchant, which has the effect of customizing the food product or creating a "new" or novel customized food product. This input can be as limited as selecting a particular ingredient to add to a conventional food product or as involved as completing a survey for the merchant, with the merchant, in response to the survey, providing comments and/or food product suggestions customized for that purchaser through one or more iterative cycles of interaction, whether practiced contemporaneously or over time through one or more purchase cycles. This is in contrast to purchasing a food product "as is" which has been mass marketed for a broad range of consumers. This is also in contrast to a computer program, such as a Web-based computer program having a user interface, that directs a consumer to one or more 'off-the-shelf' products that are pre-existing, i.e., a portfolio of products.

The term "real-time" or "real-time interaction" means that a response to an input is "current" as opposed to "delayed." A response in "real-time" typically occurs prior to additional input being sent, similar to a conversation in which each party takes turns speaking. "Real-time" can also refer to a system that provides a response to an external event within a given time period, i.e., such as satisfying a customer need. As used herein, "real-time" information-processing interaction refers to a reasonable amount of time given user set-up and bandwidth, i.e., a response occurring as soon as possible for a given workload. In terms of "delivery time," a delivery that occurs in "real-time" refers to delivery of a customized food product to the consumer within one week or within six or five days or less from the time a consumer places an order for the customized food product.

Customized Ordering and Distribution System

FIG. 1 is a simplified schematic diagram of a customized selecting, ordering and distribution system 100 for a particular type of food product, i.e., cereal. However, the system 100 described herein can be used for virtually any type of food product. In this embodiment, the system is comprised of a consumer location 102, interactive communications link 104, custom finishing facility 108, cereal base production facility 110, finishing-components suppliers 112 and, optionally, a shipping facility 114.

The consumer location 102 can be a consumers home or place of business or the home or place of business of an acquaintance, friend, relative or co-worker, any type of facility that prepares, serves and/or sells food to customers, including, but not limited to, a gourmet food store, grocery store, restaurant, bakery, bagel shop, cafeteria, bar, mass outlet, such as a fast-food restaurant, entertainment facility (e.g., movie theater, amphitheatre, live theatre, concert hall, bowling alley, sports facility, etc.), multi-purpose facility such as an airport, hospital-type facility, railroad station, bus station, cruise ship, coin laundry facility, mall, department store, further including anywhere people gather, such as in a downtown area, campus, park, beach, bank, gas station, a kiosk designed solely for access to the customized selecting, ordering and distribution system 100 or in conjunction with access to other services and/or products, and so forth. In one embodiment, the consumer location 102 is anywhere the consumer has access to a communication device, which can be handheld or otherwise, such as devices designed for a motorized vehicle such as an automobile, truck, boat, motorcycle, and the like. Through use of satellite technology, the consumer location 102 can essentially be anywhere, including any remote region, such as a camping area, mountainous area, on any body of water, any third world country, space vehicle, and so forth.

A consumer 115 in the consumer location 102 can use any number of means to communicate a customized order to a merchant. Communications may or may not be in "real-time." In one embodiment, the consumer 115 uses a computer 116 or any type of terminal to directly contact a merchant server 106. In this embodiment, the consumer 115 can communicate with the merchant via electronic mail (e-mail) or via accessing the merchant's website with an information-processing interactive communications link 104a which may be voice, data (whether or not graphic) or both, whether through wired or wireless communication. Communication using a website allows for the use of "real-time" interactive communication, providing for even greater and more convenient order customization, and is described in more detail below. Alternatively, the consumer 115 can use any type of mail service (e.g., United States mail service) 118, a conventional telephone 120, facsimile 122 or a private delivery service 124 as a means of user interface, as described in U.S. patent application, Ser. No. 09/596,275, supra. The mail service 118 can include use of a conventional catalog, brochure, order sheet, or any other type of printed information. The conventional telephone 120 can be a push-button phone system allowing entry of information and/or the merchant can provide a voice-activated phone system allowing the consumer to provide information by speaking into their conventional telephone. In one embodiment, the consumer receives information on a passive one-way device, such as a television or radio, and responds via any means described herein.

The private delivery service 124 can deliver customized food products in a particular neighborhood at regular intervals, similar to currently available frozen food home delivery services. Information provided to the merchant through any of these alternate means of communication can optionally be entered into the merchant server 106 to aid in customizing future orders for a particular consumer.

The customized order is prepared in the custom finishing facility 108. Depending on the nature of the customized food product, the custom finishing facility 108 can be designed to handle a variety of different foods and food combinations, such as beverages, snacks, meal mixes, cereals, seasonings, blends, and so forth.

In most embodiments, the custom finishing facility 108 receives the necessary base ingredients from a food base production facility, such as a food component production facility. A food "base" generally comprises one or more ingredients or building blocks common to a particular final food form or customized food product as defined herein, e.g., soups, snacks, beverages, etc. In most embodiments, the final product is a multi-component food that can be manipulated by selecting various components and varying their respective usage rates. In the example shown in FIG. 1, the food base is a cereal base, as defined herein, that is used to produce ready-to-eat cereals.

In the example shown in FIG. 1, the food component production facility is the cereal base production facility 110, which provides cereal bases 129 to the custom finishing facility 108. Such cereal bases 129 can be identical to products currently being produced by cereal manufacturers, i.e., oat, wheat, rice, barley and/or corn cereal rings, wheat corn or bran flakes, corn, rice, wheat or bran weaves, rice or wheat squares, and so forth. Additionally, cereal bases 129 can be developed or purchased from outside vendors. Again, in an alternative embodiment, the facility can be a half-product pellet production facility producing half-products with the same type of choices and alternatives being available as with the cereal bases 129.

The cereal base 129 is toted and stored in any suitable manner in order to preserve an acceptable level of freshness and minimize breakage. In one embodiment, tote size is reduced or increased from conventional size. In another embodiment, cereal bases 129 can be kept frozen until needed. In yet another embodiment, other measures to increase shelf life are used, such as keeping the cereal base 129 in a controlled atmosphere, finish drying cereal bases having high moisture content, and so forth. If a half-product pellet is used, the shelf-life is extended.

Finishing components, such as particulates, flavors and sweeteners, nutrients, and so forth, are supplied by finishing components suppliers 112 and also need to be transported and handled in an appropriate manner. For example, since some additives, such as various nutrients and particulates, degrade over time, and/or when exposed to excess heat or light, precautions need to be taken to minimize such degradation.

The custom finishing facility 108 can have a modified packaging line and involve sequential addition of desired components into individual servings until the product is complete, at which point the serving is packaged and shipped as shown in FIG. 1. Considerations unique to this manufacturing and packaging process include, but are not limited to, formula/product identification, sweetener application, sweetened base deposition, nutrient application, flavor application, allergen isolation, particulate addition and packaging.

In one embodiment, each customer formula or order is given a unique code 128 such as a bar code, which provides details as to the type and amount of each ingredient in that particular order. This code 128 accompanies each order and all packaging. In this way, the code 128 can be read, either automatically or by individuals working at the facility, at each stage in the process to ensure appropriate action.

If desired, an unfinished cereal base 129 can be sweetened with one or more sweeteners 130 to a desired sweetness level. In one embodiment, a finite number of sweetness levels are used which can be categorized as low, medium or high. Additionally, the type of sweetener 130 can be varied to include honey or a non-nutritive sweetener such as aspartame or sucralose.

The cereal base 129, which may or may not be sweetened, can then be deposited, volumetrically (or by weight or piece count), into an individual serving package 132, such as a bowl. In an alternative embodiment, the cereal base 129 is deposited into an intermediate receptacle to allow ingredients to be added and blended prior to final packaging.

Individual nutrients and nutrient blends 134 can then be added, as appropriate for each individual order. In one embodiment, gravimetric feeders are used to vary nutrient levels. Various coating technologies can be used to apply the nutrients as a coating or topping on the cereal base 129. In one embodiment, powder-coating technologies are used in which heat is applied to the coating in an amount sufficient to cause a phase change. In one embodiment, the coating becomes an amorphous "glass-like" material, which is then combined with a cereal base 129 that has itself been heated. Novel nutrient delivery technologies can also be used to combine any of the chosen additives with the cereal base 129. In one embodiment, nutrients and nutrient blends 134 are encapsulated for delivery in measured quantities or in stressified units into the cereal base 129. In a particular embodiment, nutrients 134 are microencapsulated in particles of less than about 100 micrometers in diameter and attached to the cereal base 129 using electrostatic attraction, i.e., binding of fine particulates. In one embodiment, the methods and products of U.S. patent application entitled, "Oligosaccharide Encapsulated Mineral and Vitamin Ingredients," Ser. No. 09/595/244, filed on Jun. 16, 2000 and/or U.S. patent application entitled, "Oil Encapsulating Minerals and Vitamins in a Glassy Matrix," Ser. No. 09/595/121, filed on Jun. 16, 2000, are used. In another embodiment, nutrients 134 are applied in a conventional manner using a "spray-on" technique followed by a drying step.

Concentrated solutions of volatile flavorants 136, i.e., fruit, vanilla, can be sprayed directly onto the cereal to provide any desired supplemental flavoring. In one embodiment, moisture levels and application rates are kept sufficiently low so as not to require any finish drying.

Generally, particulates 138 can be added by gravimetric feeders directly into the cereal blend contained in the individual serving package 128. In one embodiment, packages requiring the addition of potential allergens, such as nuts, are segregated at this point into a separate line.

The customized food product 139 is then prepared for shipping. In the case of a product that has been assembled directly in its finished package, such as a bowl, sachet, etc., the package is capped, rotated and turned to facilitate mixing. The package is then weighed and labeled with relevant nutrition, ingredient and serving information. In one embodiment, the information contained on the code 128 in the incoming order is used to generate an ingredient, nutrition and serving label. In this way, appropriate nutritional and ingredient labeling can be completed on each serving, if desired, or on a collection or package of single servings being prepared for an individual customer. Such a collection can comprise any number of single servings, such as one (1), seven (7), 14, and so forth. In the embodiment shown in FIG. 1, several single serving packages 128 are combined into a multi-serving package 140.

For products that have been assembled in a secondary or intermediate container, the contents can now be deposited into a primary container in a manner to allow for mixing. The primary container can then be packaged as described above. Each order is then assembled into containers for shipment. In one embodiment, packaging (as well as shipping) is completed so as to minimize breakage of the customized food product and/or to reduce odor pick-up. In the case of individual bowl servings, a tubular sleeve may be used. In the case of sachets, a more traditional case may be employed.

Once properly prepared, packaged and labeled, the customized order can be shipped directly to the consumer location 102 or other shipping destination. Alternatively, the order can be sent to a shipping facility 114 for subsequent delivery with a suitable delivery means 142, such as a truck as shown in FIG. 1, or airplane, boat, or any other delivery means required for a particular location, to the consumer location 102. In an alternative embodiment, the order is sent to a "redemption" center owned or operated by the supplier or an affiliate. The redemption center can prepare the customized product for long-distance shipping and/or otherwise complete the packaging process. In another alternative embodiment, the customized order is sent to a third-party distribution point, such as a department store, kiosk, pharmacy or any other distribution partner. In this embodiment, the consumer can then pick up the order, which could be a prescription order, at the distribution point at his or her convenience. In certain variations, final control over distribution of the product can be applied such as to insure that the consumer is not a minor, to confirm the consumer's identity and/or to confirm the accuracy and/or quality of the order.

The custom finishing facility 108 can be located any suitable distance from the cereal base production facility 110. Deliveries to the custom finishing facility 108 can be made as often as necessary and take any suitable amount of time. In one embodiment, custom finishing facilities 108 and/or cereal base production facilities 110 are located worldwide. In one embodiment, the finishing process is built in a "cassette" format that can provide a given amount of product, i.e., enough to service a particular geographic region. Such cassettes can be added in any particular location as demand dictates. As can be appreciated by those skilled in the art, unlike current finishing platforms, the finishing process of the present invention is a flexible and adaptable process.

System-Level Overview

Figure 2A:
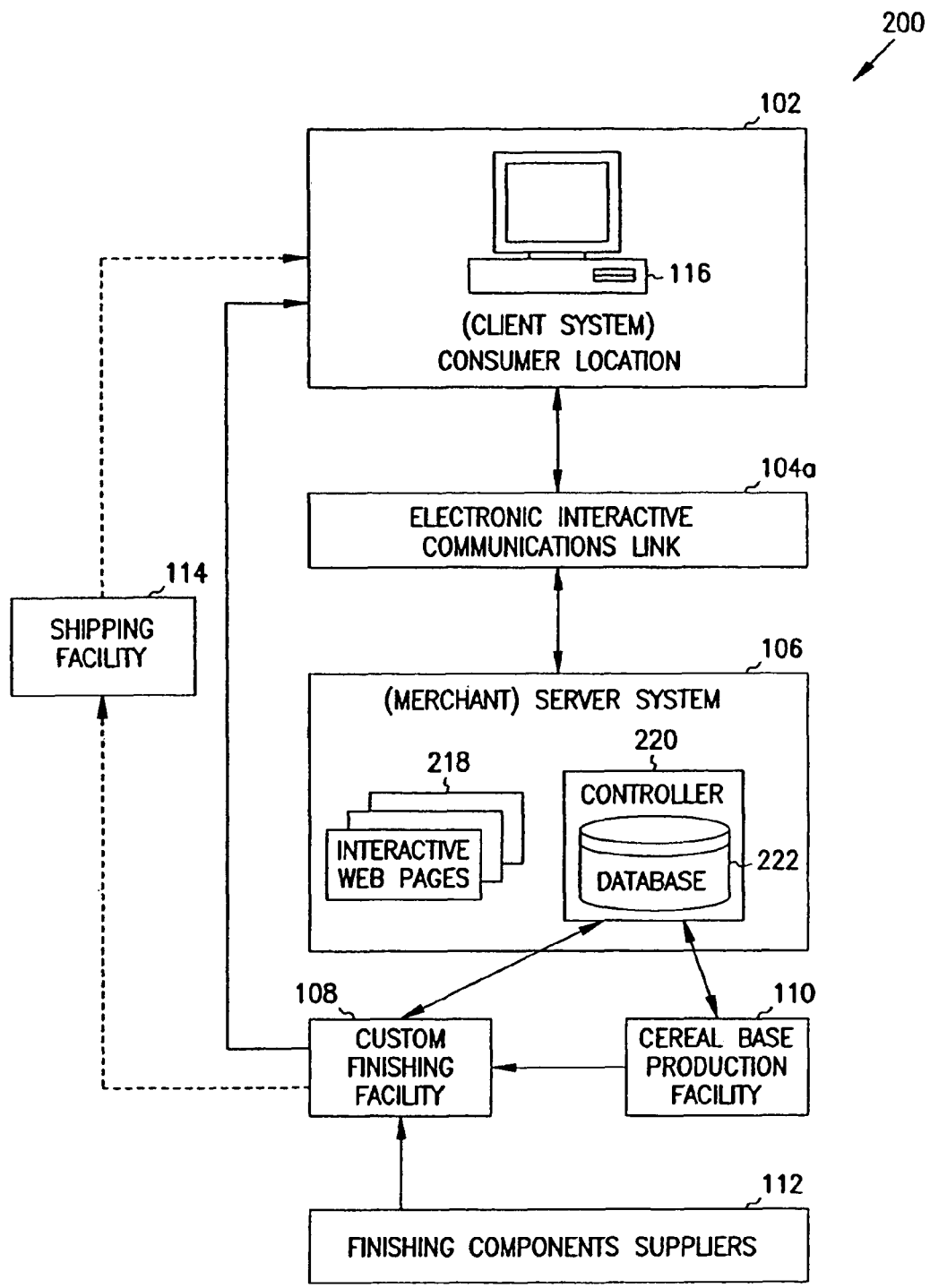
FIG. 2A is a block diagram of one embodiment of a customized food selection, ordering and distribution system.

FIG. 2A is a block diagram of one embodiment of a customized food product ordering and distribution system 200. In this embodiment, the consumer in the consumer location 102 connects with the merchant server (i.e., server system) 106 through the information-processing interactive communications link 104a shown in FIG. 1, which is essentially a "real time" communications link when used for accessing a website, as described below. In this embodiment, the consumer location 102 can essentially be anywhere the computer 116 (i.e., client system) is accessible to the consumer.

The hardware and operating environment of this invention can be practiced in any number of ways in conjunction with the various embodiments. The invention is not particularly limited to any type of client system. As such, the computer 116 can be any type of device or interface (i.e., information processor) designed to send and receive data over the information-processing interactive communications link 104a. The computer 116 can operate as a stand-alone computer system or in a networked environment using logical connections to one or more remote computers. In one embodiment, the computer 116 is a personal computer, such as a desktop computer. In another embodiment, the computer 116 is any type of portable computer, such as a conventional laptop or handheld personal digital assistant (e.g., Hewlett Packard Pocket PC®, e.g., Compaq Ipaq®, Casio Casiopeia®, etc.).

In one embodiment, the computer 116 is operatively coupled to a monitor, a pointing device, which may be manually or voice activated. In another embodiment, any type of keypad or keyboard can be used in addition to or instead of the pointing device. The monitor permits the display of information for viewing by a user of the computer. The pointing device permits the control of the screen pointer provided by the graphical user interface of window-oriented operating systems. The keyboard or keypad permits entry of textual information, including commands and data, into the computer 116. The computer 116 includes a central processing unit, random-access memory (RAM), read-only memory (ROM), and one or more storage devices, such as a hard disk drive, a floppy disk drive, a compact disc read-only memory (CD ROM), an optical disk drive, a tape cartridge drive or the like. The RAM and ROM are collectively referred to as the memory of computer 116. The memory, hard drives, floppy disks, etc., are types of computer-readable media. The computer-readable media provide nonvolatile storage of computer-readable instructions, data structures, program modules and other data for the computer 116. Computer-readable instructions stored on the computer-readable media are executable by the central processing unit of the computer 116. The computer-readable instructions perform a method of interpreting survey responses input by a method of interactively selecting and ordering a customized food product. As noted below, the computer 116 may also be capable of receiving information from one or more supplemental computing devices that may have aggregated all or a portion of the order information such as a personal digital assistant operatively connected by wire or wireless communication.

The information-processing interactive communications link 104a can send and receive signals over any type of network operatively connecting the consumer location 102 and the merchant server 106. This includes, but is not limited to, any type of wireless (e.g., infra-red) or wired connection, including satellite networks, telephone wiring, cable wiring, a local area network (LAN), a wide area network (WAN) or the Internet. In one embodiment, the network is a private WAN, such as AMERICA ONLINE™ or a pharmacy supply network. In another embodiment, any type of private Internet Service Provider (ISP) is used. In some embodiments, the consumer location 102 is connected to the merchant server 106 using a modem and a dial-up connection. In other embodiments, a high-speed data connection is used, such as high-speed cable, Digital Subscriber Line (DSL), Alternate Digital Subscriber Line (ADSL), Integrated Services Digital Network (ISDN), and so forth.

In the embodiment shown in FIG. 2A, the merchant server 106 is accessible via the Internet. The Internet itself comprises a huge collection of computer and computer networks that are interconnected through communication links. Information is exchanged using various services, such as electronic mail, Telnet, Gopher and the World Wide Web (WWW). The WWW, however, is used extensively worldwide because of its ability to send and receive graphical information commonly referred to as "Web pages" 218. Web pages 218 are typically identified by a Uniform Resource Locator (URL) commonly referred to as a "website address" or "address." In order to view a specific Web page 218, the appropriate address is entered into the computer 116 at the consumer location 102 and sent via the information-processing interactive communications link 104a to the merchant server 106. Once the request (known as a Hyper Text Transfer Protocol or HTTP request) is received by the merchant server 106, the server then sends that Web page 218 to the consumer location 102. The Web page 218 is typically displayed at the consumer location 102 using a browser, which is an application designed to request and display Web pages. The browser can include any features known in the art, e.g., global navigation or short-cut buttons accessible from some or all of the Web pages, pop-up boxes providing additional information, error messages, and so forth.

The Web pages 218 in one embodiment of the present invention contain an interactive series of questions, allowing a consumer to complete a survey in real-time, and create/select a customized food product designed to meet his or her particular health, nutrition and taste needs. Upon completing the interactive survey, the consumer can be presented with key nutritional information and specific and customized food product suggestions. This nutritional information, together with the customized food product suggestions can be generated automatically or manually, such as with any type of human intervention. At this point, the consumer can select and order a suggested customized food product. Alternatively, the consumer can further customize his food product, if desired. Optionally, the consumer can order a customized food product without completing the interactive survey. (Example Web pages are discussed further in FIGS. 4-22).

In addition to Web pages 218, the merchant server 106 also comprises a controller (or server engine) 220 and a database 222, although the invention is not so limited. In one embodiment, the controller 220 represents a collection of controllers 220 in various locations. The controller 220 can be a database server, which receives and processes the HTTP request to access Web pages 218. As a database server, the controller 220 is also used to maintain the database 222. In an alternative embodiment, the server implementing the customized ordering system can be a separate computer with access to the database 222, rather than the database itself. Such a computer can include all the necessary components for processing input signals and generating appropriate output signals, as is understood in the art, having any or all of the features as described above for the consumer's computer 116. Such a computer can be coupled to a router, which, in turn, is coupled to a digital service unit/customer service unit (DSU/CSU). The DSU/CSU is connected to the information-processing interactive communications link 104a by any of the aforementioned means.

The database 222 can include customer information, such as information on existing or potential purchasers, including, but not limited to, name, address, personal information provided in response to questions on the interactive Web pages 218, automated reordering information, and so forth. The database 222 can also have order information on previous and/or outstanding orders. The database 222 can track inventory by storing information on various food product components, such as cereal bases and additives, which can be ordered by the consumer.

In order to display nutritional and taste information and suggestions on the interactive Web pages, the responses provided by the consumer are collected and analyzed by the controller 220. Such analysis is completed using software programs containing appropriate routines and algorithms designed to collect and interpret data, as well as to summarize and display results unique to the particular responses given. Depending on the consumer responses, the controller 220 issues instructions to display recommendations and information designed to uniquely meet a particular consumer's needs.

In an alternative embodiment, the display device comprises virtually any means for displaying information as is know in the art, including, but not limited to any type of paper products (e.g., in the form of a letter, brochure, magazine, book, label, and so forth). In such an embodiment, the user interface can further comprise any type of communication device known in the art, including, but not limited to any type of writing device, such as a pen, pencil, and so forth. In one embodiment, there is no display device, and the information is communicated only by audio means, such as cassette tapes, compact discs, and so forth. In an alternative embodiment, the survey responses are reviewed by an individual, either instead of, or in addition to being analyzed automatically by the pre-programmed controller 220.

Once a particular formulation is ordered by a consumer, which may be a food formulation, such as a cereal formulation, never made prior to this point in time, the merchant server 106 provides information to the custom finishing facility 108 where the customized order is prepared. The merchant server 106 also needs to provide information regarding ingredient and nutrition labels. In one embodiment, a computer program running on the merchant server 106 is designed to develop a set of rules unique to that product. The process includes using a look-up table that gives precise nutritional values for all the components of the new product, evaluating their overall contribution based on weight, computing the total weight of all of these components, including micro and macronutrients, and instructing a printer to create a label having nutritional values and total weight. Additionally, functions that assign mass (weight) values to all the components must be completed in order to create a proper ingredient label that is complete and accurate. Such a label lists ingredients in descending order based on their amount, by weight, in the product.

As noted above, the custom finishing facility 108 is supplied with food components from a food component facility, such as the cereal base production facility 110. Various finishing components or additives are supplied from any number of finishing component suppliers 112. After the customized product is packaged and labeled with the appropriate label, it is shipped to the consumer as described above.

Figure 2B:
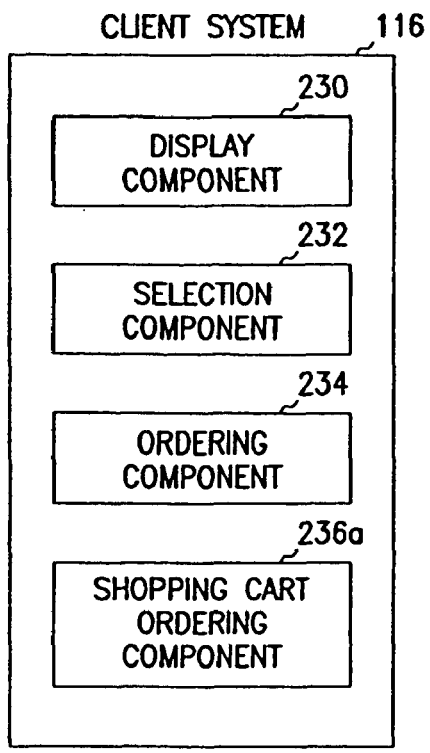
FIG. 2B is a block diagram of one embodiment of a client system.

FIG. 2B is a block diagram of the client system 116 comprising a display component 230, selection component 232, ordering component 234 and shopping cart ordering component 236 as described herein. The display component 230 displays a list of additives for creating a customized food product. The selection component 232 allows selection of one or more ingredients, i.e., additives, from the list of ingredients to create the customized food product. The ordering component sends a request to a server system to order the customized food product. The shopping cart ordering component 236*a*, in response to performance of an add-to-shopping-cart action, sends a request to the server system to add the item to a shopping cart.

Figure 2C:
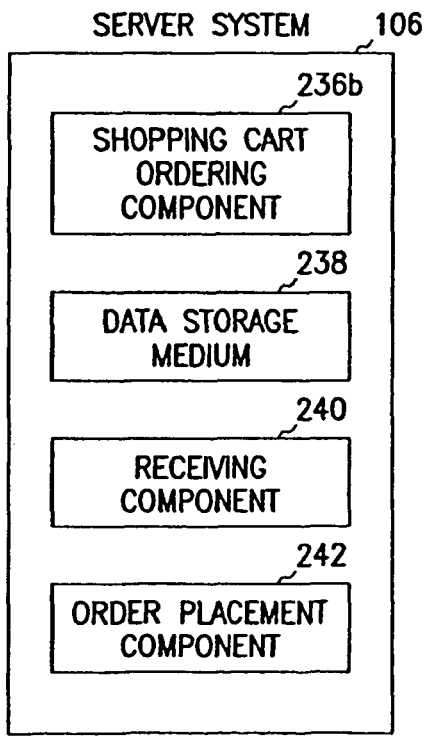
FIG. 2C is a block diagram of one embodiment of a server system.

FIG. 2C is a block diagram of the server system 106 comprising a shopping cart ordering component 236, a data storage medium component 238, a receiving component 240 and an order placement component 242 as described herein. The shopping cart ordering component 236*b* adds a requested item to a shopping cart. The data storage medium component 238 stores information for a plurality of users using a unique code for each order. The receiving component 240 receives requests to order a customized food product. The order placement component 242 retrieves the unique code from the data storage medium component and uses the information associated with the unique code to place an order for the user identified by the unique code.

Essentially the system provides a computerized method for providing a plurality of ingredient combinations for a customized food product, i.e., "Design Phase." In one embodiment, the process continues with receiving one or more preferences from a user for the customized food product. In a particular embodiment, as noted above, the preferences are received in response to a computerized survey such as a web-based survey. An example embodiment of a web-based consumer survey is described herein and in U.S. provisional patent application Ser. No. 60/181,282, supra. In one example, the user's preferences are based on a user's taste requirements for the customized food product ("taste preferences"). For example, survey questions concerning taste can be used to determine food product preferences as to types of form, ingredients, flavors, sweetness, serving size, particulates, types (e.g., hot or RTE cold), and the like. In another example, the user's preferences are based on a user's health concerns and nutritional requirements for the customized food product ("health concerns"). For example, survey questions concerning health needs can be used to determine health concerns based on a user's general health state (i.e., gender, age, obesity, activity level, and the like), as well as specific health concerns and conditions (i.e., heart disease, cancer risk, osteoporosis, menopausal symptoms, tobacco use, nutrient consumption patterns, diabetes, and the like).

In an alternate embodiment, the consumer's nutritional requirements as determined by a health professional or advanced technology are used, rather than the user's preferences. This alternate embodiment allows a health professional to enter a patient's nutritional requirements in order to obtain a recommended food product that, in whole or part, meets the specified nutritional requirements of that patient. This alternate embodiment further allows data such as medical test results to used rather than consumer preferences. Recommending a customized food product based, in whole or in part, on medical test results allows a medical professional to prescribe a customized diet for a patient based on that patient's unique nutritional requirements.

The computerized method can continue by selecting one or more of the plurality of ingredient combinations as a recommended customized food product based on the one or more preferences received from the user. In a specific embodiment in which a cereal product is being designed, the ingredients can be organized into any number of categories. In one embodiment, the ingredients are organized into three categories: bases, clusters, and particulates. The terms "base," "cluster," and "particulate" are defined in the first section of this detailed description. The process of recommending one or more of the plurality of ingredient combinations of a customized food product to a user can be referred to as the "Application Phase." In an example embodiment, selecting one or more of the plurality of ingredient combinations results in at least one recommended customized food product that best satisfies the taste preferences, at least one recommended customized food product that best satisfies the health concerns and at least one recommended customized food product that best satisfies both the taste preferences and the health concerns of the user.

An alternate embodiment of the computerized method of recommending a customized food product uses ingredient templates. As used herein, an ingredient template (also referred to as a "template") refers to a definition of a customized food product using at least some general categories of ingredients rather than specific ingredients. In other words, an ingredient template is a generalized recipe or generalized combination of ingredients. In one example, an ingredient template defines a customized ready-to-eat cereal product as containing multigrain flakes, high fat particulates, and high density/high fiber fruits. High fat particulates are one category of particulates. High density, high fiber fruits are another category of particulates. Several different actual ingredient combinations are possible for a single ingredient template such as the example ingredient template defined above. For example, an actual ingredient combination for the example ingredient template defined above is multigrain flakes, walnuts, and dates. Another actual ingredient combination for the example ingredient template defined above is multigrain flakes, sliced almonds, and dates.

In this embodiment, the computerized method of recommending a customized food product from a plurality of ingredients comprises classifying at least some of the ingredients into physically and/or nutritionally-similar ingredient categories. A plurality of ingredient templates are generated from the ingredients and the ingredient categories using predefined rules of combination. Preferences are received from a user or health professional, for example, for a customized food product. One or more of the ingredient templates are selected based on the preferences. A specific ingredient is selected from each one of the ingredient categories in the one or more ingredient templates based on the preferences received. The customized food product recommended to the consumer comprises the actual ingredients selected for the selected ingredient template.

The processing modules and software modules necessary to perform the design phase functions, as well as the application phase functions, are described in U.S. patent application Ser. No. 09/699,622, supra. In one embodiment, an output of the design phase processing modules is a set of ingredient templates to be searched in the "application stage." The set of ingredient templates represents "virtual food products." The virtual food products are created by logically combining the ingredients (bases, clusters, and particulates) in a manner that maximizes the diversity of the choices available to a consumer. Some of the combinations represent commercially-available food products. However, many of the combinations represent food products that are not, nor ever have been, commercially available.

In one embodiment, the ingredient template outputs are organized into two groups. In one embodiment, the first group comprises ingredient templates that are used to recommend a customized food product primarily based on health and diet criteria and secondarily based on taste preferences. The second group comprises ingredient templates that are used to recommend a customized food product based only on taste preferences without regard to health and diet criteria (except for over-fortification rules).

Methods of Using Example Embodiments

In the previous section, a system level overview of the operation of an example embodiment of the invention was described. In this section, the particular methods performed by a processor or controller, such as the controller 220 of FIG. 1, can be described by reference to a series of flowcharts and diagrams. The methods to be performed constitute computer programs made up of computer-executable instructions. The methods shown in FIG. 3A-3H are implemented in connection with a machine readable medium comprising machine readable instructions for causing a computer to perform the method. Such machine-readable medium may include software modules and computer programs. The computer programs comprise multiple modules or objects to perform the methods, or the functions of the processing modules in a computer automated detail routing system. The type of computer programming languages used to write the code may vary from procedural code type languages to object oriented languages. The files or objects need not have a one to one correspondence to the modules or method steps described depending on the desires of the programmer. Further, the method and apparatus may comprise combinations of software, hardware and firmware. Describing the methods by reference to flowcharts enables one skilled in the art to develop such programs including such instructions to carry out the methods on suitable computerized systems.

Figure 3A:
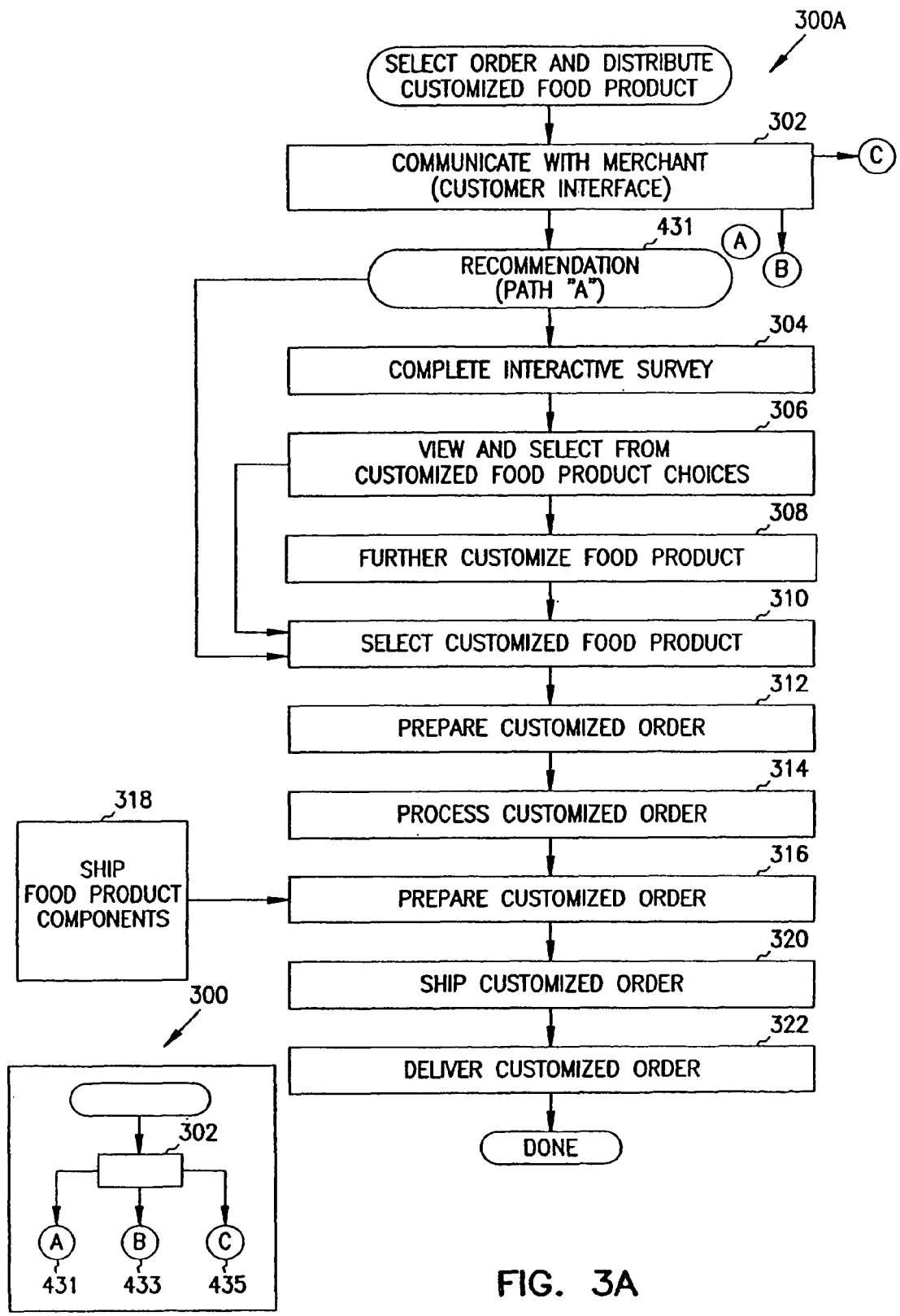
FIGS. 3A-C is a flow diagram showing one embodiment of a routine for a customized food selection, ordering and distribution system.
Figure 3B:
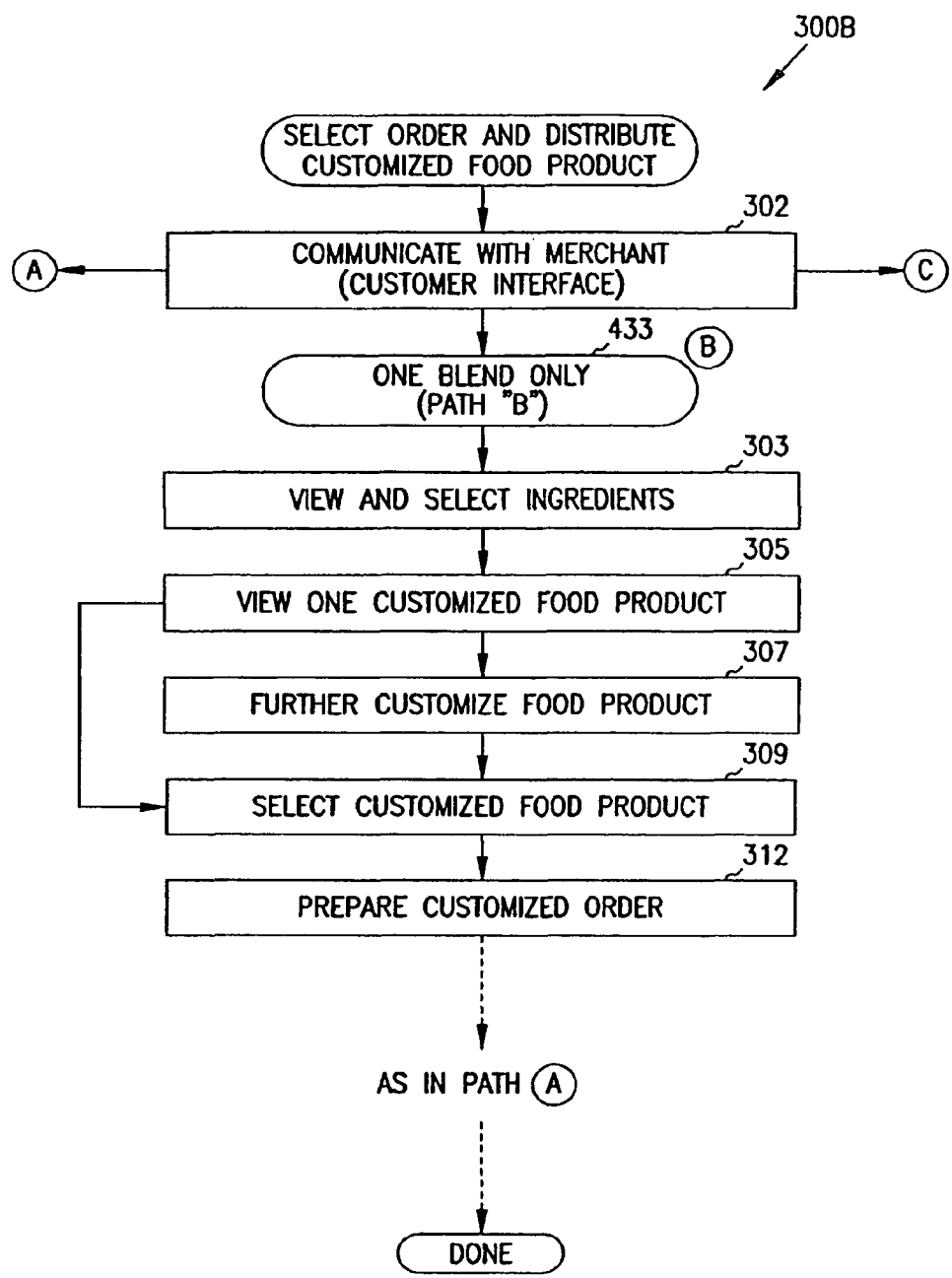
Figure 3C:
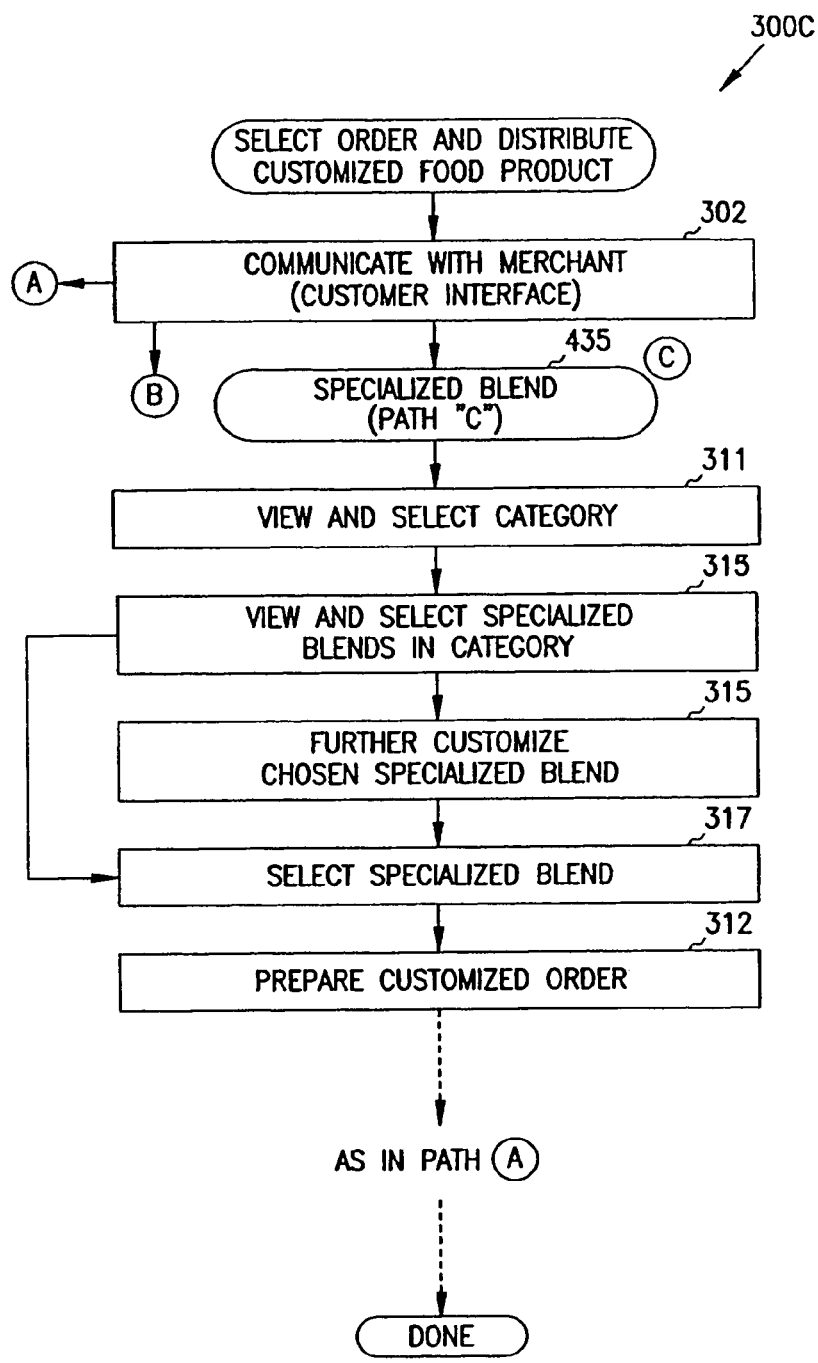

FIGS. 3A-C provide a flow chart showing one embodiment of a routine for interactively selecting, ordering and distributing a customized food product. In this embodiment there are three different routes or paths a consumer can take, although the invention is not so limited. Recommendation Path "A" 431 which provides full customization, "One Blend Only Path "B" 433 which provides for limited customization and the "Specialized Blends Path "C" 435, which provides selected categories and can optionally offer some customization capabilities.

For each path, the method 300 begins with a customer interface step when a consumer communicates 302 with a merchant. In the embodiment shown in FIG. 2A for example, such communication is performed by accessing the merchant server with the information-processing interactive communications link (104a). For the consumer choosing the Recommendation Path "A" 431 shown in FIG. 3A, he can then complete 304 an interactive survey, either on-line or via telephone, mail, fax, and so forth. The interactive merchant survey asks questions to determine health, nutrition and taste preferences of each consumer. (The details regarding these questions are described in FIGS. 8-11). Basically, the consumer can be quizzed as to what types of foods, such as particular cereal types or brands they currently enjoy, as well as preferences as to grains, sweetness, nutrition, serving size, packaging, flavors, particulates and type (e.g., hot or RTE cold). In other embodiments, the user may select form among any number of categories of food to answer questions only in the area or areas of interest. The survey also quizzes consumers regarding their general health state, i.e., gender, age, obesity and activity level, as well as specific health concerns and conditions, i.e., heart disease, cancer risk, osteoporosis, menopausal symptoms, tobacco use and nutrient consumption patterns.

The consumer then views and selects 306 from customized food product choices provided by the merchant that best suits the taste and health needs of the individual. With this invention, it is now possible to vary a number of attributes relating to a food product. For example, with cereal or snack products, the attributes that can be varied include, but are not limited to, grain type or types, flavors, sweetness, nutrition, serving size, packaging, particulates, type (e.g., hot or cold RTE). The consumer can then choose to further customize 308 one or more of the food product choices prior to selecting 310 a customized food product. Alternately, the consumer can select 310 one of the customized food products he viewed 306 initially.

In an alternative embodiment, the consumer can select 310 the customized food product without completing the interactive survey. For example, this can be the steps followed for established customers who can instead use any type of automated refill or reordering system located on the merchant server. In one embodiment, an automated reordering system is resident in the computer 116 or in any type of appliance or inventory management device owned by the consumer.

The consumer than sends a request to the merchant server system to place 312 a customized order for one or more particular cereal products. In one embodiment, the consumer is required to provide credit card information to complete placement of the order. The merchant server receives the request, which can be identified with a unique code as described above. The merchant server system then processes 314 the customized order by first generating an order to purchase the customized food product, with information sent to a custom finishing facility. The generated order is then fulfilled to complete the purchase of the customized food product. Specifically, the custom finishing facility prepares 316 the customized order, i.e., constructs the personalized product using the appropriate food product base which has been shipped 318 from the appropriate food production facility. Order information can also be sent to the food product base production facility for inventory-tracking purposes.

The customized order is then shipped 320 via any suitable means and delivered 322 to the consumer. The customized order can be delivered directly to the consumer or to a redemption facility, such as a department store, where the consumer goes to pick up the order. In one embodiment, the entire process from placing the order to receiving the order takes about 7-10 days. In another embodiment, the process takes five (5) to six (6) days or less.

For the consumer following the One Blend Only Path "B" 433 as shown in FIG. 3B, he first views and selects 303 ingredients from various categories to create a customized food product. For example, to create a customized cereal product on Path "B," the consumer can select a limited number of ingredients from among various categories such as cereal form (e.g., puffs, rings, flakes, squares museli, granola, biscuits, nuggets, shreds, and so forth), clusters/add-ins, nuts, and dried or freeze-dried fruits. In this embodiment, the merchant can provide restrictions as to the types of ingredients that can be combined by advising the consumer to not mix ingredients in one "group" with another, and further programming the software to limit combinations accordingly. The consumer then views 305 one customized food product and can then choose to further customize 307 the one food product prior to selecting 309 the customized food product. Alternately, the consumer can select 309 the customized food product initially viewed 305. The process than proceeds as described in Path, "A" with the customer placing 312 the customized order and so forth, until the customized food product is delivered 322 to the consumer.

For the consumer following the Specialized Blends Path "C" 435, shown in FIG. 3C, he first views and selects 311 from among various categories, such as health (e.g., weight management, energy, heart health, and so forth), taste (e.g., chocolate, nuts, and so forth), and favorites (e.g., popular blends, celebrity choice, merchant favorites, and so forth). In one embodiment, the favorites category can also include a category to allow the consumer to modify an existing food product, such as a brand name cereal, e.g., Basic 4® In this embodiment, the merchant can build in any necessary restrictions to modification in order to prevent a food product from being produced that is unhealthy, organoleptically unsatisfying, and so forth. The consumer then views 313 from among the specialized blends in their chosen category. The consumer can then choose to further customize 315 the one chosen specialized blend prior to selecting 317 the specialized blend. Alternately, the consumer can select 317 the specialized blend initially viewed 305. The process than proceeds as described above in Path, "A" with the customer placing 312 the customized order and so forth, until the customized food product is delivered 322 to the consumer.

FIG. 3C is a flow diagram of a routine that enables interactive selecting and ordering of a customized food product. Under the client system 116, a list is displayed 342. The list can contain additives and either food bases or half-product choices. A selection 344 is made from the list and a request 346 to order is sent to the server system 106. The server system receives 348 the order request and identifies 350 the order with a unique code. An order is then generated 352 to purchase the customized food product.

Figure 3D:
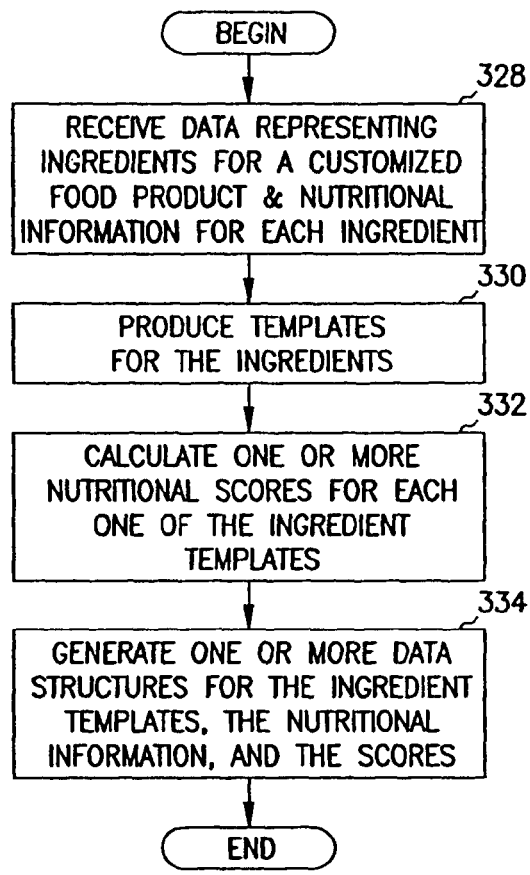
FIG. 3D is a high-level flowchart of one embodiment of a computerized method of recommending a customized food product.

FIG. 3D is a high-level flowchart of one embodiment of a computerized method of providing a plurality of ingredient templates for a customized food product. As shown in FIG. 3D, the computerized method of providing a plurality of combinations for a cereal food product begins by receiving 328 a first set of data representing ingredients for a customized food product and a second set of data representing nutritional information for each one of the ingredients. In one embodiment, the ingredients are organized into nutritional groups. In an example embodiment, the nutritional groups comprise bases, clusters, and particulates. The computerized method shown in FIG. 3D uses the data received to produce 330 a set of generalized combinations (also referred to herein as templates) of the ingredients. The computerized method then calculates 332 one or more nutritional scores for each one of the generalized combinations. The computerized method also generates 334 one or more data structures comprising a plurality of combinations of the ingredients, the nutritional information, and the one or more nutritional scores for each one of the generalized combinations of the ingredients.

In an alternate embodiment, the computerized method shown in FIG. 3D also filters the generalized combinations of ingredients before and/or after calculating the scores. In another alternate embodiment, categories are provided within the particulate and cluster nutritional groups. The generalized combinations of the ingredients follow rules predefined for the minimum and maximum levels that each category can exist in an ingredient template.

Figure 3E:
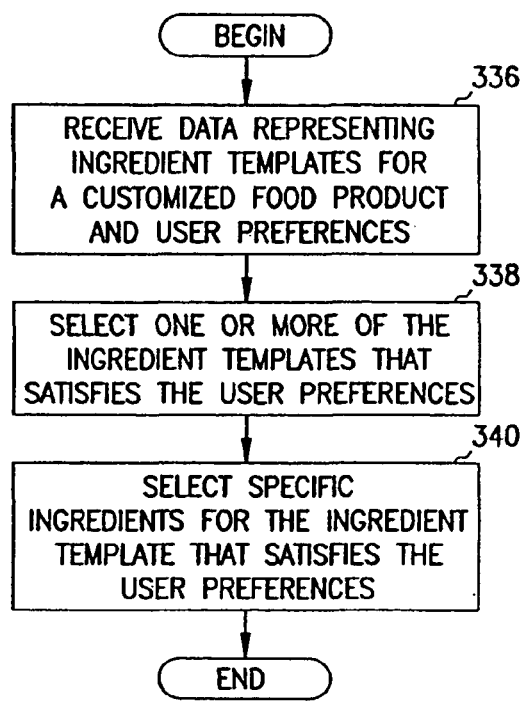
FIG. 3E is a high-level flowchart of one embodiment of a computerized method of recommending a customized food product.

FIG. 3E is a high-level flowchart of one embodiment of a computerized method of recommending a customized food product based on one or more consumer preferences. As shown in FIG. 3E, the computerized method of selecting one or more of a plurality of combinations for the customized food product based on the one or more preferences provided by a user receives 336 data representing a plurality of generalized combinations of ingredients for a customized food product and user preferences for the customized food product. The computerized method selects 338 one or more of the generalized combinations that satisfies the user preferences and selects specific ingredients from the generalized combination based on the user preferences.

Figure 3F:
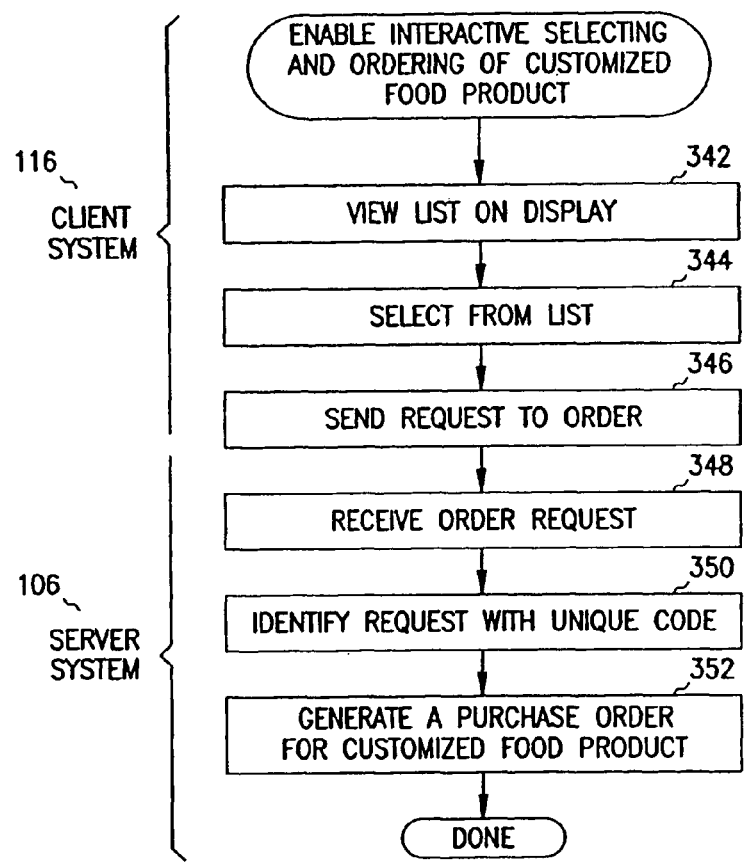
FIG. 3F is a flow diagram showing a routine for one embodiment of an interactive selecting and ordering of a customized food product.

FIG. 3F is a flow diagram of a routine that enables interactive selecting and ordering of a customized food product. The process is comprised of a client system 116 and a server system 106. Within the client system 116 a list is viewed 342 on a display, a selection is made 344 from the list and the resulting request is sent 346 to order. Within the server system 106, the order request is received 348, the request is identified 350 with a unique code and a purchase order is generated 352 for a customized food product.

Figure 3G:
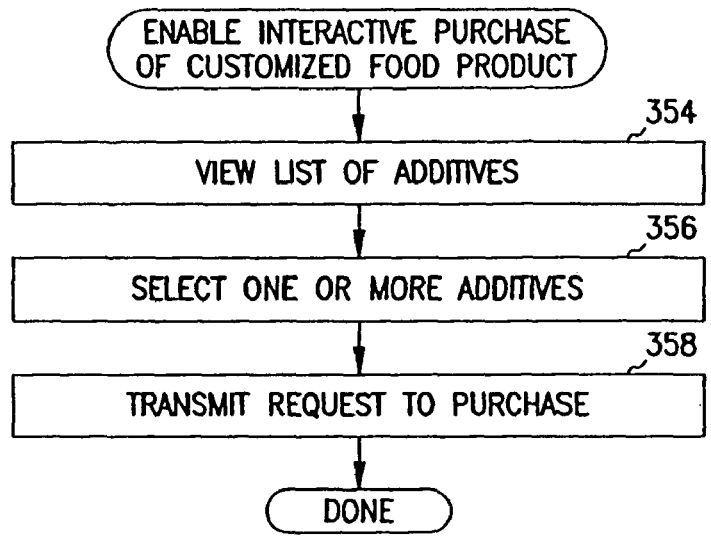
FIG. 3G is a flow diagram showing a routine for one embodiment of creating a customized food product.

FIG. 3G is a flow diagram of a routine that enables an interactive purchase of a customized food product. The process begins when a list of additives is viewed 354. One or more additives are then selected 356. A request to purchase the food product is then transmitted 358.

Figure 3H:
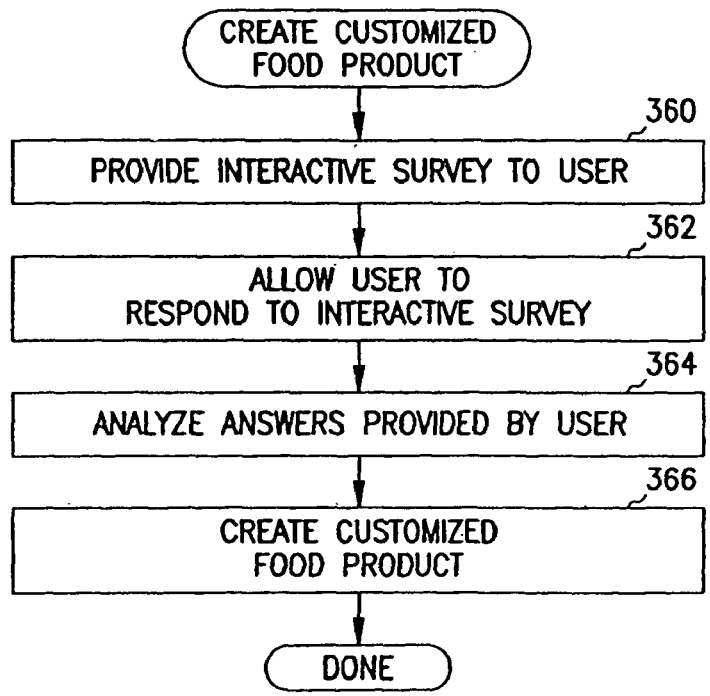
FIG. 3H is a flow diagram showing a routine for one embodiment of an interactive purchasing of a customized food product.

FIG. 3H is a flow diagram of a routine for creating a customized cereal product. The process begins when an interactive survey is provided 360 to a user. The user is allowed 362 to respond to the interactive survey. The answers provided by the user are analyzed 364. A customized food product is then created 366.

Figure 3I:
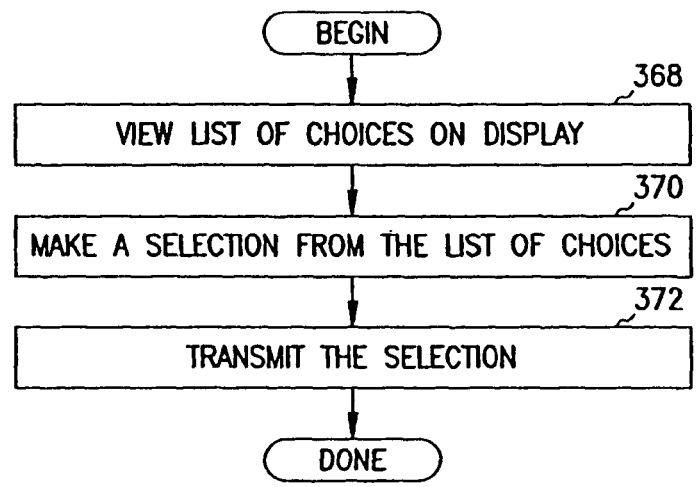
FIG. 3I is a flow diagram showing a routine for one embodiment of a computerized method of selecting and ordering a customized food product.
Figure 3J:
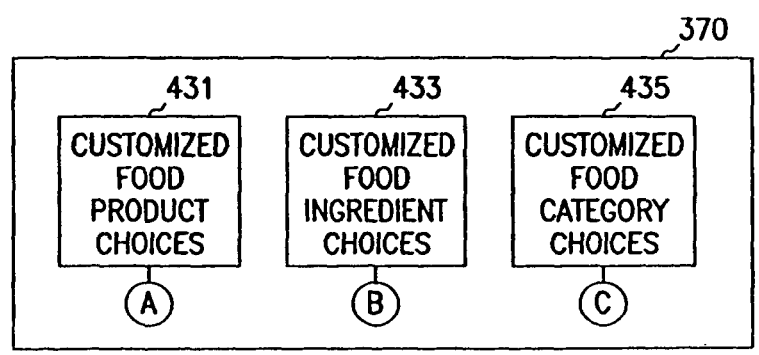
FIG. 3J is a block diagram of a system for implementing an application phase of a customized food selection, ordering and distribution system.

FIG. 3I is a flow diagram of a routine for selecting and ordering a customized food product. The process begins when a list of choices is viewed 368 on a display. A selection is then made 370 from the list of choices and the selection is transmitted 372. As shown in FIG. 3J, the list of choices 370 in this embodiment includes a customized food product choices 431 (Path A), customized food ingredient choices 433 (Path B) and customized food category choices 435 (Path C).

Figure 3K:
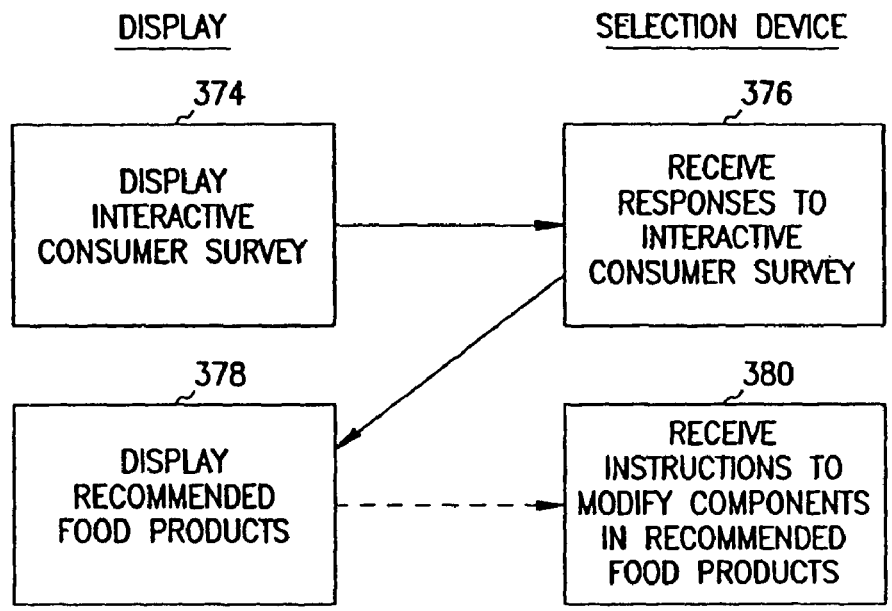
FIG. 3K is a block diagram showing one embodiment of a method of creating a customized food product with a computer system having a graphical user interface that includes a display and a user interface selection device.

FIG. 3K is a block diagram showing one embodiment of a method of creating a customized food product with a computer system having a graphical user interface that includes a display and a user interface selection device. The process begins when an interactive consumer survey is displayed 374 (display). A response is received 376 to the interactive consumer survey (selection device). Recommended food products are then displayed 378 (display). Instructions can then optionally be received 380 to modify components in recommended food products (selection device).

Figure 3L:
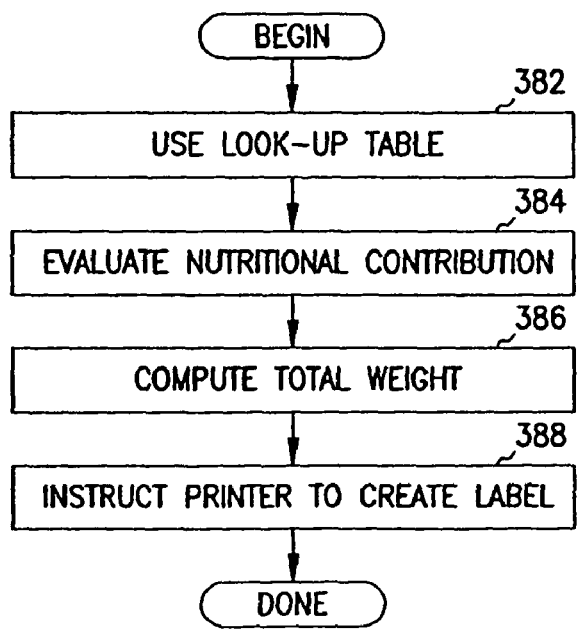
FIG. 3L is a flow diagram showing a routine for one embodiment of a method for producing a nutrition and ingredient label.

FIG. 3L is a flow diagram of a routine for producing a nutrition and ingredient label. The process begins with using 382 a look-up table. Nutritional contribution is evaluated 384. A total weight for the components is computed 386. Finally, a printer is instructed 388 to create a label.

High Level Overview of an Example Implementation of a Website

As noted above, the Web pages 218 contain a series of questions designed to learn about each individual consumer's needs and desires, including their health and taste preferences. Again, although the present invention applies to any type of food product, the example interactive Web pages herein (FIGS. 4-22) refer specifically in places to customized cereal products, including fully customized products, i.e., creating a new cereal, specialized blends, i.e., blends for specific taste or health needs, blends created by others, and so forth, and a semi-customized blend, i.e., blending from a limited number of ingredients, the user interface described herein is applicable to any type of customized food product. In one embodiment, the user interface is as described in U.S. Provisional Application, Ser. No. 60/181,282, supra.

One skilled in the art can appreciate that the various Web pages and various sections of the Web pages can be omitted, rearranged or edited in a variety of ways. Furthermore, any type of graphics, color schemes, audio and/or visual means can be used, including adding logos, pictures, animations, applets, streaming video, photographs, computer-generated voices, live voices, music, and so forth, as is known in the art, where appropriate to emphasize or enhance a particular Web page in design and/or function. Where it is noted that information can be entered by clicking a "button," this is a reference to placing a cursor over a predefined area of the displayed information, and then clicking on a mouse button. However, any means or combinations of means known in the art can be used additionally, or in the alternative, to enter information. This includes, but is not limited to, voice recognition means, typing means in which a keyboard or similar device is used to type the desired information into a data entry field, and so forth. In one embodiment, the Web pages are in various languages.

FIG. 4A provides an exemplary Web site overview or map 400 containing first and second global navigation sets, 401a and 401b, respectively, having various buttons or links that can be made available on every Web page of the Web site, although the invention is not so limited. However, global navigation capability can provide convenient one-step links to any number of desired locations, as is known in the art. In one embodiment, there is only one global navigation set having most or all of the links described in the two sets herein (401a and 401b) and/or different links, additional links, and so forth. In other embodiments, there are no global links or the number and type of links can vary, depending on the page being accessed. In one embodiment, each set of links is located at about the same location on every Web page. In one embodiment, the Web site is operational virtually around-the-clock.

Figure 4B:
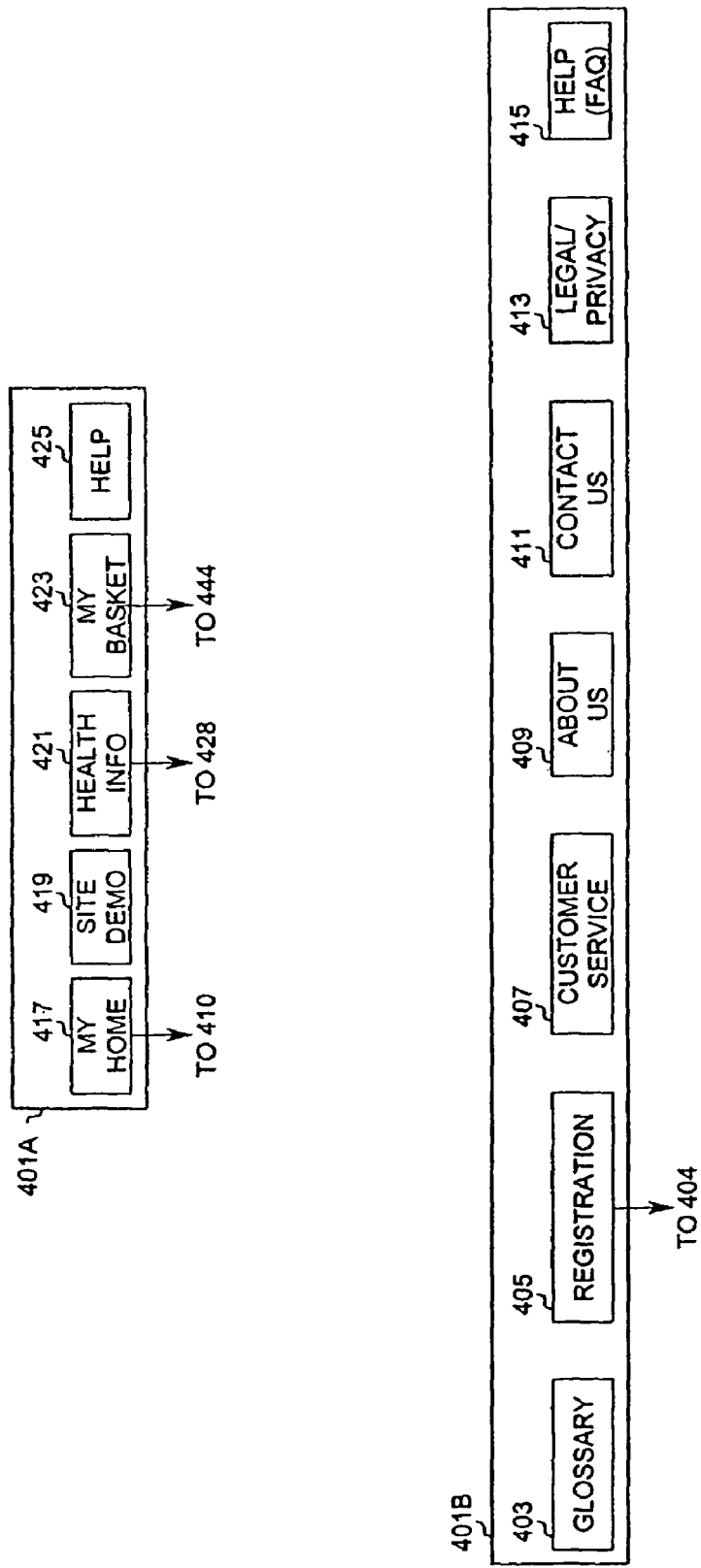
FIG. 4B is a block diagram showing one embodiment of global navigation on a sample Web site.

Referring now to both FIGS. 4A and 4B, the first global navigation set 401a provides a "glossary" button 403, "registration" button 405, "customer service" button 407, "about us" button 409, "contact us" button 411, "legal/privacy" button 413 and "help/FAQ" button 415. Again, in alternative embodiments, some or all of these buttons may be varied or omitted.

Upon choosing the "glossary" button 403, the glossary page is displayed for the user. In one embodiment, this page provides only ingredient terms. In another embodiment, this page also provides definitions for various health, nutrition, taste and food terms that consumers may be interested in. Essentially any terms of interest can be defined including medical terms, fitness terms, and so forth. In one embodiment, pictures and/or streaming video is also included in the definitions. In another embodiment, there is an audio feature provided to help explain the terms. The glossary page can also provide links to sites that can provide further information on a particular word, phrase or topic. In one embodiment, the glossary page has a "health information" button 421 and/or a "help/more information" button 408 and/or a help/FAQ button 415 to link directly to those pages.

Upon choosing the "registration" button 405, the user is taken to the "create or edit account" page 404 in which information such as name, shipping address, billing address, phone number, and so forth, can be entered and saved. In one embodiment, the consumer also has the option to enter and save credit card information. The user can then be prompted to select a user name and password as is known in the art. In the future, voice identification, retinal scanning, fingerprint or any other unique biological identifiers that become more widely available can also be used instead of or as a type of password. The "customer service" button 407 brings the user to a page that provide means for the user to contact the Web site service representatives by phone, fax and/or e-mail with any questions about the Web site. On this page, the user can be given the option to be contacted or not. In one embodiment, there is a statement on the customer service page that contact will occur within a certain time period, such as 24 hours. In one embodiment, there is an active link to the service representative's e-mail address.

The "about us" button 409 provides access to a page that can describe the history and capabilities of the Web site's product and service provider. Qualifications of the staff who provide consumer information can also be presented here. In one embodiment, the staff is comprised of persons having backgrounds in nutrition science, public health, clinical nutrition, medicine, pharmaceuticals, alternative medicines, and food science, and so forth. In one embodiment, the staff includes persons with Master's level and/or doctorate level degrees.

The "contact us" button 411 provides access to a page having similar information and links as described above for customer service. In one embodiment, the "contact us" button 411 and customer service button 407 are combined into a common link. In another embodiment, the "contact us" page provides access to any of the help and/or information areas, including access to a live chat room in which users can visit directly with nutrition and health experts as described herein.

The "legal/privacy" button 413 provides access to a page that outlines the privacy policy of the site. Details as to what information is collected and how it is used can be given. A statement that this site is intended for use by adults 18 years or older is also preferably made. Other information can include details on information automatically collected from the user's browser server's domain.

The "help/FAQ" button 415 provides direct access to the FAQ portion of the help page. Such questions may pertain to technical questions on how to use the site, in which case the user might be directed to the demo page. Other questions may pertain to privacy issues, nutrition issues, health and taste issues, cost, delivery and shipping issues, return and refund issues, and so forth.

The second global navigation set 401b provides a "my home" button 417, "site demo" button 419, "health info" button 421 and "my basket" button 423. There can additionally or alternately be a "condition information" button on which the user can link to review their most recent personal health or nutrition profiles and/or taste information. From here there can be links to other health-related websites as described herein. In another embodiment there is a "feature" button which provides instant access to a customer chat-room and/or update information pertaining to what is new on the website. In this way, customers with similar health problems can interact and share to discuss favorite customized food products, general health issues, and so forth. Access to an update area also provides means for the merchant to communicate statistics about the site to its users, such as commenting on what percentage of users have ordered with certain components, what is the most sought-after customized food, what the latest changes are to the site itself, and so forth. In other embodiments this type of information can be provided on any of the web pages described herein. As above, in alternative embodiments, some or all of these buttons may be varied or omitted.

The "my home" button 417 provides direct access to the "my home" page 410 (FIG. 6) described below. The "site demo" button 419 provides access to a non-interactive demonstration of how to use the site, such as through use of a sample order. Such a demonstration can be on a series of screens through which the user is prompted to advance or which advances automatically, any type of video and/or audio presentation and so forth. The demonstration can include, for example, how a survey may be completed, how choices are presented, how further customization may be done, how the product may be ordered, how to follow a particular path, if applicable, and so forth.

The "health info" button 421 can take the user directly to the "what's new" page 428, which lists various health topics and subcategories that are active links to other pages with additional information. The "my basket" button 423 takes the user directly to the "my basket" page 444 (FIG. 17) described below.

Figure 5:
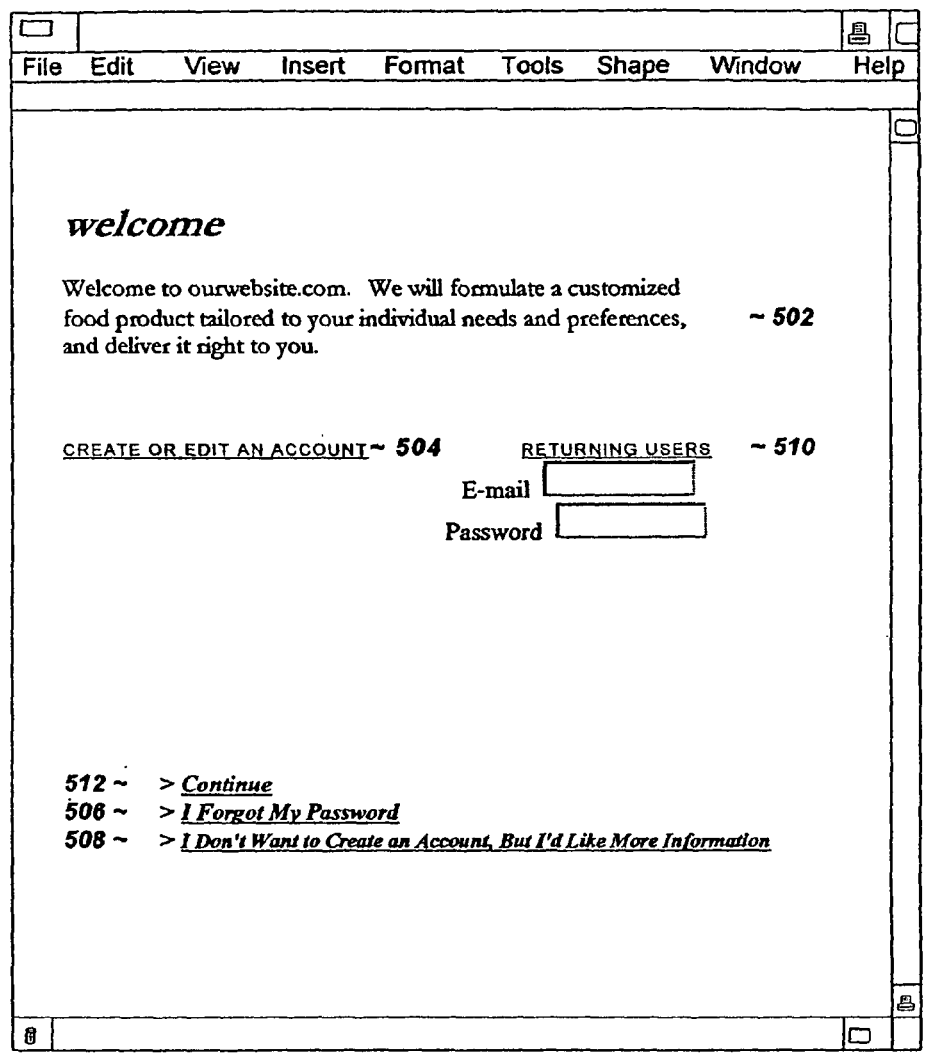
FIG. 5 is a sample Web page showing one embodiment of a "home/log-in" page.
Figure 6:
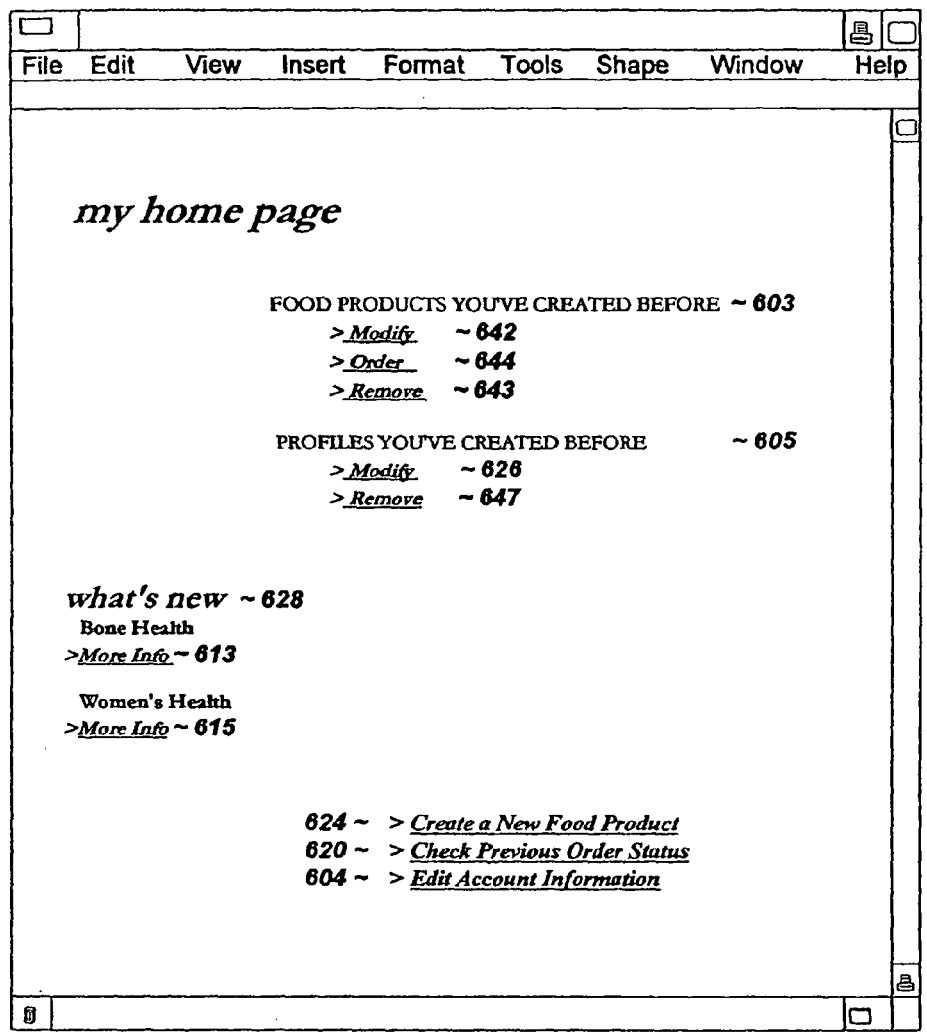
FIG. 6 is a sample Web page showing one embodiment of a "my home" page.

Referring again to the various Web pages 218 in FIG. 4A, in this embodiment, there is a home/login page 402 (FIG. 5) from which one can go to the "create or edit account" page 404, "request a forgotten password" page 406, "more information" section of the help page 408 or to their personal home page, i.e., "my home" page 410 (FIG. 6). After completing the "create or edit account" page 404, this user can also enter his personal home page 410. If the user is a returning user who has forgotten his password, he can request a forgotten password on the "request password" page 406 by verifying his identity. The verification process can take any form, such as accurately responding to a question previously answered during the registration process. If the user is successful in responding to the question, his password is e-mailed to his personal e-mail account, as is communicated on the "e-mail password to user" page 412. If the attempt to sign-in fails due to an improperly entered password or user name, the user will receive an error message page (or insert) 414, requesting that he try again. This may happen for a certain predetermined number of attempts, such as about three or four, after which the user will need to authenticate his password as described above, so it can be e-mailed to him, as is communicated on the "e-mail password to user" page 412. If the user is unable to remember their password and/or user name, he can go to the "create or edit account" page 404, if desired.

If the log-in is successful, the user enters his personal home page, i.e., "my home" page 410 (FIG. 6). From the "my home" page 410, the user can choose to go to the "modify" page 442 (FIG. 15) or the "my basket" page 444 (FIG. 17). Additionally, the user can go to the "create a new food product" page 424 (FIG. 7), the "order status" page 420 or the "create or edit an account" page 404. The user can also access the taste and health survey to edit information, for example, beginning at the "who is this for?" page 426 (FIG. 8) to edit his profile. Additionally, the user can view general health information on the "what's new" page 428 and click on links there to go to more detailed information, as desired. In one embodiment, the "feature" and/or "condition information" links discussed above are available from here.

In the embodiment shown in FIG. 4A, at the "create a new food product" page 424 (FIG. 7), the user can select Recommendation Path "A" 431, One Blend Only Path "B" 433 or Specialized Blends Path "C" 435. In other embodiments, there may be only one or two paths. In yet other embodiments there may be more than three paths, such as a separate path for altering current popular products, i.e., adapting current products by packaging, price, amount, components, and so forth. (In the embodiment described herein, this type of option is included in the One Blend Only Path "B" 433, See also FIG. 21). For the user who selects any of the paths, a "who is this for?" page 426 (FIG. 8) can be displayed. For the user who selects either of Paths "A" 431 or "B" 433, an "about me" page 428 (FIG. 9) can be displayed in which the user is asked to answer some additional personal details.

For the user on Path "A" 431, the next page can be a taste survey or "my taste," page 430 (FIGS. 10A-10C), which asks a series of personal taste-related questions. The next page can be a "health survey" page 432 (FIGS. 11A-11B), which asks a series of health-related questions. In other embodiments, there may be additional and/or alternate survey questions covering other topics that may be useful in recommending particular types of customized food products. The user can then be presented with a "fully customized recommendations" page 434 (FIGS. 12A-12B) in which a number of custom blends are presented for his review. From the "fully customized recommendations" page 434, the user can go to the "ingredients/nutrition" page 438 (FIGS. 13A-13B) or to any type of compare page, such as "compare" page 436 (FIG. 14).

Figure 12A:
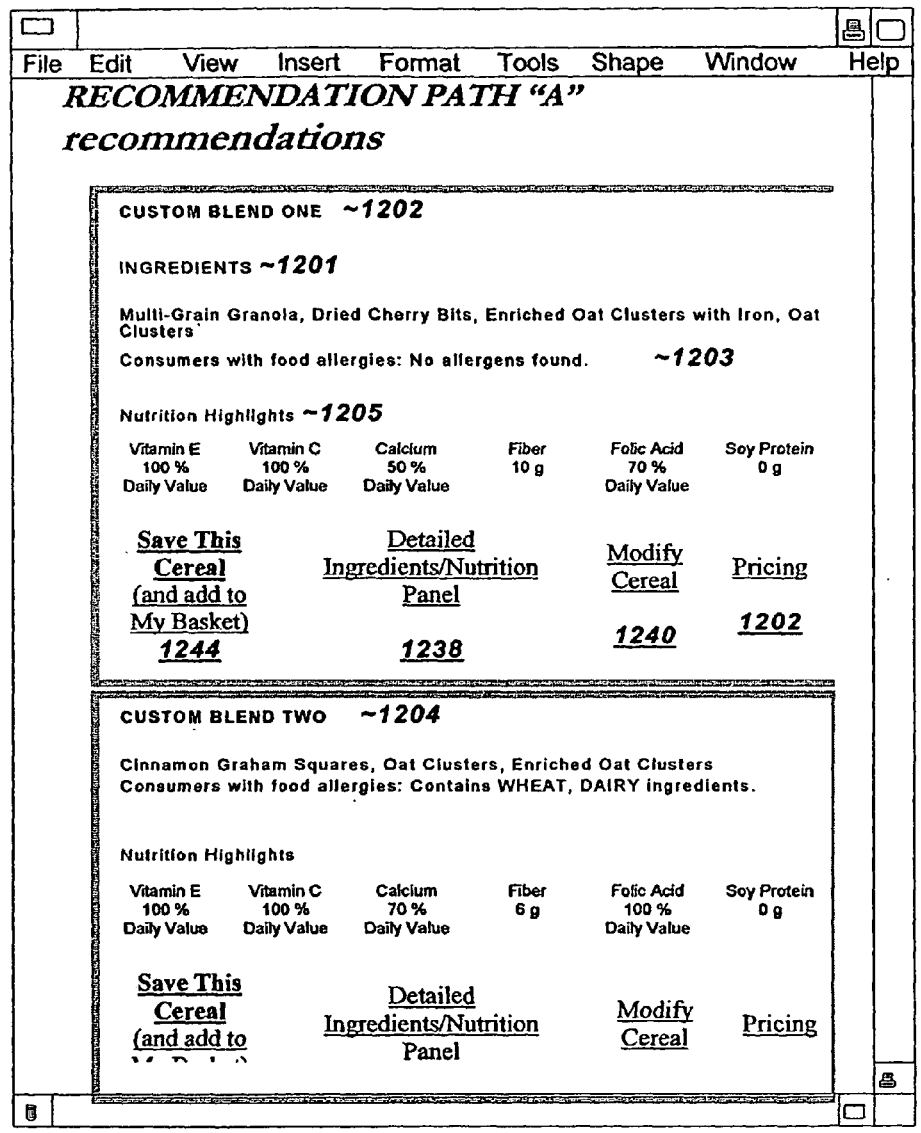
Figure 13A:
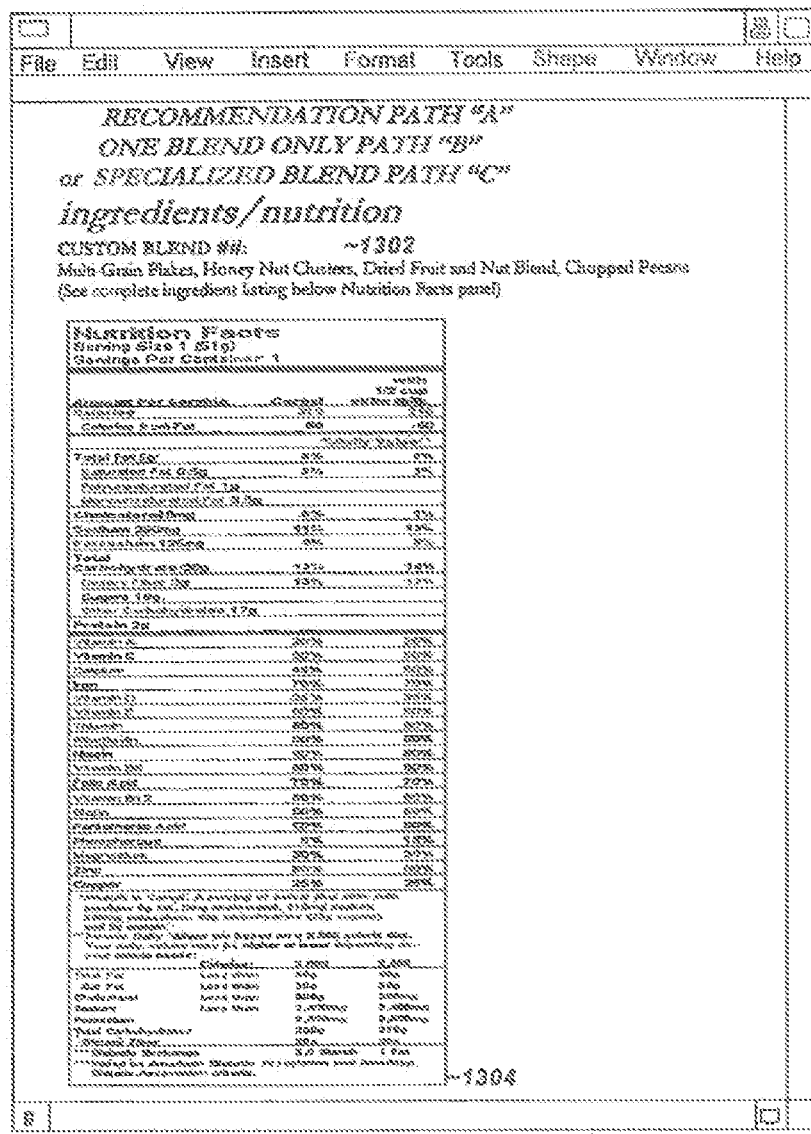
FIGS. 13A-13B are sample Web pages showing one embodiment an "ingredients/nutrition" page viewed on Paths A, B, or C.
Figure 13B:
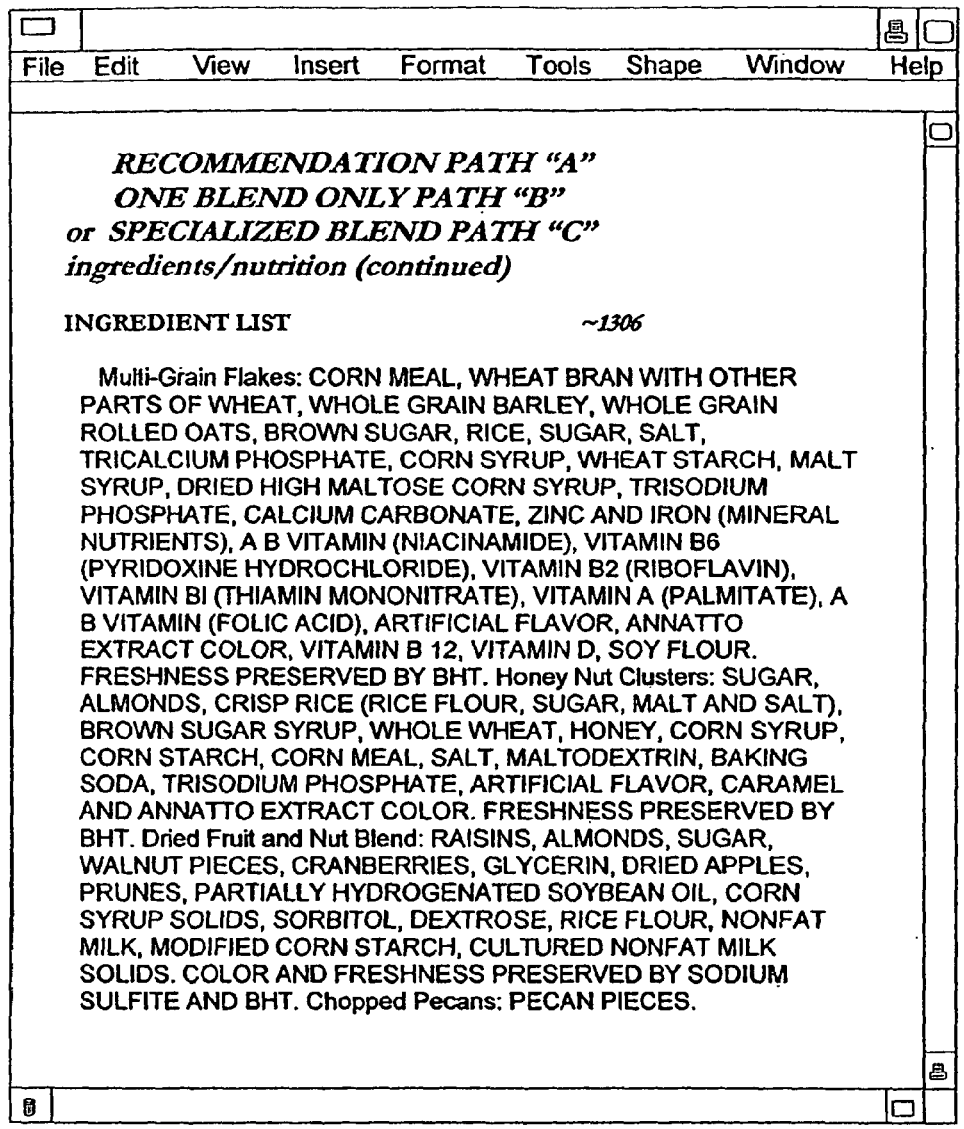

The user can also choose to go to the "modify" page 440 (FIG. 15), to modify any of the recommended blends. The user can then go to the "save and name" page 442 (FIG. 16) where he selects a unique name for the food product or return to the "fully customized recommendations" page 434 (FIGS. 12A-12B). Alternatively, the user can proceed to the "save/name" page 442 (FIG. 16) from the "full customized recommendations" page 434 directly. From the "save/name" page 442, the user can next view the "my basket" page 444 (FIG. 17), the "billing and shipping" page 446, and the "checkout" page 448.

Figure 15:
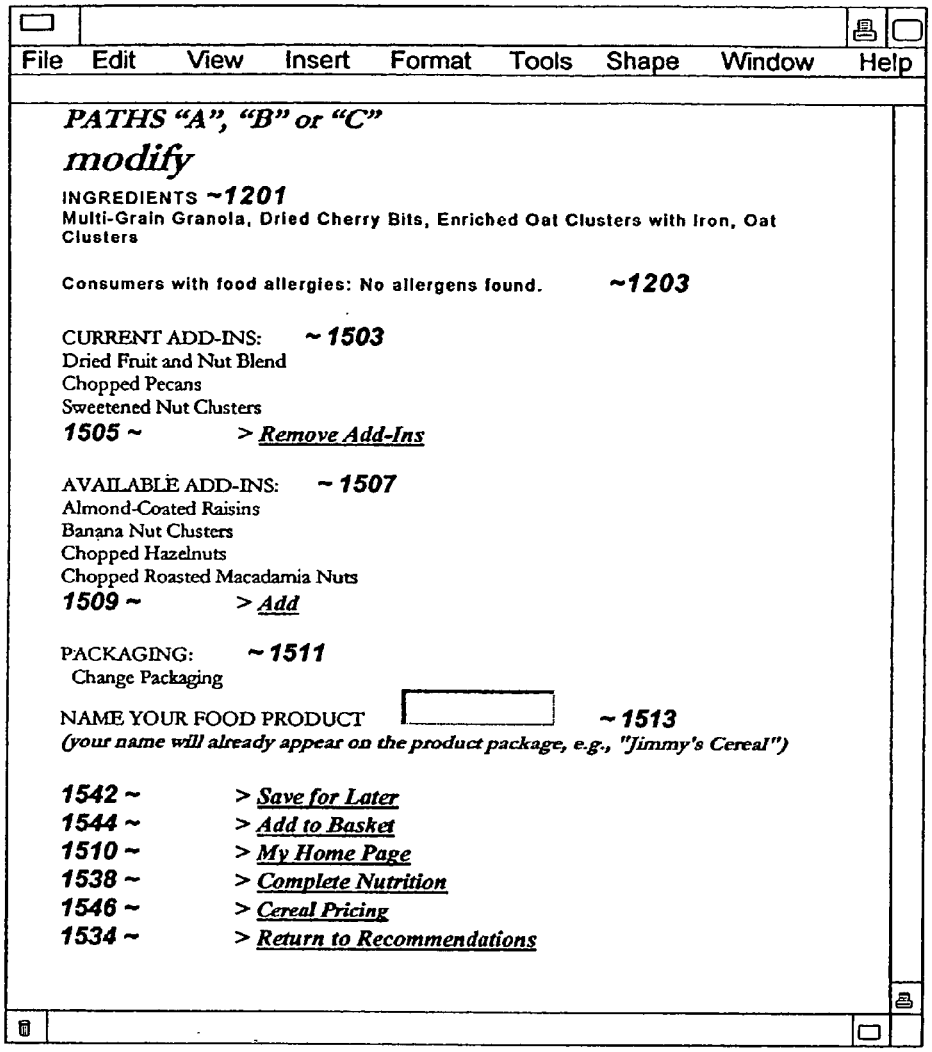
FIG. 15 is a sample Web page showing one embodiment of a "modify" page viewed on Paths A, B or C.

For the user on the One Blend Only Path "B" 433, after completing the "about me" page 428 (FIG. 9), an alternate taste survey on the "my taste preferences$_2$" page 450 (FIGS. 18A-18C) can be completed, in which various ingredients are selected for the food product. From there, the user can then proceed to a "one blend recommendation" page 435 (FIG. 19), which will have one selection for the user to view. From here, the user can go to the "ingredients/nutrition" page 438 (FIGS. 13A-13B) or to any type of compare page, such as a page that compares the one blend recommendation with competitive products or with any other product of the user's choosing. In one embodiment, the user can modify the selection at the "modify" page 440 (FIG. 15). In another embodiment, there are no modification capabilities on Path "B." In yet another embodiment, there are alternately or additionally, specific brand names listed on the "my taste$_2$" page 450, from which the user can select and modify in any manner, such as with the methods available on the "modify" page or with a special modification page, such as the example shown in FIG. 20. From either of the modification pages or directly from the "one blend recommendation" page 435, the user can return to the "one blend recommendation" page 435 or proceed to the "save/name" page 442 (FIG. 16) and proceed as described above for Path "A" 431.

For the user on Path "C" 435, after completing the "who is this for?" page 426 (FIG. 8), a "specialized blends categories" page 456 (FIG. 21) can be viewed, which offers several special categories of customized foods from which to choose. In most embodiments, after selecting the category of interest, the user is presented with multiple choices on the "specialized blends selections" page (FIGS. 22A-22D). After deciding on the final product, the user can then proceed to the "save/name" page 442 (FIG. 16) as with the other embodiments. In an alternative embodiment, the user on Path "C" 435 can make modifications as in Paths "A" or "B."

Description of Sample Web Pages in the Above-Described Example Implementation

Describing a few of the exemplary Web pages 218 outlined above in more detail, the user typically begins his visit to the Web site at one or more introductory or home pages, although the invention is not so limited. Preferably, sufficient information is conveyed to help the user understand the nature of the site and what steps to take next. For example, the introductory page can generally recite the offering of healthy and delicious breakfast cereals or other foods, including beverages, frozen products, and so forth, customized to meet the specific nutritional needs and taste preferences of online customers. Such a Web page can also note that such products are not available in conventional stores. In one embodiment, however, a consumer can arrange to pick up their order at a local store. In a particular embodiment, the customized food product can actually be a prescription item prescribed by the user's medical caregiver, which can be delivered to the user's home or picked up at a local pharmacy.

Further information on the overall selecting and ordering process can be given. This can include a statement explaining that by answering a few taste preference and health questions, the sponsor of the Web page will design food products, such as cereal blends, that fit a consumer's particular needs. There can also be a statement that this Web site will also provide the on-line consumer with health and nutrition information that can help him or her lead a healthier life. The merchant can also promise to keep any information provided by the consumer in confidence. In one embodiment, the privacy statement is repeated on other Web pages and/or global links are provided. Such a statement may be particularly reassuring for those who seek to fully customize their food by answering a series of personal taste, health and lifestyle questions. An invitation to "come in" to the site can also be given.

FIG. 5 shows one example of a "welcome/log-in" page 402 that includes a welcoming introductory statement 502 that is designed to provide a brief overview of the Web site. In some embodiments, however, a returning user may begin his visit to the website at his own personal home page, i.e., the "my home" page 410 (FIG. 6), that he previously created. This Web page can also optionally contain any type of "create or edit an account" button 504 that links to the "create or edit an account" page 404 shown in FIG. 4. If the user has forgotten his password, he can click on the "forgot password" link 506 to go to the "request password" page 406 shown in FIG. 4. If the user is not ready to create an account, but would like to learn more about the site, he can click on the "more information" button 508 to be connected to the "more information" section of the "help" page 408 (FIG. 4).

The "home/log-in" page 402 can also have a sign-on component containing data entry fields for entering a user name or e-mail address and a password, after which the user can use the "returning user" button 510, the "continue" link 512, hit the enter key on his keyboard, or use any other known means for uploading his information to the server. If the information is entered properly, the user enters the "my home" page 410 (FIG. 6). Otherwise, he proceeds to the login/error request password page 414 as described above in FIG. 4.

The "my home" page" 410 is a personalized area that is unique to each user. This page can contain this user's most recent survey response, most recent health, taste and nutrition information that has been provided by the merchant, favorite or previously-saved links, such as health and pharmacy links, and so forth. In one embodiment, the personalized area contains specific questions from the merchant geared towards this individual consumer as to whether there have been any changes in health or lifestyle, whether any planned events have occurred, e.g., surgeries, childbirth, menopause, etc., based on information previously provided by the consumer. In one embodiment, this information also contains an estimated or actual date of occurrence. In this way, the process becomes iterative, such that the merchant is able to develop a profile on each consumer and continue to "learn" about the changing needs of each individual accessing their website. This same iterative learning process can occur using any other means of communication, including, but not limited to, telephone, fax, mail, and so forth.

FIG. 6 provides one example of the "my home" page 410. In this embodiment there is a title, "my home page" 602 as well as a food product description 603 of food products this user has previously created. The description might list who the food product was created for, the date the food product was last modified, the name previously chosen for the product, and so forth. In this embodiment, the user can select the "modify food product" button 642 to go to the "modify" page 442 (FIG. 15) or the "order" button 644 to go to the "my basket" page 444 (FIG. 17). The user can also choose the "remove food product" button 643 to delete this particular creation. Additionally, the user can click on the "create a new food product" button 624 to go to the "create a new food product" page 424 (FIG. 7), the "check on the status of an order" button 620 to go to the "order status" page 420 or the "edit registration information" button 604 to go to the "create or edit an account" page 404. (See FIG. 4). In this embodiment there is also a profile description 605 that contains a list of profiles this user has previously generated. Such profiles are created in response to questions asked in the user surveys described herein. In this embodiment, the user can select the "profile modify" button 626 to modify any of the profiles listed. In one embodiment, this action takes the user to the "who is this for?" page 426 (FIG. 8) in order to enter the survey area. The user can also choose the "profile remove" button 647 to completely remove one or more profiles.

From the "my home" page 410 the user can also click on a "what's new" link 628 to go to the "what's new" page 428. Alternatively, the user can click directly on topics of interest that are featured on the "my home" page 410. In one embodiment, the topics that the user views have been custom-selected based on the user's responses to the health and taste surveys. In the embodiment shown in FIG. 6, the topics are bone health and women's health, with corresponding links, 613 and 615, respectively, to more information. In one embodiment, there is also some specific information on these topics also included on the "my home" page 410. In one embodiment, software is available to provide "constructed" text, which addresses an individual's various unique concerns and needs. Such constructed text can be assembled from a collection of component text that itself is put together from bits and pieces of information. For the user concerned with heart health, for example, the software program analyzes and arranges data that the user has input in order to provide a customized "booklet" of topics personalized for that individual.

In other embodiments, the customized food selection, ordering and distribution website is essentially a one-stop health resource for consumers. For example, there may be topic choices and information available on the my home page 410 related to any number of health-related topics, including, but not limited to child and teen nutrition, colon cancer risk reduction, diabetes, dietary guidelines, digestive health, energy, heart health, men's health, mental health issues (e.g., depression, including postpartum depression), and so forth. Other topics can also be covered, such as specialty diets as described herein (low sodium, Weight Watcher's®), etc., further including ethnic and religious diets, e.g., Lenten fasting, Jewish kosher foods, Islamic food law, Halal, etc. Preferably links, such as 613 and 615 in FIG. 6, are available to provide more information on each topic. In one embodiment, the "more information" links provide access to additional health information, such as tips for preventing problems in this particular health area, case studies, definitions, exercise tips, information on how to reduce stress, and so forth. In one embodiment there are also menu suggestions (e.g., weekly menu planner, daily menu planner, etc.), recipes, links to other health-related sites, and so forth. These can include various health websites known in the art, including sites sponsored by private organizations, including not-for-profit organizations, and so forth. In one embodiment, there is a complete list of all of the health-related topics presented on each page in this area. In another embodiment, there is a link to a live chat room, which has experts in various health-related fields available.

Figure 16:
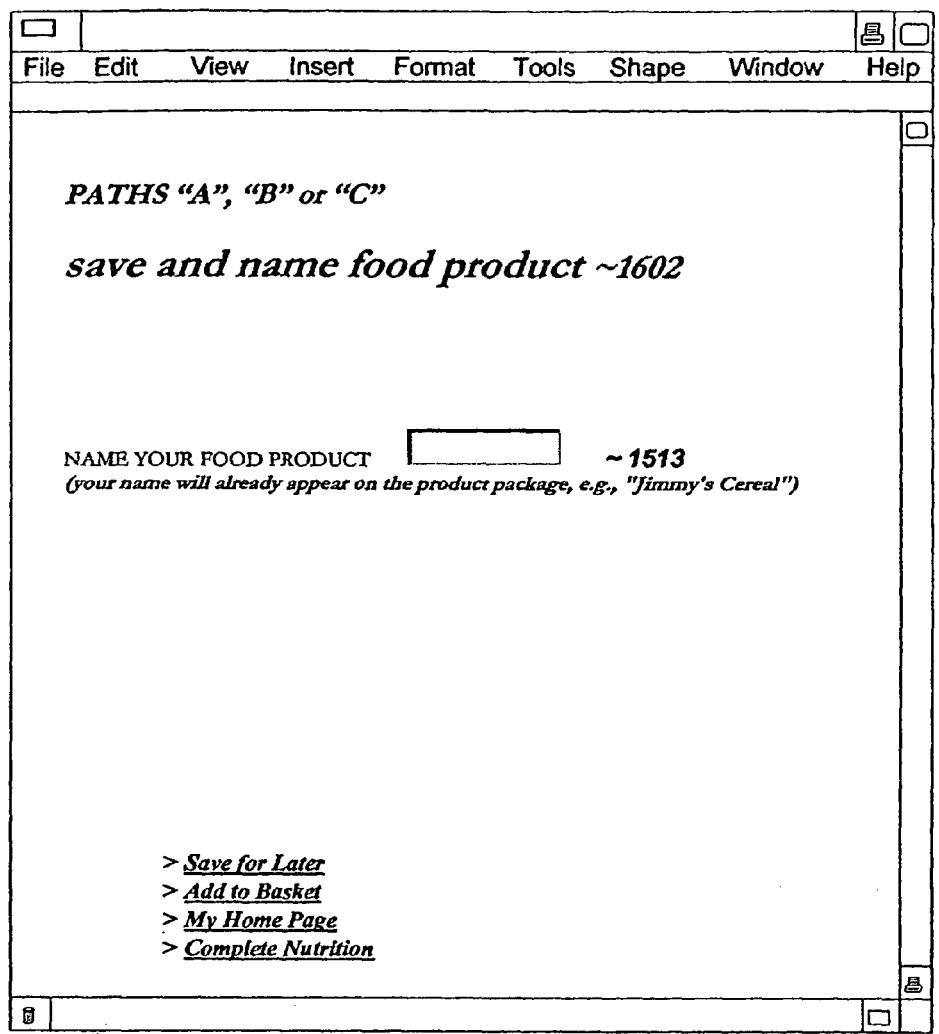
FIG. 16 is a sample Web page showing one embodiment of a "save and name food product" page viewed on Paths A, B or C.

In another embodiment, the website provides personalized tracking of a user's health, including information such as blood pressure, cholesterol and so forth. For example, in response to the user entering specific health data, the merchant can periodically provide graphs and charts tracking these values, similar to information provided by on-line financial businesses. In a particular embodiment, this health information can be posted on the user's "home page" 410 (FIG. 16). In one embodiment, this information is posted together with the survey summary described below. In another embodiment, this information is sent to the user via any other means (e.g., facsimile, hardcopy, etc.) in a separate communication or together with any type of survey summary, which may include interpretative information and suggested foods, as noted above.

In one embodiment, the website provides even more detailed advice to the consumer by including a "personal nutritionist" feature that can help alter bad eating habits and poor nutrition in the same manner as a financial planner seeks to help alter bad spending habits and poor finances. This feature can also simply help to maintain an existing healthy lifestyle, providing personalized and detailed information, essentially a "virtual" nutritionist. As is known in the art, in general, for a normal, healthy person with no particular food sensitivities (e.g., allergies, intolerances, etc.), no one food, alone or consumed in moderation, will have a significant negative impact on a consumer. However, chronic consumption or a steady diet of particular foods can lead to a diet having negative or health impact. The virtual nutritionist feature can help to educate consumers in this regard and can further construct diet plans that help maintain a healthy lifestyle that is not unnecessarily restrictive.

In one such embodiment, a database is created having the nutritional content for most foods, including any type of common foods, gourmet foods, exotic foods and so forth. These foods can be grouped initially in any manner, such as by countries, regions, ethnic groups, and so forth, and additionally or alternately be grouped in any other suitable manner, using the technology that provides the recommendations herein and as detailed in the U.S. application Ser. No. 09/699,622, supra. In this way, the foods are put in an appropriate format for sorting and managing. In one embodiment, foods are grouped in more than one manner, such as generically and/or by brand name. In one embodiment, fast foods are grouped together. In other embodiments, foods are grouped generically and/or by brand name according to the pyramid groupings used by the United Stated Department of Agriculture.

A consumer can then input information into the system about the foods they are currently eating or perhaps would like to eat, what food is currently in the pantry, cupboard, and/or refrigerator, and so forth. Essentially the consumer can provide information as to the types of foods they like to eat, how often they eat, activity level, health concerns, and so forth, thus generating their own personal "nutritional and health profiles." Using the database together with the customized food product builder described herein, this information can be analyzed and interpreted to output specific recommendations for this particular user. For example, the consumer can first be told about the level of nutrition he is currently receiving from the foods he is ingesting (similar to tracking expenses for a certain period of time to identify where a person's money is going). The consumer can also be told whether or not he is meeting minimum dietary requirements in any number of areas. For example, it may be that he is ingesting twice the fat he should be getting and/or only 30% of the fiber and 10% of the vitamins. Once this information is presented to the consumer, he can then seek help from within the site in planning appropriate menus and foods to make sure he eats healthier (i.e., plan and follow a budget), by selecting a nutritionally appropriate diet based on the foods the individual consumer prefers. For example, the consumer can be told to avoid eating certain foods, limit the intake of certain foods, and so forth. This feature essentially provides a diet plan customized to a consumer's own personal eating regimen by using the consumer's own personal commonly used foods.

Furthermore, by knowing what is in the consumer's home, advice can include menu planning, which can further include grocery list preparation. In one embodiment there is a link to on-line grocery stores. Such a service can be used in combination with any of the features described herein, not only to improve a consumer's health and fitness, but to further enhance the consumers on-line shopping experience. In an alternative embodiment, the information is given to the consumer as a service in and of itself, and can be provided to the consumer by any known means. In one embodiment, the information is presented live in a chat room, via audiovisual material, and so forth. In another embodiment, the user interface is a telephone through which a computer or live operator can take down the consumer's personal information, or the consumer can fill out a form and mail it in; virtually any known communications means can be used. The desired output can then be sent via mail, fax, e-mail, posting to the user's own home page on the website, and/or any other known means. Further counseling sessions can occur using any known means for inputting and outputting information.

Figure 7:
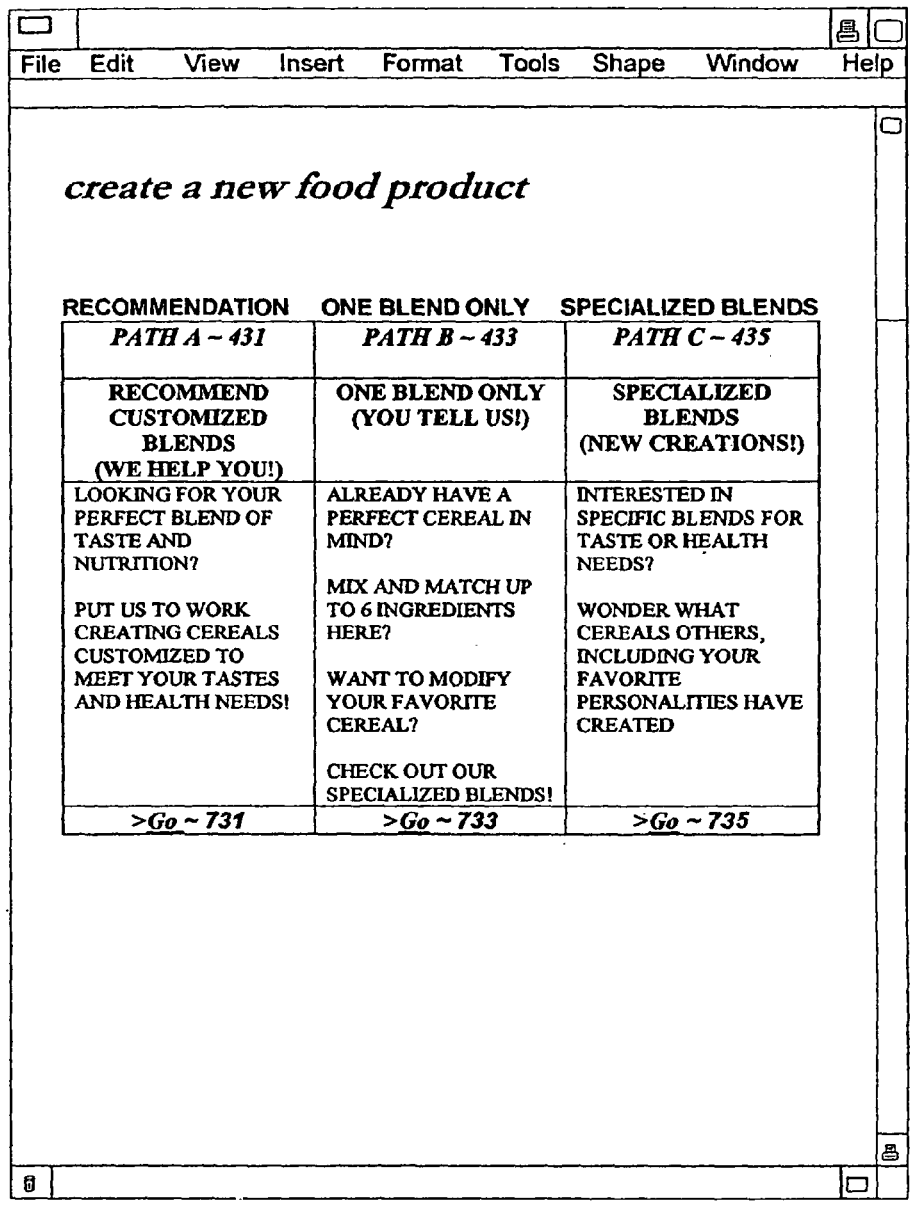
FIG. 7 is a sample Web page showing one embodiment of a "create a new food product" page having a recommendation path A, a one blend only path B and a specialized blends path C.

The "create a new food product" page 424 shown in FIG. 7 provides one example of a page a user might encounter if he selects the "create a new food product" link 624. In this embodiment, the user is presented with three choices or paths, as noted above, Path "A" 431 (Recommendation Path), Path "B" 433 (One Blend Only Path), Path "C" 435 (Specialized Blends Path). In another embodiment, the user may be presented with only two choices, such as a "create a new food product" choice and a "customize an existing food product" choice.

Figure 8:
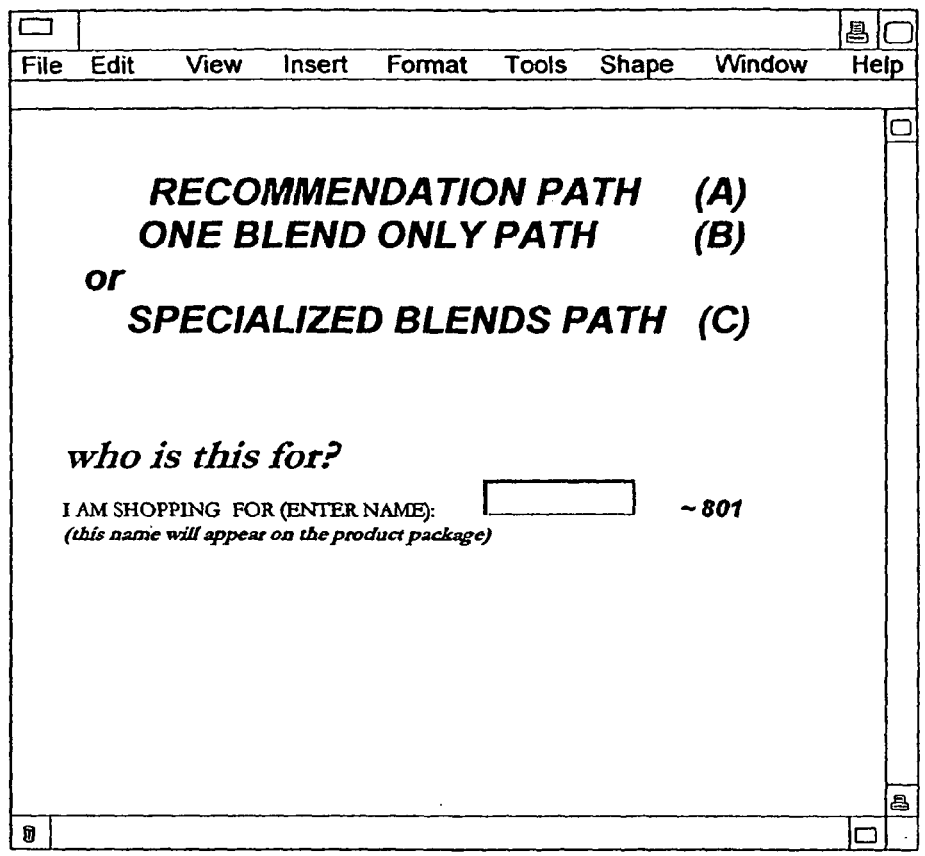
FIG. 8 is a sample Web page showing one embodiment of a "who is this for?" page that is viewed on Paths A, B or C.

The example Web pages shown in FIGS. 8-9 are the screens or Web pages which would be seen by the on-line consumer if the Recommendation Path "A" 431 or the One Blend Only Path "B" 433 is selected. These Web pages seek to determine some basic information about the particular consumer who will be eating the food product. This is to ensure that the recommended products meet the special needs of different categories of consumer.

FIG. 8, for example, shows one embodiment of the "who is this for?" page 426. In this embodiment, the user is asked to enter the name of the person who will be eating the food product into box 801. In one embodiment, this can be just a single word, such as a person's first, middle or last name. If a person uses both the first and middle names, this can also be entered, as can the person's entire name or any identifier the shopper desires, although in most embodiments the total number of characters will be limited. In the embodiment shown in FIG. 8, the user is informed that this is the name that will appear on the packaging. For example, if the name "Jimmy Miller" is entered into box 801, the customized food product is personalized with this name. If the food product is a cereal, for example, the outside of the cereal package can include the words "Jimmy Miller's Cereal." In other embodiments, just one name is used, e.g., "Jimmy's Cereal," or a two-part name, e.g., "Laura Jean's" Cereal," and so forth. The user also has the option, once the product is designed, to pick an additional unique title for the cereal, if desired, as described in FIG. 16. In an alternative embodiment, the "who is this for?" page 426 can include other questions, such as questions relating to gender and age as described below in FIG. 9.

Other questions designed to create a user profile can seek to determine lifestyle issues such as family size, geographic location, family history, and so forth. Lifestyle issues can include, for example, an overall determination of the current stress level for the consumer based on responses to a questionnaire on recent major life events, general responsibilities, work environment, and so forth, so that advice can be offered as to how to improve general quality of life, reduce stress, and so forth. Geographic location information can help the merchant provide the consumer with proper health and nutrition advice during the various seasons. General family history information can help the merchant provide the consumer with information relating to inherited diseases and possible preventive action the user can take. Questions as to preferred language can also be asked, with the user given the option to view the website in the language of their choice, e.g., Spanish, French, German, etc. In an alternate embodiment, this option is presented immediately to the consumer through a button or link available on the "home/log-in" page 402.

FIG. 9 shows one embodiment of the "about me" page 428 in which the user is asked to identify the gender 903, age 905, known food allergies 907, serving size preference 909, special diets 911 and preferred packaging form 913 for the intended recipient of the customized food product. In other embodiments, additional and/or alternate information is sought. The information can be provided by the user by clicking on the appropriate buttons or links. In an alternative embodiment, information is typed in or entered by any other known means or combination of means as discussed herein.

In a preferred embodiment, an additional precaution for those with diabetes is also noted. In one embodiment, it is suggested that a diabetic consult with a registered dietician for an individualized food plan.

Section 907 of FIG. 9 provides one example of a list of foods that the user can choose from to indicate that he needs to avoid them. In this embodiment, the choices are peanuts, other nuts, e.g., almonds, pecans, walnuts, hazelnuts, macadamia nuts, eggs, soy, wheat, dairy products. The user can also indicate that he has no food allergies or adverse reactions. Preferably the user is required to mark at least one box in this section before proceeding to the next Web page.

In other embodiments additional or fewer categories can be included. Such additional categories can include, but are not limited to, fish, corn, caffeine, chocolate, carbonated beverages, and so forth. In one embodiment, subcategories are also given. For example, a consumer may not be allergic to all fish, but just to one particular group, such as shellfish, or a specific kind of seafood, such as shrimp.

It will be appreciated by those skilled in the art, that not every reaction to a food is an "allergy," although it is still a food that the consumer may wish or need to avoid for any number of reasons. Such reactions can include any type of intolerance for any reason, due to lack of a particular enzyme, for example. Many athletes avoid carbonated beverages in order to improve performance. The adverse reaction may also be dose related, such that the consumer can tolerate a certain level of this food during one period of time with no adverse effects. Various non-allergic adverse systemic reactions can include symptoms such as diarrhea, cramps, nausea, bloating, heart palpitations, migraine headaches, breast tenderness, hyperactivity, and so forth. Excess use of some foods, such as teas, which contain tannic acid, are considered by some to be related to an increased incidence of bladder infections.

In one embodiment, there is a place for the user to type in a name of a particular food, such as corn, which that user knows to have an adverse affect on him or perhaps on his child. If desired, the user can specify that all products associated with corn, for example, be avoided, which would include any ingredients or additives that contain any corn by-products, sweeteners with corn syrup, and so forth. The person can also be given the option to seek information on alternate words for the same food in order to ensure it is being avoided in all food products, or limited, as intended. For example, some consumers may not realize that terms such as dextrose, maltodextrose, dextrin and modified corn starch, all refer to corn by-products. As a result, they may be unknowingly providing this to their child or ingesting this themselves, when, in fact, they should be avoiding it. Additional information can also be provided in a link located near each term on the website or the term itself can be a link to additional information. In one embodiment, a pop-up box appears when the mouse cursor is placed over a particular word or nearby link. For example, if a consumer selects caffeine, but not chocolate, as a possible food to avoid, a pop-up box can appear providing information that chocolate also has caffeine and asking the user to consider whether chocolate should also be avoided. In one embodiment, there are links to other, more detailed sources of information.

Perhaps the person believes himself to be lactose intolerant. In this embodiment, the person may select the "no dairy products" option, when, in fact, they only need to avoid or limit milk sugar and not milk protein fractions or milk fat fractions. In one embodiment, the user can be provided with additional information or links to additional information, as noted above, to clarify which products actually contain lactose. For example, it is a common misconception that all dairy products contain lactose, when in fact some fermented dairy products and butter do not contain problematic levels of lactose. In this way, the user can be guided to not unnecessarily avoid certain food products. The person can also be quizzed as to the reason for selecting various diets, to ensure that the consumer is fully and accurately informed as to the need for such diets, as well as the possible ramifications for being on such a diet. For example, for the person who chooses the "no dairy products" option, special information can be given, particularly for females, of the need to seek calcium from other sources. Likewise, a consumer seeking a "contention's" diet, such as a high protein, high fat, low carbohydrate diet, may be offered a range of opinions and information on the relative merits and risks of this type of diet.

Any appropriate ranges and sizes can be offered as an individual serving in order to better meet the nutritional needs of the individual consumer. The serving size preference 907 selections in the embodiment of FIG. 9 are shown below in Table 1. In a preferred embodiment, an additional precaution for those with diabetes is also noted.

TABLE 1

INDIVIDUAL SERVING SIZE CHOICES

| Small (for small appetites) | Medium (for moderate appetites) |
|---|---|
| About 1 cup | 1-1½ cups |
| About 1¾ ounces | About 2 ounces |
| 120-180 calories | 180-250 calories |
| Large (for hearty appetites) | Extra Large (for cereal lovers!) |
| 1½-1⅞ cups | 1⅞-2¼ cups |
| About 3 ounces | Over 3 ounces |
| 250-320 calories | 320-400 calories |

Various special diets can also be accommodated in order to better meet the nutritional needs of the individual consumer. The exemplary special diets noted in the special diet section 911 in FIG. 9 are shown below in Table 2.

TABLE 2

INDIVIDUAL SERVING SIZE CHOICES

| No special diet | Diabetic |
|---|---|
| Vegetarian | Low cholesterol, low fat |
| Low/No Salt | Athlete-in-training (high carbohydrate) |
| Weight Watchers ®/Jenny Craig ® | Atkins ® |

Figure 23A:
FIGS. 23A-23C are diagrams showing embodiments of single-serve consumer packaging.
Figure 23B:
Figure 23C:
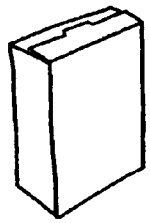

As FIG. 9 shows, the user can also be given the opportunity to select the preferred packaging form 913, such as a bowl, pouch or box (See FIG. 23A-23C). In another embodiment there are fewer or more options, such as just a bowl or a pouch.

The example Web pages shown in FIGS. 10-16 are the screens or Web pages which would be seen next by the on-line consumer who is on the Recommendation Path "A" 431 (from FIG. 7). Essentially, the Recommendation Path "A" 431 allows a fully customized product to be developed for a user based on their responses to a survey that can include questions pertaining to health concerns and/or conditions, taste preferences, and so forth, as well as lifestyle issues, stress management issues, and so forth. Depending on the responses given by the consumer, the recommended customized food products can focus on or emphasize certain areas. For foods such as cereals, for example, customization can be accomplished by adding new flavors, vitamins, minerals, soy nuts, fiber, fruits, and so forth, to known cereals, favorite cereals or an entirely new cereal can be created from scratch.

In one embodiment, all of the recommendations focus on a particular area, such as health, taste, a balance of health and taste, or a combination thereof. In another embodiment, the user is presented with a number of recommendations, each emphasizing a different area In a specific embodiment, the user is presented with one choice in each particular area, such as one healthy choice, one tasty choice and one balanced choice. Essentially, the surveys described to this point use indirect or inductive reasoning, i.e., proceeding from particular facts to a general conclusion. In one embodiment, however, an "inferential" survey based on inferential reasoning is used, i.e., proceeding from general premises to a necessary and specific conclusion. Such an inferential survey can be used, for example, to determine taste preferences, i.e., to determine, by inference, qualities and/or taste attributes the consumer enjoys. In such a survey, various "diagnostic" questions are asked from which formulation information can be inferred. For example, rather than having the consumer select specific categories or additives (i.e., determining general preferences based on particular facts), the consumer is asked if he or she enjoys spicy foods, Chinese foods, chocolate, sweets, and so forth (i.e., determining specific preferences based on general information). In this way, a customized food product can be developed that can meet the special tastes of each consumer.

In one embodiment, a cautionary statement can also be given in order to clarify the extent of services that the Web site offers. An exemplary cautionary statement might read, "The Personal Health and Taste Profile questions have been developed to customize a food product to your unique needs and preferences. Your responses to these questions will be used to individualize a food product specifically for your dietary regimen. Individualized food products are not intended to diagnose, cure, mitigate, treat, or prevent disease. If you have a disease or health-related condition, consult a health professional." In other embodiments, such a cautionary statement can also or alternatively appear elsewhere, such as on the "home/log-in" page 402 (FIG. 5) or any other Web page.

In one embodiment, a general overview of the reasoning behind asking such questions is given. An exemplary overview statement might read, "Healthy and delicious. With all these options, you can have both. Tell us about all the flavors and textures <NAME> (from FIG. 8, 801) likes most. We'll develop blends using different combinations of the ingredients you choose. We hope you find one that's perfect for you. Click on any ingredient below to see its picture and description."

In order to determine taste preferences, detailed information can be sought as to a variety of topics, depending on the food product to be customized. In one embodiment, a series of categories is presented from which the user can select all that apply. With cereal, for example, questions can be asked as to cereal preferences, including form, ingredients, flavors, additives and sweetness levels.

An exemplary "ingredient" list for a customized cereal product might include wheat, soy, corn, multi-grain, rice oats and bran. An exemplary "flavor" list might include natural (toasted), honey, honey and nuts, cinnamon, chocolate, frosted, fruit flavors and nutty flavors, as well as examples of flavors noted in the definition section herein. An exemplary "additives" list might include particulates, such as raisins, walnuts, raisin nuts, pecans, almonds, yogurt chips, blueberries, banana chips, apple chunks, strawberries, cranberries, dark chocolate, macadamia nuts, milk chocolate, coconut, peaches, raspberries, apricots, honey nut clusters, malted milk balls, marshmallow bits, tropical fruit and chocolate raisins, as well as examples of additives noted in the definition section herein. An exemplary "sweetness level" list might read, "not at all," "only slightly sweet," "moderately sweet," "very sweet," "show me a range." In another embodiment, alternative descriptive language is used and can include more precise language. In yet another embodiment, the categories are grouped differently. For example, fruit particulates, including dried or freeze-dried fruits can be included in a separate category (See FIG. 10B, 1008, for example).

Figure 10A:
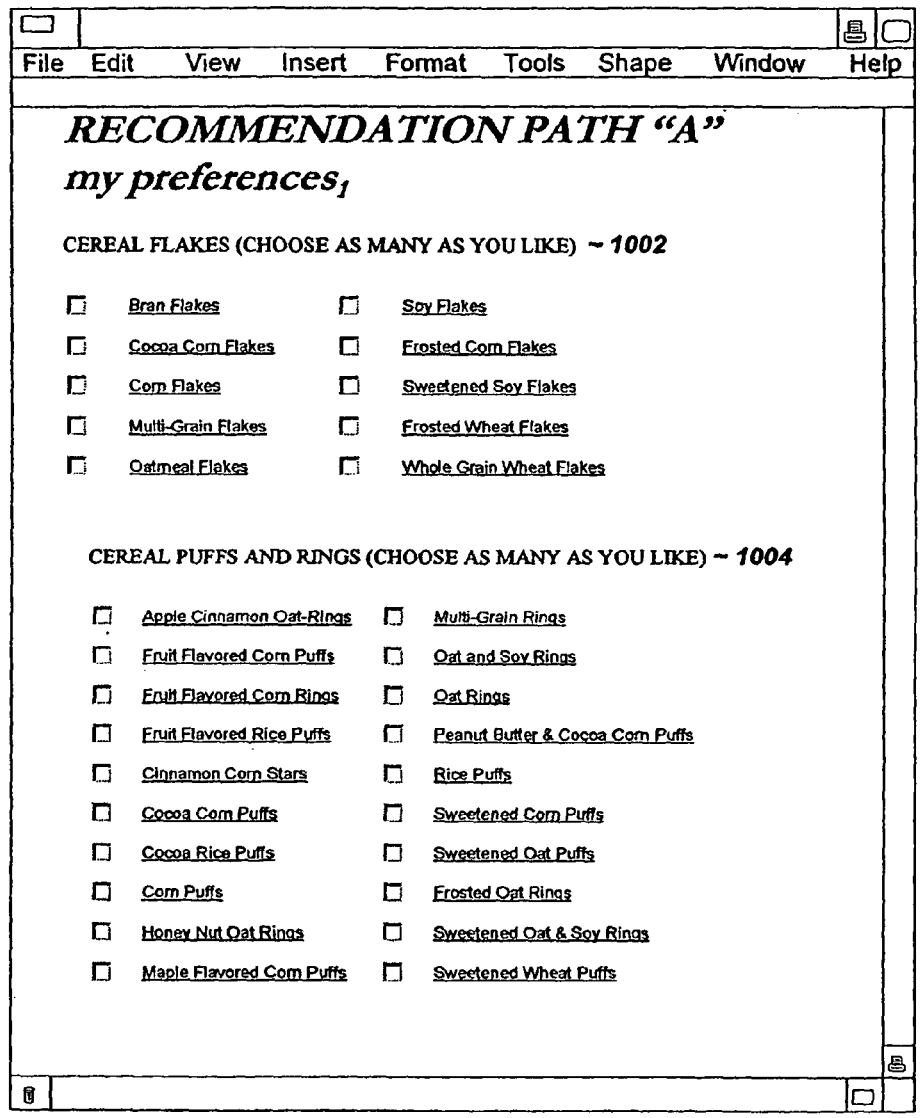
Figure 10C:
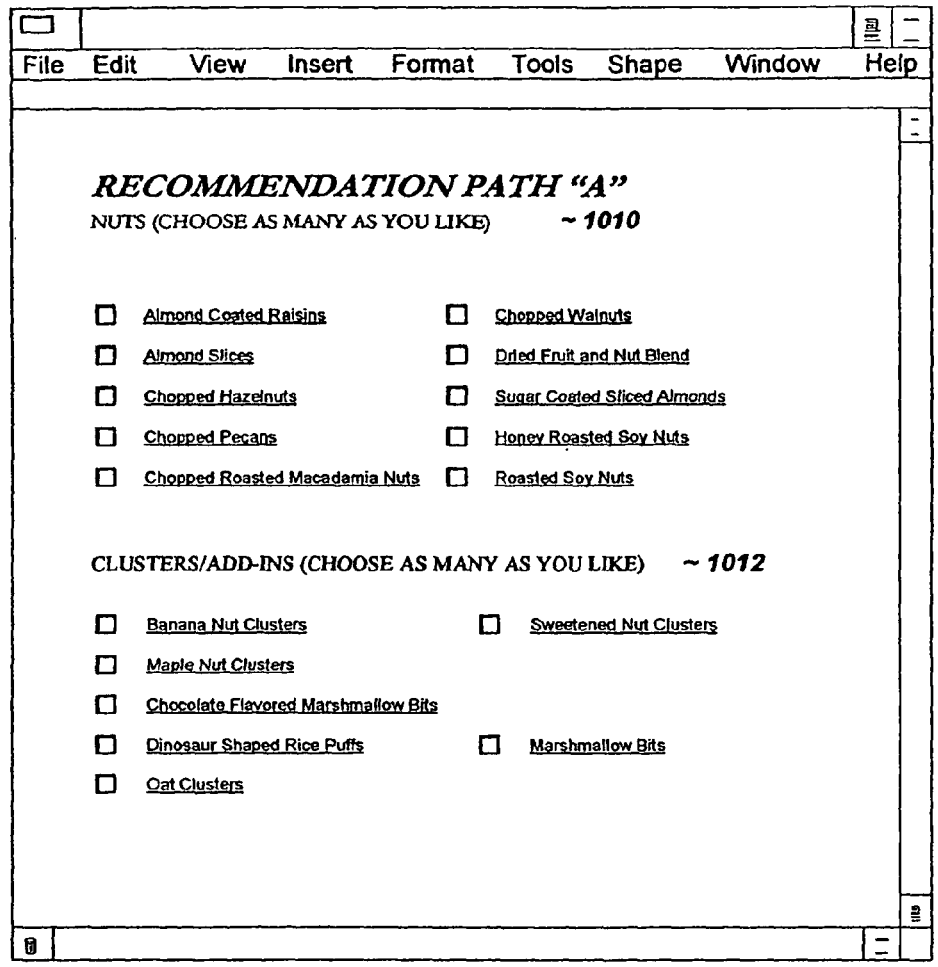

FIGS. 10A-10C provide one example of how taste preferences for a cereal product can be determined. As shown in Web page 430A (FIG. 10A), there is a "cereal flakes" section 1002 and a "cereal puffs and rings" section 1004. Web page 430B (FIG. 10B) has an "other cereal forms" section 1006 and a "fruits" section 1008. Web page 430C (FIG. 10C) has a "nuts" section 1010 and a "clusters/add-ins" section 1012. In each instance, the user is invited to select as many options as they would like to in each section, e.g., by clicking on more than one button.

In one embodiment, an exemplary brand name is provided together with the form to help the consumer better identify the named form. For example, the term "puffs" can be followed by "e.g., Kix®," the term "rings" can be followed by "e.g., Cheerios®." Similarly, the term "strings" can include "e.g., Fiber One®," the term "sweet treats," can include, "e.g., Trix®, Lucky Charms®, or Cocoa Puffs®," and so forth. (In the examples contained herein, all of the brand names given are owned by the Assignee, General Mills, Inc. in Minneapolis, Minn.). Other additional terms can also be used, such as the familiar term, "shredded wheat" following "shreds."

In this example, the "cereal flakes" section 1002 shown in FIG. 10A, include bran flakes, cocoa corn flakes, corn flakes, multi-grain flakes, oatmeal flakes, soy flakes, frosted corn flakes, sweetened soy flakes, frosted wheat flakes and whole grain wheat flakes, although the invention is not so limited. As noted above, different and/or additional categories for forms may be included, e.g., strings, sweet treats, and so forth.

The exemplary "cereal puffs and rings" section 1004, also shown in FIG. 10A includes apple cinnamon oat-rings, fruit flavored corn puffs, fruit flavored corn rings, fruit flavored rice puffs, cinnamon corn stars, cocoa corn puffs, cocoa rice puffs, corn puffs, honey nut oat rings, maple flavored corn puffs, multi-grain rings, oat and soy rigs, oat rings, peanut butter & cocoa corn puffs, rice puffs, sweetened corn puffs, sweetened oat puffs, frosted oat rings, sweetened oat & soy rings and sweetened wheat puffs, although the invention is not so limited.

The exemplary "other cereal forms" 1006, shown in FIG. 10B, includes toasted cinnamon multi-grain squares, cinnamon graham squares, corn squares, high fiber bran shreds, honey nut multi-grain squares, honey graham squares, multi-bran squares, multi-grain granola, multi-grain museslix, rice squares, wheat biscuits, wheat nuggets and wheat squares, although the invention is not so limited.

The exemplary "fruits" section 1008, also shown in FIG. 10B, notes that all fruits are dried or freeze-dried and includes apple slices, raisin apple prune bits, banana bits, cinnamon apple slices, coconut bits, cranberry bits, golden raisins, mango bits, peach bits, whole cranberries, pineapple bits, raisin date bits, raisins, raspberry bits, strawberry bits, sweetened date bits, toasted coconut bits, whole blueberries and whole cherries, although the invention is not so limited.

The exemplary "nuts" section 1010, shown in FIG. 10C, includes almond coated raisins, almond slices, chopped hazelnuts, chopped pecans, chopped roasted macadamia nuts, chopped walnuts, dried fruit and nut blend, sugar-coated sliced almonds, honey roasted soy nuts, roasted soy nuts, although the invention is not so limited.

The exemplary "clusters/add-ins" section 1012, also shown in FIG. 10C, includes banana nut clusters, maple nut clusters, chocolate flavored marshmallow bits, dinosaur shaped rice puffs, oat clusters, sweetened nut clusters marshmallow bits, although the invention is not so limited. In other embodiments a variety of uniquely shaped clusters/add-ins are available, such as other animal shapes, e.g., polar bears.

In one embodiment, the survey continues with questions pertaining to health issues and concerns, in which information on specific health conditions is sought. A statement preceding the choices can note that family history of a particular health problem may indicate a higher risk of developing that health problem and may provide a good reason to be concerned about it. The next screen for the user on the Customization Path "A" 431 (See FIG. 4), is the "my health" page 432, as shown in FIGS. 11A and 11B.

FIGS. 11A and 11B provide one example of how health issues can be addressed. As shown in Web page 432A, there is a "general health concerns" section 1102 and "food supplements" section 1104. As shown in Web page 432B, there is a "just for women" section 1104, "lifestyle" section 1106 and "eating habits" section. In each instance, the user is again invited to select as many options as apply or, in some instances, click the appropriate button to indicate "yes" or "no," or perhaps to indicate a particular range.

In this example, the "general health concerns" section 1102 shown in FIG. 11A includes colon cancer, constipation/desire extra fiber, diabetes, high blood pressure, high blood pressure, high blood cholesterol, heart disease or coronary artery disease, arthritis, weight loss/weight management, high blood cholesterol or heart disease, electrolyte loss (diarrhea, athletic training, etc.), energy, osteoporosis or bone health, pregnant or nursing, menopause, digestive problems, frequent colds or influenza, migraine headaches, memory loss, insomnia and none of the above, although the invention is not so limited. In an alternative embodiment, additional health conditions are covered and/or additional details as to these particular health conditions are also sought. For example, digestive problems can include separate categories for particular problems such as irritable bowel syndrome, acid reflux disease, and so forth. The "osteoporosis or bone health" category can also include categories such as weak teeth and/or can refer instead to concerns pertaining specifically to calcium deficiency. Again, alternative embodiments can include the option to type in additional information.

In another alternative embodiment, more detail as to the contents in the final product is given, depending on the category chosen. Table 3 provides examples for a few health concerns.

TABLE 3

CUSTOMIZED PRODUCTS FOR PARTICULAR HEALTH CONCERNS

| Health Concern | We will create one or more cereals for you that contain . . . |
|---|---|
| High Blood Cholesterol/ Heart Disease | Soluble fiber from oats, antioxidant vitamins C and E, vitamin B6, folic acid, vitamin B12. Limit sugar/carbohydrate content. |
| High Blood Pressure | Soluble fiber from oats, antioxidant vitamins C and E, vitamin B6, folic acid, vitamin B12. |
| Colon Cancer | Fiber, antioxidant vitamins C and E |
| Constipation/Desire Extra Fiber | Fiber, and other important nutrients |
| Diabetes | Fiber, antioxidant vitamins C and E, vitamin B6, folic acid, vitamin B12. |
| Osteoporosis | Calcium, vitamin D, magnesium, vitamin C |
| Pregnant or Nursing | Fiber, high levels of B vitamins, antioxidant vitamins C and E |
| Menopause | Fiber, high levels of B vitamins, antioxidant vitamins C and E. |
| Energy | Fiber, antioxidant vitamins C and E, B-complex vitamins, magnesium, zinc. |

The "food supplements" section 1104 shown in FIG. 11A includes prenatal vitamins, other (specify), herbal supplements (specify) and multivitamins, although the invention is not so limited. The necessary details can be supplied by typing in the appropriate information in a data entry field. Again additional and/or alternate categories can be used.

The "just for women" section 1106 shown in FIG. 11B includes questions regarding health issues unique to women. This section can include questions that may not have already been asked, such as in the "general health concern" section 1102. In this embodiment, a "yes" or "no" button is selected as to whether the consumer is currently pregnant or trying to become pregnant, lactating, or experiencing any symptoms of menopause, although the invention is not so limited. Alternately, the "just for women" section 1106 can be used as a supplement to the questions addressed in section 1102, such that an affirmative response to a question regarding women's health can link the user directly to this section to supply further details. For example, if the user has indicated in section 1102 that she is pregnant or nursing, the "just for women" section 1106 can have questions designed to learn more about the pregnancy, i.e., number of weeks, first pregnancy or not, past miscarriages, and so forth.

In another embodiment, there is a special "just for men" section asking questions unique to men's health, "just for infants," "just for toddlers," "just for children", "just for teenagers," "just for young adults," "just for athletes," "just for diabetics," and so forth.

The "lifestyle" section 1108 also in FIG. 11B seeks yes or no answers as to whether or not the user exercises at least three times a week, is a serious athlete, and/or smokes, although the invention is not so limited. Again, alternative embodiments can explore this type of information in greater detail and also seek information on other aspects regarding lifestyle.

The "eating habits" section 1110 also shown in FIG. 11B asks the user how many servings of certain foods are eaten each day. The user is also asked how many servings of particular foods are eaten per day. In this example Web page, the user can select a button for "zero (0) or one (1)," another button for "two (2) or three (3)," and another button for more than four "(4+)" servings. The particular foods listed include: calcium-rich foods, fruits, vegetables, "cereals, breads and grains," and "meat and eggs." In an alternative embodiment, other choices as to types of foods and/or number of servings are used. There can also be a link to more information to help the user determine what constitutes a "serving," what foods contain certain elements, e.g., calcium, and so forth After completion of the above-described survey, the user can proceed to the "multiple recommendations" pages 434A and 434B as shown in FIGS. 12A and 12B. In another embodiment, completion of the survey results in a survey summary, such as a "your nutrition information" page. In one embodiment, this information can be accessed from any page and in one embodiment is included on "my home page" 410 described above in FIG. 6.

Such a statement might read:

Survey Summary:
"Customizing a food products for your specific health needs depends on how much information we have. At present we only know you are a man in a particular age group. Knowing this, we would formulate food products for you that would:
Provide a good basic level of vitamin and mineral nutrition.
Provide lasting energy by incorporating complex carbohydrates, B-vitamins and soy protein. Your ability to respond well to stress may also be improved by these nutrients.
Maintain a healthy immune system with Vitamins C and E, beta-carotene, zinc and selenium.
Maintain healthy blood pressure by avoiding excessive salt. A recent study also suggests that getting plenty of Vitamin C can help maintain lower blood pressure.
Reduce the risk of colon cancer by being a good source of insoluble fiber. There is some scientific evidence that Vitamins A and E may also help.
Reduce the risk of heart disease by avoiding excessive salt and fat, and by providing a good source of soluble oat fiber. There is some evidence that Vitamins E, C, $B_6$, $B_{12}$ and folic acid may be helpful."

Obviously, the type of information provided will vary considerably, depending on the user's responses and also as a function of advances in nutritional science and medicine. Specifically, the nutrition information in the "survey summary" can be updated as new studies become available regarding known treatments for various diseases and/or preventative medicine. In alternative embodiments, more or less customized nutritional information and suggestions are provided. As such, the merchant can customize as much as possible based on the information provided, i.e., if the merchant only knows the consumer's gender, the merchant can provide information and a customized food product having a gender-oriented health profile, such as higher calcium and iron for a woman. If more information is provided by the user, i.e., concern about heart disease, and so forth, other components, both micronutrients and macronutrients, for example, can be added or reduced as needed. In one embodiment, the consumer need only complete the survey once, or alternatively, the survey can remain current for a period of time before it expires. In this way, the user does not have to complete the survey every time they log on to the website to place a customized order. In one embodiment, the merchant server prompts the user to update his survey after expiration of a period of time, e.g., update marital status, health concerns, and so forth. In one embodiment, the consumer does not need to update age information, as this is automatically updated each time he logs on, based on a previously-provided date of birth. In another embodiment, the merchant advises the consumer that his profile will be deleted if there is no usage after a certain period of time, e.g., 12-18 months.

In one embodiment, the survey summary and other information described above can periodically be sent via e-mail to the user, if desired. In an alternative embodiment, the information can be sent via any means, such as via facsimile, mailed in hardcopy form, and so forth. In one embodiment, there is a link to other health information, such as the "what's new?" page 428 noted in FIG. 4, that provides links to other health-related sites, chat rooms, Web site news and updates, and so forth, as described above.

In one embodiment, the user proceeds to a "multiple recommendations" page (434A and 434B), i.e., FIGS. 12A and 12B, as noted above. In this example, there is a custom blend one 1202, custom blend two 1204 shown in FIG. 12A and a custom blend three 1206 shown in FIG. 12B. In other embodiments, fewer than three choices are given, such as two or one, for example, if the user indicated so few taste preferences that it was not possible to create three or even two different choices. In one embodiment, the merchant can choose one or more components that may not be the consumer's first choice, but closely approximate the first choice, i.e., "related" components. In this way, the taste and health needs of the consumer are still being met, but the merchant has more flexibility with regard to the components in order to best meet conflicting needs, i.e., conflicting health and taste needs, and optimize taste and health needs. Other reasons may include the ability to ultimately provide a superior product, lower cost product, product having a faster delivery time based on component availability, and so forth. For example, mueslix can be substituted for granola, bran flakes might be substituted with whole grain wheat flakes, and so forth components that, i.e., "related" components, e.g., substituting muselix for granola (In one embodiment, however, the concept of "cousin numbers" is used in the software that drives the Web site to produce additional recommendations. "Cousin numbers" describe various properties of the ingredients that make up the customized food product. In this way, the merchant can change serving sizes, for example, without making appreciable changes in product identity and fortification levels).

The "fully customized recommendations" page 434A can also include a brief summary indicating what steps the user can take at this point and/or including reasoning behind the selections being offered. An exemplary statement might read, "Here are the cereals you've created. Because you checked high blood pressure and diabetes, we're recommending one or more cereals with soluble fiber from oats, antioxidant vitamins C and E, vitamin B6, folic acid, vitamin B12.If you're happy with your cereal, you can save it by clicking 'Save This Cereal (and add to My Basket)' below the recommendation." Other information might include special cautionary statements with respect to certain contents. For example, the statement in FIG. 12B reads, "Some of our fruits may contain sulfites. If concerned, please click on "Complete Nutrition" for the blend you select."

As shown in FIGS. 12A and 12B, each blend or recommended food product can be identified in any number of ways, such as by its primary ingredients 1201. The description can further include an allergen statement 1203, noting if the product contains any potential allergens. In another embodiment, content information is also provided with respect to foods this consumer may have an adverse reaction to, according to their own survey. Each blend can further include nutrition highlights 1205 as shown. For each of the choices given, the user can choose a "save this cereal/and add to my basket" link 1244. This link essentially allows the user to add the selected product to his basket or shopping cart as is. When this action is taken, the user is sending a request to the merchant server to add the item to a "shopping cart." Other links include a "detailed ingredients/nutrition panel" link 128, "modify cereal" link 1240 (i.e., customize further) and a "pricing" link 1246, although the invention is not so limited. Other links, shown in FIG. 12B, include a "compare cereals' nutrition" link 1236 (FIG. 13) and a "start over" link 1210, which, in one embodiment, takes the user back to the "create a new food product" page 410 described in FIG. 7. Additional choices can also be provided on subsequent Web pages, which can be viewed by clicking on the "see more choices" link 1234 shown in FIG. 12B. In one embodiment, the user can choose to view up to three additional choices at a time.

The sample Web pages 434A and 434B shown in FIGS. 12A and 12B provide recommendations for cereals and cereal blends that are designed to match the nutritional and taste preferences of the user, i.e., a customized cereal "solution." As noted above, however, similar recommendations can be provided for virtually any type of food product, resulting in a nearly limitless number of "customized food products," as defined herein.

Aside from the sample customized cereals shown in FIGS. 12A and 12B, other sample recommendations for cereals might include a recommendation for a "high protein fruit and nut blend" cereal. A description of this cereal might state that it is, "a delicious combination of whole grain corn and wheat flakes mixed with crispy soy nuggets, macadamia nuts, sweet cranberries and tender pieces of dates. This cereal is a good source of soy protein and fiber and is fortified with 12 key vitamins and minerals in a blend optimized for you."

A "blueberry supreme cereal" might be described as,

"a delectable combination of multigrain shredded cereal mixed with whole blueberries. Fortified with extra calcium and soy protein, this cereal is a good source of fiber, a good source of soy, and also contains twelve other vitamins and minerals in a blend optimized for you."

A "multi-grain cereal and nut blend" might be described as,

"a delicious combination of whole grain corn and wheat Chex® mixed with crispy pieces of almonds and hazelnuts, all covered with a delicious clover honey coating. This cereal is an excellent source of fiber and is fortified with 12 key vitamins and minerals in a blend optimized for you."

As FIGS. 12A and 12B show, the unique interactive system of the present invention results in a one-of-a-kind and highly personalized menu from which the consumer can select. The added options of being able to learn additional information about the customized food product and/or to further customize the food product further enhance this unique selection process.

FIG. 13 is a sample Web page 438 that can be displayed when the user selects the "ingredients/nutrition" link 1238 for custom blend one 1202. As shown, a complete nutrition panel 1302, containing all the information the consumer is familiar with on conventional non-customized food products can be viewed.

If the user also or alternately prefers to compare the recommendations, he can click on the "compare " nutrition" link 1236 to view information, such as nutrition panels 1402, 1402 and 1406, side-by-side as shown in FIG. 14. In an alternative embodiment, the information is presented in table form, rather than as nutrition panels. In one embodiment, there is also a link to a comparison page in which any of the recommended customized food products can be compared with one or more competitor's products. In another embodiment, there is a comparison to one or more known product of the merchant's, with which the consumer is familiar.

For example, the "high protein fruit and nut blend" described above might be compared with a shredded wheat food product made by the merchant and/or a competitor. Such a comparison might reveal that other than also being a whole grain food product, the shredded wheat product in this instance is lacking in several aspects as compared with the suggested high protein fruit and nut blend. A specific statement might state, "The comparison product is not a multi-grain food product and further does not contain cranberries, macadamia nuts, B-vitamins, vitamin C, soy flour, soy protein or soy protein isolate, calcium, vitamin A, vitamin D, selenium, chromium or zinc."

Comparison information, such as information presented in table form, can also include pull-down menus to allow the consumer to make adjustments and modifications to their product at this point, in order to further customize the food product to suit his particular needs and/or tastes. For example, the consumer can choose to keep or remove cranberries, macadamia nuts and soy protein. In one example, the consumer can further choose to reduce the B-vitamins, vitamin C, calcium and vitamin A to 25% or 50% of the present content. In alternative embodiments, the consumer can keep, remove, add to or reduce ingredients using other proportions and percentages. In this embodiment, the consumer is provided with only limited choices in order to avoid creating a blend that is nutritionally incomplete or incompatible with regard to the ingredients or that fails rules set around "good taste" as is known in the art. (e.g., a spaghetti and chocolate combination, fish/cereal, etc.). Limiting choices also prevents creating combinations of additives that are incompatible and are known to adversely interact with each other during manufacture, packaging, distribution and/or storage. In one embodiment, choices are limited in order to prevent the user from inadvertently creating combinations that are currently owned by a competitor.

FIG. 15 provides another example of how a consumer may choose to modify his food product on a limited basis with the "modify" page 440. In this embodiment, the consumer can also select a unique name for their chosen customized food product. In other embodiments, this step is saved for the "save and name" page 442 as shown in FIG. 16. In the embodiment shown in FIG. 15, the "modify" page includes the ingredient list 1203 from the "fully customized recommendations" page 434A (FIG. 12A), a current add-ins list 1503, an available add-ins list 1507, packaging information 1511 and a data-entry box 1513 for naming the food product, although the invention is not so limited.

The current add-ins list 1503 can be followed by a "remove add-ins" link 1505, which the user can click on to remove a particular add-in. Similarly, the available add-ins list 1507 can be followed by an "add" link 1509 which the user can click on to add a particular add. In both instances, the user can repeat these actions as many times as desired, which in some instances may result in the same additive being removed and added back in and vice versa.

In this example, the consumer can also change packaging options 1511 from the one previously selected on the "about me" page 428 (FIG. 9) to another choice, e.g., from bowl to pouch. Once the consumer is satisfied with all of the changes, he can name the food product with a unique and distinctive name in the data entry box 1513. The name can perhaps be associated with a particular holiday, special occasion, favorite season, favorite vacation spot, or perhaps associated with a hobby, interest, sport, movie, music, career, or a humorous reference to a person who enjoys certain activities, etc., e.g., "Rocket Man's Fuel," "Discus Thrower's Special Blend," "Gardener's Variety Mix," etc. Virtually any descriptive or non-descriptive name can be used. In one embodiment, there are various filters, such as a filter to exclude known trademarks, offensive terms, number and type of characters, and so forth. The user can also be reminded here that the name entered in the "who is this for" page 426 (FIG. 8) will already be on the package, e.g., the outside label will contain the name, as described above.

Links to any other page can be given on the "modify" page 440. In the example shown in FIG. 15, there is a "save for later" link 1542, an "add to basket" link 1544, a "my home page" link 1510 (to FIG. 6), a "complete nutrition" link (to FIGS. 13A and 13B), a "cereal pricing" link 1546 and a "return to recommendations" link 1534 (to FIGS. 12A-12C).

In FIG. 16 the user can save and name their product as described in FIG. 15. The Web page 442 can also provide instructions, such as, "Now you can decide what you would like to name your custom food product blend. Just type in the name for your food product below. You need to name your food product in order to save it. Then, either add it to your basket for check out or save it for later (will appear in "My Home Page") as well as the "recommendation" page. From this page, as noted in the instructions, the user can click on the same links as shown in FIG. 15.

After saving and naming the food product, the user can access the actual ordering interface in which the consumer can order by the unit or serving, or in terms of a number of weeks' supply. It is to be appreciated that the ordering information can be presented and the consumer can click to transmit an order in any known way. Each customer can order more than one formula at a time, and the minimum order size can be established at any suitable amount, such as a one serving, one day, one week, two week supply, and so forth. Additionally, each household may choose to order varied formulas for individual family members. Any additional product and/or ordering information can also be provided to the consumer at this time and/or on any other page. In one embodiment, there is an explanation given as to the serving sizes, such as, "in order to ensure that the consumer receives exactly the right amount of vitamins and minerals, the portion size is controlled by using convenient single-serving packages."

FIG. 17 provides one example of an order interface with the "my basket" page 444. In this example there is a "your order" section 1702, an "increase portion" section 1704, "address" section 1706, "payment information" section, a "review privacy policy" link 1710, a "submit order" link 1712, as well as a "start over" link 1714, although the invention is not so limited.

In the "your order" section 1702 a summary of the order can be given including, a food description (i.e., name and serving size), packaging type, quantity, price per serving and total price. A single-serve package in this example contains about 1½ cups of cereal. (In another embodiment, a range is given, such as 1½ to 1⅞ cups for a "large" portion, as shown in FIG. 9). In this embodiment, the price is shown to be $1.09 per single-serve package or bowl. This price might be appropriate for a customized food product containing fruits and nuts or other similar ingredients. Cereals with less of these types of ingredients may cost less. In one embodiment, additional premium ingredients, such as a premium nut, i.e., macadamia nuts, are available for a surcharge.

In this embodiment, the user can click to increase their portion to a larger size, such as two (2) cups by paying an additional amount, such as about $0.25 extra, as shown in section 1704. In other embodiments, other larger or smaller sizes can also be ordered. In yet other embodiments, other last-minute changes and modifications can be made at the "my basket" page 444. In yet other embodiments, the consumer is not given the option to make changes here, but is instead directed to go back to the survey to resubmit a different response to the question on serving size (See FIG. 9) by clicking on the "start over" link 1714. The "your order" section 1702 also includes the total cost of the order, including any shipping and handling. Options for any type of expedited shipping can also be given.

The "payment information" section 1708 can include information as to the type of payment accepted, such as all major credit cards. If the user has a previously saved credit card, that can be used, or the user can enter the particulars of another credit card. Additionally, an unconditional money-back guarantee on all products can also be given here or any other location or page. In one embodiment, payment information is tied into third party shopping systems, e.g., Yahoo or AOL, such that the pertinent information (e.g., name, billing address, shipping address, credit card information, and so forth) is filled in automatically for the consumer.

The user can then proceed to the "billing and shipping" page 446 and a final checkout page 448 as is known in the art and described in FIG. 4. In other embodiments, the billing and shipping page 446 is skipped if the information is already known, and the user proceeds directly to a final checkout and thank you page. In one embodiment, the user may also receive a promise for an e-mail delivery of a receipt for their order. After a short time period, as described herein, the user receives the ordered product that has been custom designed just for them.

Figure 18A:
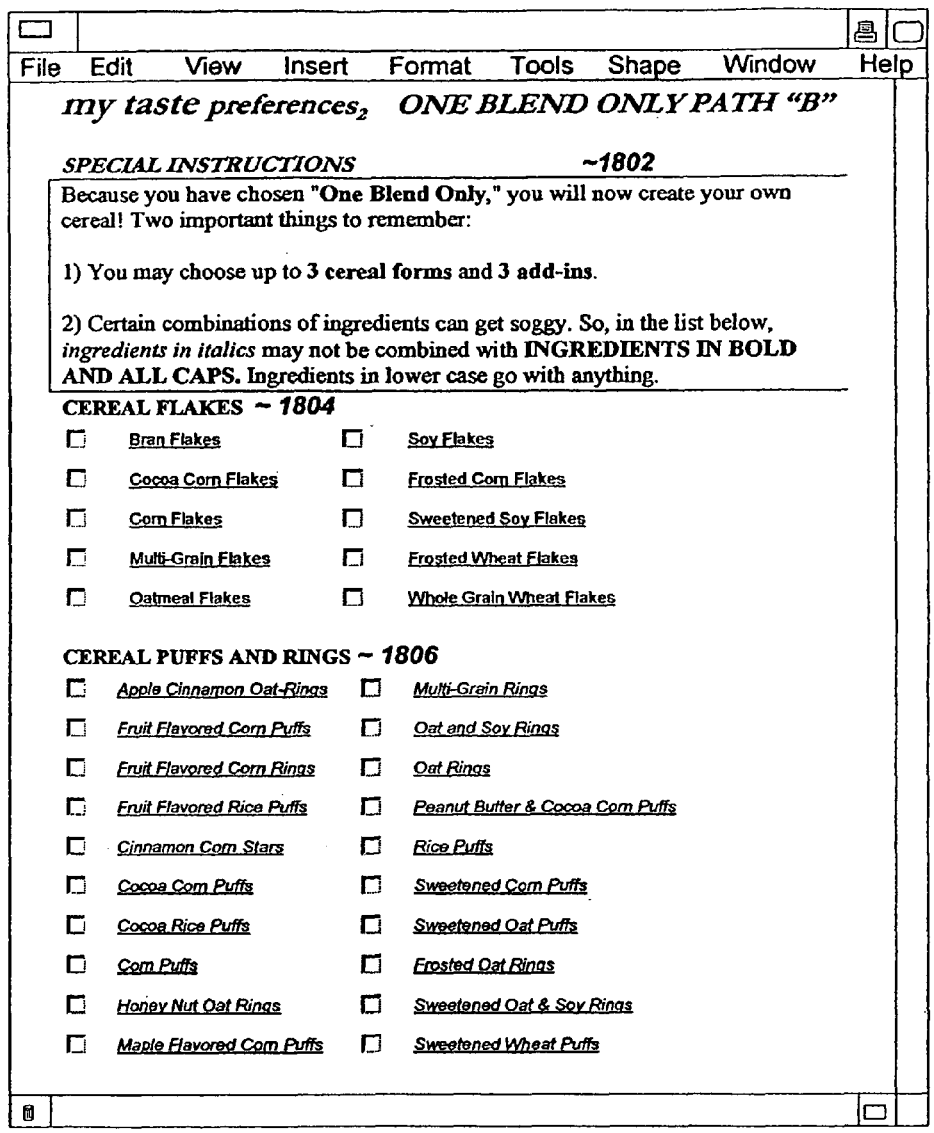
Figure 19:
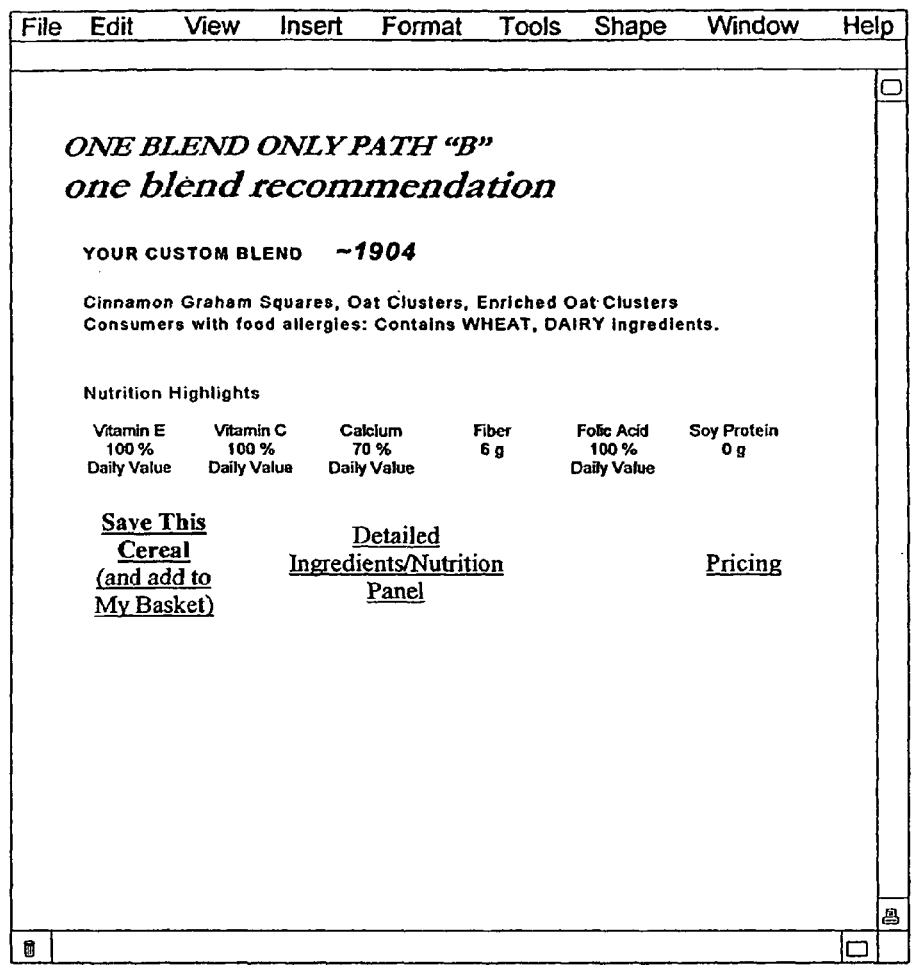
FIG. 19 is a sample Web page showing one embodiment of a "one blend recommendation" page viewed on Path B.

The example Web pages shown in FIGS. 18-20 are the screens or Web pages that would be seen after Web page 428 ("about me", FIG. 9) by the on-line consumer who is on the One-Blend Only Path "B" 433 (from FIG. 7). Essentially, the One Blend-Only Path "B" 433 speeds up the selecting and ordering process described above by limiting the number of choices and seeking answers to only a limited number of taste questions. However, the end result is a customized cereal designed especially for this particular user who may not need or want to seek all the nutrition and health advice offered on the Recommendation Path "A" but does not have a particular category in mind to follow the Specialized Blends Path "C."

Again, it is not possible in all cases to completely remove certain ingredients unless a specific additive or base is removed, if the additive or base contains that ingredient. For example, if the customized food product is a cereal, any ingredients contained in the cereal base cannot be removed unless the base cereal itself (puffed food product) is removed. If, however, the consumer desires to eliminate this ingredient, the option can be given to try another cereal base or combination of cereal bases.

FIGS. 18A-18C provide exemplary "my taste preferences (2)" pages 450A-450C, for the One Blend Only Path "B" which show various ingredients, i.e., additives, grouped in different categories, from which a consumer can select to produce a single customized blend of ready-to-eat cereal. As noted above, this path, as well as the other paths described herein can also be used to select a customized blend of virtually any type of customized food product. However, as in other embodiments, particular combinations are limited by health and taste "rules" or screens. In one embodiment, information is given to help the consumer understand such restrictions.

In the embodiment shown in FIG. 18A, the special instructions 1802 inform the consumer that he, "1) . . . may choose up to three cereal forms and three add-ins" and "2) Certain combinations of ingredients can get soggy. So, in the list below, ingredients in italics may not be combined with ingredients in bold and all caps. Ingredients in lower case go with anything." In another embodiment the ingredients are color-coded to communicate the proper groupings. In most embodiments, the software is designed to prevent the consumer from accidentally making improper combinations, e.g., if one or more ingredients from the "italics" group have been clicked and the user then clicks on an ingredient "in bold and capital letters," a pop-up menu appears to remind the consumer that this combination is not acceptable.

In the embodiment shown in FIG. 18A, the categories are cereal flakes 1804, cereal puffs and rings 1806, other cereal forms 1808, clusters/add-ins 1810, nuts 1812, fruits 1814 and brand name cereals 1816. As FIGS. 18A-18C show there is a wide selection for the consumer to choose from and most ingredients can be combined, with the exceptions clearly noted. For example, in this embodiment, none of the cereal puffs and rings 1806 can be combined with a number of the fruits, although the invention is not so limited. Similarly, most of the other cereal forms, other than wheat biscuits and wheat nuggets are not suitable for combining with these same fruits. However, all of the cereal flakes listed, as well as many of the clusters/add-ins and nuts are combinable with anything else on these pages. In one embodiment, familiar brand names are used together with the generic terms noted above.

FIG. 19 provides an exemplary "One Blend Recommendation" page 435 as described above. In this embodiment, the information given in the "your custom blend" section 1904 can be similar to the information described above for the multiple recommendations in FIGS. 12A and 12B. In the embodiment shown in FIG. 19 there is no option to modify further. However, in other embodiments, such as is shown in FIG. 4A, there is a modification feature available for the One Blend Only Path "B" 433, such that the user can proceed to the "modify" page 440 described above.

With the "click here to modify your favorite cereal" link 1811 shown in FIG. 18C, the user can customize name brand cereals by choosing various additives on an "alternate modify" page 1816 as shown in FIG. 20. In one embodiment, the additives are pre-screened as in the "modify" page 440 (FIG. 15) described above to avoid creating unacceptable blends. In the embodiment shown in FIG. 21, the user can choose from a wide selection of brand name cereals, together with a variety of particulates, including nuts, fruits and "sweet stuff" as shown in section 2108 of FIG. 21. In one embodiment, the consumer is requested to choose 1, 2, or 3 cereals, although the invention is not so limited. Examples of these cereals include Cheerios®, Total®, Kix®, and so forth. The user can also be requested to choose between 0, 1, or 2 "nuts, fruits and sweet stuff," and/or additional nutrients, although, again, the invention is not so limited. Additionally, the consumer can choose to add either some "standard" vitamins and minerals, which consist essentially of conventional antioxidants and fractions of a recommend daily allowance (e.g., ten (10)% RDA of all essential vitamins and minerals). The other vitamin and mineral choice might be a "personalized blend," as shown in FIG. 20, although a message associated with this blend also states that the health and nutrition survey needs to be completed first. In the embodiment described herein, the user would need to complete the survey presented in the Recommendation Path "A" 431 (pages 11A-11B). As FIG. 20 shows, the consumer can also add 0, 1 or 2 other nutrients, although the invention is not so limited. In this sample Web page, the choices for other nutrients include fiber (oat bran) clusters or soy protein clusters. After making his or her selection, the consumer can start over by clicking on the "clear" button. Alternately, the consumer can click on the "click here to save this combination" button. Alternately, the consumer can click on the "click here to create another combination" button. If the "save" button has already been clicked on, presumably the previous selection is saved and a fresh display is shown from which the consumer can customize another cereal or alternately, proceed to order and purchase the customized food product that has been designed.

Figure 21:
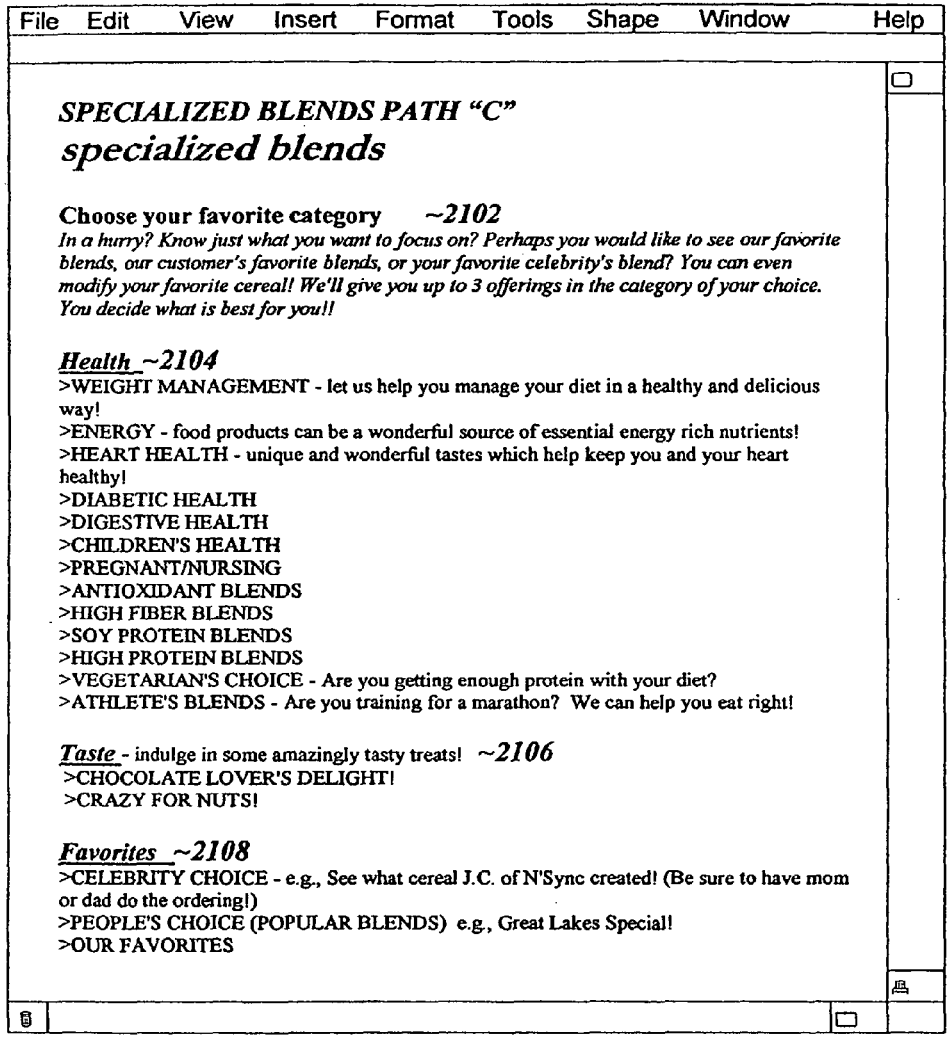
FIG. 21 is a sample Web page showing one embodiment of a "specialized blends" page viewed on Path C.

Finally, FIG. 21 is the Web page the user will see who has selected the "Specialized Blends Path "C" 435 at the "create a new food product" page 424 described in FIG. 7. This path essentially provides for "niche" marketing over the Internet. Path "C" may be appropriate for someone who knows he has heart disease and simply wants to be shown what options are available to help with this condition. In this way, the consumer is still designing his own customized food product by selecting which category of previously-designed customized food products to pursue. Furthermore, in some embodiments, the user can choose to further modify the previously-designed customized food products, (e.g., add a favorite taste ingredient to a Heart Healthy Specialized Blend, etc.), thus further enhancing the customization already offered in the Specialized Blends Path "C" 435.

After making his selection, the user can be greeted with an invitation to "choose your favorite category" 2102. In the embodiment shown in FIG. 21, the text reads, "In a hurry? Know what health or taste areas you want to focus on? Perhaps you would like to see our favorite blends, our customer's favorite blends or your favorite celebrity's blend? We'll give you up to three offerings in the category of your choice. You decide what is best for you!"

Any number and type of specialized blends can be included. In the embodiment shown in FIG. 21, the categories are health 2104, taste 2106 and favorites 2108. Exemplary health categories 2104 include, but are not limited to, weight management, energy, heart health, diabetic health, digestive health, children's health, pregnant/nursing, antioxidant blends, high fiber blends, soy protein blends, vegetarian's choice, and athlete's blends. Exemplary taste categories 2106 include chocolate lover's delight, crazy for nuts, although the invention is not so limited. Exemplary favorites categories 2108 include celebrity choice, people's choice, our favorites, and modify your favorite cereal, although the invention is not so limited.

For the "celebrity choice" category in section 2108, product choices/taste preferences of celebrities, such as athletes, musicians, actors, etc., can be displayed with or without specific personal endorsements.

After making a selection, the user proceeds, in one embodiment, to a page having information provided in the exemplary "specialized blends recommendation" pages 458A-458D shown in FIG. 22A-22D. Statement 2202 on exemplary page 458A states: "Heart Health—Because you checked Heart Health, we've shown you one or more cereals with soluble fiber from oats, antioxidant vitamins C and E, vitamin B6, folic acid, vitamin B12." Statement 2204 on exemplary page 458B states, "Energy—Because you checked Energy, we've shown you one or more cereals with fiber, antioxidant vitamins C and E, B-complex vitamins, magnesium, zinc." Statement 2206 on exemplary page 458C states, "Weight Management—Because you checked Weight Management, we've shown you one or more cereals with fiber, antioxidant vitamins C and E, B12 vitamins, and we have limited your calories, fat and carbohydrate exchanges." Statement 2208 on exemplary page 458D states, "Taste Treats—Great tasting with wonderful nutrition—what could be better? Your hardest decision is which one to pick!" After viewing and making their selection, the user proceeds as described above with saving, paying and checking out. In some embodiments, the name of the customized food product can be changed by the user, just for his own personal use, although the name on the Web site would remain as given.

As can be appreciated by those skilled in the art, the interactive and personalized nature of the present invention provides the consumer with "economic choice." In some instances, it may be important to budget and obtain the best value for the lowest cost. At other times, the same consumer may wish to "splurge" and purchase a product with little or no regard as to cost. This allows the consumer to purchase not only customized food products for everyday use, but also for those special occasions when the customized food product is to be given as a gift or in celebration of an event. This is unlike other systems in which the focus is to provide the product or service at the lowest cost, thus eliminating economic choice for the consumer. In one embodiment, the survey described herein also asks questions pertaining to economic preferences.

In one embodiment, the website also contains such a variety of food products that can be customized, as to essentially provide the means by which to customize a consumer's entire daily food intake. In this way a sufficient type and amount of customized food products can be selected, ordered and distributed so as to provide all the required daily allowance of nutrients for a particular individual. Menus can also be developed and customized to provide enhanced organoleptic benefits from a variety of customized foods. Further, by using the "virtual nutritionist/dietician" concept, a personalized menu can be developed which uses conventional prepared foods and/or ingredients that are readily available in conventional retail establishments, e.g., stores, restaurants, and so forth, as defined herein. As a result of the many unique features of the present invention, it is now possible, for the first time, to design a food product, such as a cereal or snack, with the form, flavor, extras, and nutrition that is "just right" for a particular consumer.

In one embodiment, the website also contains a "feedback" area or page. In this area, the consumer can rate or "score" a product as to a number of factors, including, but not limited to how well it was liked, what might be changed, how it made them "feel," and so forth. Written comments can also be given. Other consumers can then view this information, thus creating a type of "group commentary." A collection of scores can be analyzed according to any suitable statistical means, with scores "averaged" in various ways, charted, graphed, and so forth. In this way the interactive nature of the process is further enhanced. This type of information can also be sent periodically to the user via any means, such as via e-mail, hardcopy, or can be posted on their personalized "home" page.

In one embodiment, product choices collected over time are used to suggest new products, flavors, modifications of current brand name offerings sold through conventional channels of trade, e.g., grocery store distribution.

The packaging itself is also an opportunity to convey additional health and nutrition information to the consumer, as well as taste information. In one embodiment, additional information on how the customized food product can meet the taste preferences of a particular consumer is given, with less emphasis being placed on how the customized food product can meet the health and nutritional needs of a particular consumer. In yet another embodiment, any type of "customized" information, can be included in the packaging the consumer receives with his customized food product in the form of printed material. This information is relevant only to that consumer's needs, as the merchant understands them, and is a unique printout only for that consumer. In one embodiment, a premium item is included with the package, such as a coupon, product sample or toy, appropriate for the consumer based upon the information provided, e.g., a particular age, gender, health status, and so forth.

In some embodiments, customized packaging options can also be offered. For example, as shown in FIG. 23A, a single-serving pouch package 2302 can be used. Alternatively a covered bowl single serving package 2304 can be used as shown in FIG. 23B. Alternatively, a box 2306 type of packaging can be used as shown in FIG. 23C. In another embodiment, not shown, a beverage-type of package is used. In one embodiment, the package contains a single serving. In another embodiment, the package is a consumer-sized box containing more than one serving.

The various food products described herein can be supplemented by adding any type of additive. In one embodiment, the product shipped to the consumer is a blended product such that all of the pieces of the customized food product, as well as any additional additives, have been finely ground and blended with a liquid or semi-liquid food product, to produce any number of products. These can include, but are not limited to, a chilled or semi-solid beverage (e.g., milk shake, malt, smoothie, etc.), or frozen novelty treat on a stick (e.g., dairy-based, fruit-based, including, for example, chocolate-type treats, with or without nuts, frozen candy bars, pies and cakes, and so forth, further including and any combination thereof), snack on a stick (e.g., corn dog, etc.), and so forth. In another alternative embodiment, the customized food product is a blended food product, which includes meat. In yet another embodiment, the customized food product is virtually any type of food product as defined above in the definition section.

In an alternative embodiment, puffable half-product pellets, together with any other selected additives, are shipped to the consumer, together with instructions on preparation, if necessary. Puffable half-products can be expanded or puffed by the consumer or at any suitable location to produce a variety of foods, including, but not limited to, cereals, cereal-based snacks and beverages, through exposure to a suitable energy source. The package can also include savory toppings, and instructions on how to apply the toppings. The various ways of selecting, distributing and preparing half-products are described in U.S. patent application Ser. No. 09/596,275, supra. As such, all of the above described embodiments which reference a "cereal base" can be modified accordingly to instead use one or more "half-products."

Additionally, whether ordering a customized finished cereal or a customized half-product (or any other type of customized food product), the consumer can further customize as desired at home by adding various flavorings, fresh particulates (e.g., sliced bananas, strawberries, dried fruits, nuts, and so forth), in addition to the conventional products typically added to the food, e.g., milk and milk products are typically added to cereal, and so forth. The consumer can further "finish" a customized food product in any manner, such as by cooking, baking, grilling, heating, puffing, popping, etc. For example if a hot cereal has been chosen as the customized food product, the consumer can heat it in the microwave prior to serving. Other products may need to be thawed, kept chilled, and so forth. Additionally, the consumer can grind a finished or freshly puffed cereal, as desired, to create any type of grain-based beverage, for example, or other chilled or frozen product at home.

CONCLUSION

The present invention provides a revolutionary new way in which to select, order and deliver customized food products such as soups, salads, meats, cereals, cereal-based snacks, beverages, frozen products, entire meals, and so forth. With this process it is now possible to manipulate a large number of variables in order to provide customization. As a result, consumers now have the ability to select food products, customized for their own taste and health needs, using direct communication with a supplier.

In one embodiment, a convenient, easy-to-use, consumer friendly Internet-based sales model is used. Such a model offers personalized, real-time communication. Furthermore, in addition to providing a unique and customized food product, the consumer also receives relevant and useful nutrition and health information, including a customized nutrition label and ingredient listing. The mass customization strategy of the present invention allows consumers all over the world to select, order and enjoy their own customized food products without ever having to leave home. This approach also allows the manufacturer to learn from their consumers as to what varieties/foods are the most successful, in essence identifying new and emerging consumer needs. In turn, the manufacturer can offer new "mass-produced" products to even more consumers.

In one embodiment, the consumer can choose from a nearly infinite selection of cereal and snack products ranging from healthy and light snacks to hearty meals. The resulting product has a high value to the consumer in that it has been customized to their own particular requirements, whether taste, health and/or nutrition, as compared with existing food options. Still another advantage is that products can be prepared having very particular tastes and/or nutritional properties. For example, additives can be formulated with particular nutritional features such as enhanced vitamin, mineral, fiber or protein fortification.

Although specific embodiments have been illustrated and described herein, it will be appreciated by those of ordinary skill in the art that any arrangement, which is calculated to achieve the same purpose may be substituted for the specific embodiments shown. This application is intended to cover any adaptations or variations of the invention. It is intended that this invention be limited only by the following claims, and the full scope of equivalents thereof.

What is claimed is:
1. A computer-implemented method for selecting and ordering a customized food product comprising:
viewing, on a display of a communication device, a list of choices designed to allow a consumer to design a customized food product made from a ready-to-eat cereal base or grain-based half-product pellets, along with various additives;
making a selection from the list, using a user interface of the communication device, the list having choices including customized food product choices, customized food ingredients choices, and customized food category choices;
creating a customized food product order made from a ready-to-eat cereal base or grain-based half-product pellets along with the selection made from the list including customized food product choices, customized food ingredients choices, and customized food category choices; and communicating the customized food product order to a merchant remote from the communication device.

2. The method of claim 1 further comprising modifying the selection prior to transmission of the selection.

3. The method of claim 2 wherein the selection is modified by accessing the list of customized food ingredient choices and adding or removing ingredients from the list.

4. The method of claim 3 wherein access to the list of customized food ingredients choices is limited to certain ingredient choices.

5. The method of claim 1 further comprising receiving the customized food product from a remote source.

6. The method recited in claim 5 wherein the preferences are communicated using a computerized survey.

7. The method of claim 5 further comprising receiving nutritional information about the one or more customized food products.

8. The method of claim 7 wherein the nutritional information is received on a customized nutritional label generated specifically for said customized food product.

9. The method of claim 5 further comprising receiving advice on a customized nutritional label generated for the customized food product.

10. The method of claim 9 wherein the advice is located on an insert shipped with the customized food product.

11. The method of claim 5 further comprising completing a survey, the survey designed to determine one or more consumer preferences.

12. The method of claim 11 wherein the survey asks questions regarding taste preferences for at least one of grains, flavors, sweetness, nutrition, serving size, packaging, particulates, quantity, type and form.

13. The method of claim 11 wherein personalized health and nutrition information is provided in response to the completed survey.

14. The method of claim 11 wherein the survey is inferential or inductive.

15. The method recited in claim 14 wherein the one or more preferences relate to topics selected from the group consisting of health concerns, diet requirements, taste preferences, serving size preference, product packaging preference, economic preference and lifestyle choices.

16. The method of claim 1 further comprising first choosing a path selected from the group consisting of viewing and selecting customized food product choices, viewing and selecting customized food ingredient choices, and viewing and selecting customized food category choices.

17. The method of claim 1 further comprising identifying the selection with a unique code.

18. The method of claim 17 further comprising storing the unique code in a merchant database.

19. The method of claim 18 further comprising manufacturing the customized food product in a custom finishing facility.

20. The method of claim 1 wherein the customized food ingredient list includes additives selected from the group consisting of sweeteners, nutrients, flavorings and particulates.

21. A method of selecting and ordering customized food products utilizing a computer-based system, comprising:

listing food additive choices on a display of a communication device accessible by a consumer;

obtaining consumer food additive selections via a user interface of the communication device;

creating a customized food product order made from a ready-to-eat cereal base or grain-based half-product pellets based on the selection made from a list including customized food product choices, customized food ingredients choices, and customized food category choices;

communicating the consumer food additive selections to a merchant remote from the communication device;

designing a customized food product based, at least in part, on the consumer food additive selections, wherein the customized food product contains a ready-to-eat cereal base or grain-based half product pellets, along with one or more other additives;

ordering the customized food product from a production facility;

producing the customized food product; and shipping the customized food product to the consumer.

22. The method of claim 21, further comprising:

supplying a consumer with a survey to obtain consumer information; and retrieving the consumer information from the survey.

23. The method of claim 22, wherein the customized food product is designed, at least in part, based on the consumer information from the survey.

24. The method of claim 22, wherein the survey includes questions related to topics selected from the group consisting of health concerns, taste preferences, diet requirements, lifestyle choices, serving size preference, product packaging preference and economic preference.

25. The method of claim 22, wherein the survey asks questions regarding consumer preference for, at least a majority of, grains, flavors, sweetness, nutrition, serving size, packaging, particulates, quantity, type and form.

26. The method of claim 22, further comprising:

providing health and nutrition advice to the consumer in response to the consumer information.

27. The method of claim 26, wherein providing the advice comprises:

generating a database containing contents of known food products;

collecting data from a consumer about personal eating habits;

determining a personalized profile for the consumer with the database; and dispensing the health and nutrition advice based on the personalized profile.

28. The method of claim 22, further comprising:

assigning a code to the customized food product.

29. The method of claim 22, wherein the consumer information is retrieved by telephone, facsimile, mail or computer.

30. The method of claim 21, wherein the additive choices include sweeteners, nutrients, flavorings and particulates.

31. The method of claim 21, wherein producing the customized food product includes combining one or more food product components and pre-selected additives in a sequential manner.

32. The method of claim 21, further comprising:

isolating potential allergen additives in the production facility.

33. The method of claim 21, further comprising:

attaching nutrients to the cereal base or half-product using electrostatic attraction.

34. A computer-implemented method of selecting and ordering customized food products utilizing a computer-based system, comprising:

listing food additive choices on a display of a communication device accessible by a consumer, with the consumer viewing a list of choices designed to allow the consumer to design a customized food product made from a cereal base or grain-based half-product pellets, along with various additives;

obtaining consumer food additive selections via a user interface of the communication device, with the consumer making a selection from the list, the list having choices including customized food product choices, customized food ingredients choices, and customized food category choices;

creating a customized food product order made from a ready-to-eat cereal base or gin-based half-product pellets based on the selection made from the list including customized food product choices, customized food ingredients choices, and customized food category choices;

communicating the consumer food additive selections to a merchant remote from the communication device;

designing a customized food product based, at least in part, on the consumer food additive selections, wherein the customized food product contains a ready-to-eat cereal base or grain-based half product pellets, along with one or more other additives;

ordering the customized food product from a production facility;

producing the customized food product; and shipping the customized food product to the consumer.

* * * * *